(12) United States Patent
Duggan et al.

(10) Patent No.: US 6,211,191 B1
(45) Date of Patent: Apr. 3, 2001

(54) INTEGRIN RECEPTOR ANTAGONISTS

(75) Inventors: Mark E. Duggan, Schwenksville; James J. Perkins, Churchville; Robert S. Meissner, Schwenksville, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/212,510

(22) Filed: Dec. 15, 1998

Related U.S. Application Data

(60) Provisional application No. 60/069,909, filed on Dec. 17, 1997, provisional application No. 60/083,250, filed on Apr. 27, 1998, and provisional application No. 60/092,630, filed on Jul. 13, 1998.

(51) Int. Cl.$^7$ .................. C07D 403/06; C07D 401/06; A61K 31/506; A61P 19/02; A61P 35/00

(52) U.S. Cl. .................. 514/274; 544/296; 544/316; 562/13

(58) Field of Search .................. 562/13; 544/296, 544/316; 514/274

(56) References Cited

U.S. PATENT DOCUMENTS

| 4,929,618 | 5/1990 | Koda et al. ........................... 514/253 |
| 5,455,243 | 10/1995 | Duggan et al. ...................... 514/218 |
| 5,668,159 | 9/1997 | Jin et al. ............................... 514/363 |

FOREIGN PATENT DOCUMENTS

| 503548 | * 9/1992 | (DE) . |
| 0796 855 A1 | 9/1997 | (EP) . |
| WO 9506038 | * 3/1995 | (WO) . |
| WO 95/32710 | 7/1995 | (WO) . |
| WO 97/37655 | 10/1997 | (WO) . |
| WO 98/08840 | 3/1998 | (WO) . |
| WO 98/18460 | 5/1998 | (WO) . |
| WO 98/18461 | 5/1998 | (WO) . |
| WO 98/31359 | 7/1998 | (WO) . |

OTHER PUBLICATIONS

Annual Reports in Medicinal Chemistry, vol. 31, James Bristol, ed., Academic Press, San Diego, 1996, pp. 191–200.*

Engleman et al, J. Clin. Invest., 1997, 99, 2284–2292.*

"Fields Virology, Third Ed.", B. N. Fields et al eds., Lippincott–Raven, Philadelphia, 1996, p. 431.*

Ricouart, A. et al., "Design of Potent Protein Kinase Inhibitors Using the Bisubstrate Approach," J. Med. Chem., vol. 34, No. 1, pp. 73–78 (1991).

* cited by examiner

Primary Examiner—Richard L. Raymond
Assistant Examiner—Beby Jayaram
(74) Attorney, Agent, or Firm—Philippe L. Durette; Melvin Winokur

(57) ABSTRACT

The present invention relates to compounds and derivatives thereof, their synthesis, and their use as integrin receptor antagonists. More particularly, the compounds of the present invention are antagonists of the integrin receptors $\alpha v\beta 3$, $\alpha v\beta 5$, and/or $\alpha v\beta 6$ and are useful for inhibiting bone resorption, treating and preventing osteoporosis, and inhibiting vascular restenosis, diabetic retinopathy, macular degeneration, angiogenesis, atherosclerosis, inflammation, wound healing, viral disease, tumor growth, and metastasis.

23 Claims, No Drawings

INTEGRIN RECEPTOR ANTAGONISTS

CROSS-REFERENCE TO RELATED APPLICATIONS

The present invention is related to U.S. provisional applications Ser. Nos. 60/069,909, filed Dec. 17, 1997; 60/083,250, filed Apr. 27, 1998; and 60/092,630, filed Jul. 13, 1998; the contents of each of which are hereby incorporated by reference.

FIELD OF THE INVENTION

The present invention relates to compounds and derivatives thereof, their synthesis, and their use as integrin receptor antagonists. More particularly, the compounds of the present invention are antagonists of the integrin receptors $\alpha v\beta 3$, $\alpha v\beta 5$, and/or $\alpha v\beta 6$ and are useful for inhibiting bone resorption, treating and preventing osteoporosis, and inhibiting vascular restenosis, diabetic retinopathy, macular degeneration, angiogenesis, atherosclerosis, inflammation, wound healing, viral disease, tumor growth, and metastasis.

BACKGROUND OF THE INVENTION

It is believed that a wide variety of disease states and conditions can be mediated by acting on integrin receptors and that integrin receptor antagonists represent a useful class of drugs. Integrin receptors are heterodimeric transmembrane proteins through which cells attach and communicate with extracellular matrices and other cells (See S. B. Rodan and G. A. Rodan, "Integrin Function In Osteoclasts", *Journal of Endocrinology*, Vol. 154, S47–S56 (1997), which is incorporated by reference herein in its entirety).

In one aspect of the present invention, the compounds herein are useful for inhibiting bone resorption. Bone resorption is mediated by the action of cells known as osteoclasts. Osteoclasts are large multinucleated cells of up to about 400 mm in diameter that resorb mineralized tissue, chiefly calcium carbonate and calcium phosphate, in vertebrates. Osteoclasts are actively motile cells that migrate along the surface of bone, and can bind to bone, secrete necessary acids and proteases, thereby causing the actual resorption of mineralized tissue from the bone. More specifically, osteoclasts are believed to exist in at least two physiological states, namely, the secretory state and the migratory or motile state. In the secretory state, osteoclasts are flat, attach to the bone matrix via a tight attachment zone (sealing zone), become highly polarized, form a ruffled border, and secrete lysosomal enzymes and protons to resorb bone. The adhesion of osteoclasts to bone surfaces is an important initial step in bone resorption. In the migratory or motile state, the osteoclasts migrate across bone matrix and do not take part in resorption until they again attach to bone.

Integrins are involved in osteoclast attachment, activation and migration. The most abundant integrin in osteoclasts, e.g., in rat, chicken, mouse and human osteoclasts, is an integrin receptor known as $\alpha v\beta 3$, which is thought to interact in bone with matrix proteins that contain the RGD sequence. Antibodies to $\alpha v\beta 3$ block bone resorption in vitro indicating that this integrin plays a key role in the resorption process. There is increasing evidence to suggest that $\alpha v\beta 3$ ligands can be used effectively to inhibit osteoclast mediated bone resorption in vivo in mammals.

The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid-induced osteoporosis. All of these conditions are characterized by bone loss, resulting from an imbalance between bone resorption, i.e. breakdown, and bone formation, which continues throughout life at the rate of about 14% per year on the average. However, the rate of bone turnover differs from site to site; for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

In the United States, there are currently about 20 million people with detectable fractures of the vertebrae due to osteoporosis. In addition, there are about 250,000 hip fractures per year attributed to osteoporosis. This clinical situation is associated with a 12% mortality rate within the first two years, while 30% of the patients require nursing home care after the fracture.

Individuals suffering from all the conditions listed above would benefit from treatment with agents which inhibit bone resorption.

Additionally, $\alpha v\beta 3$ ligands have been found to be useful in treating and/or inhibiting restenosis, i.e. recurrence of stenosis after corrective surgery on the heart valve, atherosclerosis, diabetic retinopathy, macular degeneration, and angiogenesis, i.e. formation of new blood vessels. Moreover, it has been postulated that the growth of tumors depends on an adequate blood supply, which in turn is dependent on the growth of new vessels into the tumor; thus, inhibition of angiogenesis can cause tumor regression in animal models (See *Harrison's Principles of Internal Medicine*, 12th ed., 1991, which is incorporated by reference herein in its entirety). Therefore, $\alpha v\beta 3$ antagonists which inhibit angiogenesis can be useful in the treatment of cancer by inhibiting tumor growth (See e.g., Brooks et al., *Cell*, 79:1157–1164 (1994), which is incorporated by reference herein in its entirety).

Moreover, compounds of this invention can also inhibit neovascularization by acting as antagonists of the integrin receptor, $\alpha v\beta 5$. A monoclonal antibody for $\alpha v\beta 5$ has been shown to inhibit VEGF-induced angiogenesis in rabbit cornea and the chick chorioallantoic membrane model (See M. C. Friedlander, et al., *Science* 270, 1500–1502, (1995), which is incorporated by reference herein in its entirety). Thus, compounds that antagonize $\alpha v\beta 5$ are useful for treating and preventing macular degeneration, diabetic retinopathy, tumor growth, and metastasis.

Additionally, compounds of the instant invention can inhibit angiogenesis and inflammation by acting as antagonists of the integrin receptor, $\alpha v\beta 6$, which is expressed during the later stages of wound healing and remains expressed until the wound is closed (See Christofidou-Solomidou, et al., "Expression and Function of Endothelial Cell $\alpha v$ Integrin Receptors in Wound-Induced Human Angiogenesis in Human Skin/SCID Mice Chimeras, *American Journal of Pathology*, Vol. 151, No. 4, pp. 975–983 (October 1997), which is incorporated by reference herein in its entirety). It is postulated that $\alpha v\beta 6$ plays a role in the remodeling of the vasculature during the later stages of angiogenesis. Also, $\alpha v\beta 6$ participates in the modulation of epithelial inflammation and is induced in response to local injury or inflammation (See Xiao-Zhu Huang, et al., "Inactivation of the Integrin $\beta 6$ Subunit Gene Reveals a Role of Epithelial Integrins in Regulating Inflammation in the Lungs and Skin," *Journal of Cell Biology*, Vol. 133, No. 4, pp. 921–928 (May 1996), which is incorporated by reference herein in its entirety). Accordingly, compounds that antagonize αvβ6 are useful in treating or preventing cancer by inhibiting tumor growth and metastasis.

In addition, certain compounds of this invention antagonize both the αvβ3 and αvβ5 receptors. These compounds, referred to as "dual αvβ3/αvβ5 antagonists," are useful for inhibiting bone resorption, treating and preventing osteoporosis, and inhibiting vascular restenosis, diabetic retinopathy, macular degeneration, angiogenesis, atherosclerosis, inflammation, tumor growth, and metastasis.

In addition, certain compounds of this invention are useful as mixed αvβ3, αvβ5, and αvβ6 receptor antagonists.

It is therefore an object of the present invention to provide compounds which are useful as integrin receptor antagonists.

It is another object of the present invention to provide compounds which are useful as αvβ3 receptor antagonists.

It is another object of the present invention to provide compounds which are useful as αvβ5 receptor antagonists.

It is another object of the present invention to provide compounds which are useful as αvβ6 receptor antagonists.

It is another object of the present invention to provide compounds which are useful as dual αvβ3/αvβ5 receptor antagonists.

It is another object of the present invention to provide compounds which are useful as mixed αvβ3, αvβ5, and αvβ6 receptor antagonists.

It is another object of the present invention to provide pharmaceutical compositions comprising integrin receptor antagonists.

It is another object of the present invention to provide methods for making the pharmaceutical compositions of the present invention.

It is another object of the present invention to provide methods for eliciting an integrin receptor antagonizing effect in a mammal in need thereof by administering the compounds and pharmaceutical compositions of the present invention.

It is another object of the present invention to provide compounds and pharmaceutical compositions useful for inhibiting bone resorption, restenosis, atherosclerosis, inflammation, viral disease, diabetic retinopathy, macular degeneration, angiogenesis, tumor growth, and metastasis.

It is another object of the present invention to provide compounds and pharmaceutical compositions useful for treating osteoporosis.

It is another object of the present invention to provide methods for inhibiting bone resorption, restenosis, atherosclerosis, inflammation, viral disease, diabetic retinopathy, macular degeneration, angiogenesis, tumor growth, and metastasis.

It is another object of the present invention to provide methods for treating osteoporosis.

These and other objects will become readily apparent from the detailed description which follows.

SUMMARY OF THE INVENTION

The present invention relates to compounds of the formula

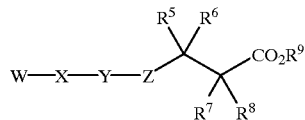

wherein W is selected from the group consisting of

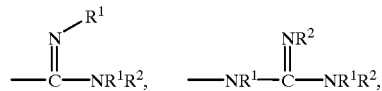

a 5- or 6-membered monocyclic aromatic or nonaromatic ring system having 0, 1, 2, 3 or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents, and a 9- to 14-membered polycyclic ring system, wherein one or more of the rings is aromatic, and wherein the polycyclic ring system has 0, 1, 2, 3 or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents;

X is selected from the group consisting of
—$(CH_2)_v$—, wherein any methylene ($CH_2$) carbon atom is either unsubstituted or substituted with one or two $R^1$ substitutents; and a 5- or 6-membered monocyclic aromatic or nonaromatic ring system having 0, 1, 2, 3 or 4 heteroatoms selected from the group consisting of N, O, and S, wherein the ring nitrogen atoms are unsubstituted or substituted with one $R^1$ substituent and the ring carbon atoms are unsubstituted or substituted with one or two $R^1$ substituents;

Y is selected from the group consisting of
—$(CH_2)_m$—,
—$(CH_2)_m$—O—$(CH_2)_n$—,
—$(CH_2)_m$—$NR^4$—$(CH_2)_n$—,
—$(CH_2)_m$—S—$(CH_2)_n$—,
—$(CH_2)_m$—SO—$(CH_2)_n$—,
—$(CH_2)_m$—$SO_2$—$(CH_2)_n$—,
—$(CH_2)_m$—O—$(CH_2)_n$—O—$(CH_2)_p$—,
—$(CH_2)_m$—O—$(CH_2)_n$—$NR^4$—$(CH_2)_p$—,
—$(CH_2)_m$—$NR^4$—$(CH_2)_n$—$NR^4$—$(CH_2)_p$—,
—$(CH_2)_m$—O—$(CH_2)_n$—S—$(CH_2)_p$—,
—$(CH_2)_m$—S—$(CH_2)_n$—S—$(CH_2)_p$—,
—$(CH_2)_m$—$NR^4$—$(CH_2)_n$—S—$(CH_2)_p$—,
—$(CH_2)_m$—$NR^4$—$(CH_2)_n$—O—$(CH_2)_p$—,
—$(CH_2)_m$—S—$(CH_2)_n$—O—$(CH_2)_p$—, and
—$(CH_2)_m$—S—$(CH_2)_n$—$NR^4$—$(CH_2)_p$—,
wherein any methylene ($CH_2$) carbon atom in Y, other than in $R^4$, can be substituted by one or two $R^3$ substituents;

Z is a 6–11 membered aromatic or nonaromatic mono- or polycyclic ring system having 0 to 6 heteroatoms selected from the group consisting of N, O, and S, and wherein the ring system is either unsubstituted or substituted with 0, 1, 2, 3 or 4 oxo or thio substituents, and either unsubstituted or substituted with one or more substituents independently selected from the group consisting of $R^{10}$, $R^{11}$, $R^{12}$ and $R^{13}$, provided that Z is not phenyl or pyridyl;

$R^1$ and $R^2$ are each independently selected from the group consisting of hydrogen, halogen, $C_{1-10}$ alkyl, $C_{3-8}$ cycloalkyl, $C_{3-8}$ cycloheteroalkyl, $C_{3-8}$ cycloalkyl $C_{1-6}$ alkyl, $C_{3-8}$ cycloheteroalkyl $C_{1-6}$ alkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $(C_{1-6}$ alkyl$)_p$amino, $(C_{1-6}$ alkyl$)_p$amino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-3}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, $C_{1-6}$ alkyloxy $C_{1-6}$ alkyl, nitro, cyano, trifluoromethyl, trifluoromethoxy, trifluoroethoxy, $C_{1-8}$ alkyl-$S(O)_p$, $(C_{1-8}$ alkyl$)_p$aminocarbonyl, $C_{1-8}$ alkyloxycarbonylamino, $(C_{1-8}$ alkyl$)_p$aminocarbonyloxy, (aryl $C_{1-8}$ alkyl$)_p$amino, (aryl$)_p$amino, aryl $C_{1-8}$ alkylsulfonylamino, and $C_{1-8}$ alkylsulfonylamino;

or two $R^1$ substituents, when on the same carbon atom, are taken together with the carbon atom to which they are attached to form a carbonyl group;

each $R^3$ is independently selected from the group consisting of hydrogen, aryl, $C_{1-10}$ alkyl, aryl-$(CH_2)_r$—O—$(CH_2)_s$—, aryl-$(CH_2)_r$S$(O)_p$—$(CH_2)_s$—, aryl-$(CH_2)_r$—C(O)—$(CH_2)_s$—, aryl-$(CH_2)_r$—C(O)—N$(R^4)$—$(CH_2)_s$—, aryl-$(CH_2)_r$—N$(R^4)$—C(O)—$(CH_2)_s$—, aryl-$(CH_2)_r$—N$(R^4)$—$(CH_2)_s$—, halogen, hydroxyl, oxo, trifluoromethyl, $C_{1-8}$ alkylcarbonylamino, aryl $C_{1-5}$ alkoxy, $C_{1-5}$ alkoxycarbonyl, $(C_{1-8}$ alkyl$)_p$aminocarbonyl, $C_{1-6}$ alkylcarbonyloxy, $C_{3-8}$ cycloalkyl, $(C_{1-6}$ alkyl$)_p$amino, amino $C_{1-6}$ alkyl, arylaminocarbonyl, aryl $C_{1-5}$ alkylaminocarbonyl, aminocarbonyl, aminocarbonyl $C_{1-6}$ alkyl, hydroxycarbonyl, hydroxycarbonyl $C_{1-6}$ alkyl, HC≡C—$(CH_2)_t$—, $C_{1-6}$ alkyl-C≡C—$(CH_2)_t$—, $C_{3-7}$ cycloalkyl-C≡C—$(CH_2)_t$—, aryl-C≡C—$(CH_2)_t$—, $C_{1-6}$ alkylaryl-C≡C—$(CH_2)_t$—, $CH_2$=CH—$(CH_2)_t$—, $C_{1-6}$ alkyl-CH=CH—$(CH_2)_t$—, $C_{3-7}$ cycloalkyl-CH=CH—$(CH_2)_t$—, aryl-CH=CH—$(CH_2)_t$—, $C_{1-6}$ alkylaryl-CH=CH—$(CH_2)_t$—, $C_{1-6}$ alkyl-SO$_2$—$(CH_2)_t$—, $C_{1-6}$ alkylaryl-SO$_2$—$(CH_2)_t$—, $C_{1-6}$ alkoxy, aryl $C_{1-6}$ alkoxy, aryl $C_{1-6}$ alkyl, $(C_{1-6}$ alkyl$)_p$amino $C_{1-6}$ alkyl, (aryl$)_p$amino, (aryl$)_p$amino $C_{1-6}$ alkyl, (aryl $C_{1-6}$ alkyl$)_p$amino, (aryl $C_{1-6}$ alkyl$)_p$amino $C_{1-6}$ alkyl, arylcarbonyloxy, aryl $C_{1-6}$ alkylcarbonyloxy, $(C_{1-6}$ alkyl$)_p$aminocarbonyloxy, $C_{1-8}$ alkylsulfonylamino, arylsulfonylamino, $C_{1-8}$ alkylsulfonylamino $C_{1-6}$ alkyl, arylsulfonylamino $C_{1-6}$ alkyl, aryl $C_{1-6}$ alkylsulfonylamino, aryl $C_{1-6}$ alkylsulfonylamino $C_{1-6}$ alkyl, $C_{1-8}$ alkoxycarbonylamino, $C_{1-8}$ alkoxycarbonylamino $C_{1-8}$ alkyl, aryloxycarbonylamino $C_{1-8}$ alkyl, aryl $C_{1-8}$ alkoxycarbonylamino, aryl $C_{1-8}$ alkoxycarbonylamino $C_{1-8}$ alkyl, $C_{1-8}$ alkylcarbonylamino, $C_{1-8}$ alkylcarbonylamino $C_{1-6}$ alkyl, arylcarbonylamino $C_{1-6}$ alkyl, aryl $C_{1-6}$ alkylcarbonylamino, aryl $C_{1-6}$ alkylcarbonylamino $C_{1-6}$ alkyl, aminocarbonylamino $C_{1-6}$ alkyl, $(C_{1-8}$ alkyl$)_p$aminocarbonylamino, $(C_{1-8}$ alkyl$)_p$aminocarbonylamino $C_{1-6}$ alkyl, (aryl$)_p$aminocarbonylanino $C_{1-6}$ alkyl, (aryl $C_{1-8}$ alkyl$)_p$aminocarbonylamino, (aryl $C_{1-8}$ alkyl$)_p$aminocarbonylamino $C_{1-6}$ alkyl, aminosulfonylamino $C_{1-6}$ alkyl, $(C_{1-8}$ alkyl$)_p$aminosulfonylamino, $(C_{1-8}$ alkyl$)_p$aminosulfonylamino $C_{1-6}$ alkyl, (aryl$)_p$aminosulfonylamino $C_{1-6}$ alkyl, (aryl $C_{1-8}$ alkyl$)_p$aminosulfonylamino, (aryl $C_{1-8}$ alkyl$)_p$aminosulfonylamino $C_{1-6}$ alkyl, $C_{1-6}$ alkylsulfonyl, $C_{1-6}$ alkylsulfonyl $C_{1-6}$ alkyl, arylsulfonyl $C_{1-6}$ alkyl, aryl $C_{1-6}$ alkylsulfonyl, aryl $C_{1-6}$ alkylsulfonyl $C_{1-6}$ alkyl, $C_{1-6}$ alkylcarbonyl, $C_{1-6}$ alkylcarbonyl $C_{1-6}$ alkyl, arylcarbonyl $C_{1-6}$ alkyl, aryl $C_{1-6}$ alkylcarbonyl, aryl $C_{1-6}$ alkylcarbonyl $C_{1-6}$ alkyl, $C_{1-6}$ alkylthiocarbonylamino, $C_{1-6}$ alkylthiocarbonylamino $C_{1-6}$ alkyl, arylthiocarbonylamino $C_{1-6}$ alkyl, aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl$)_p$aminocarbonyl $C_{1-6}$ alkyl,
(aryl $C_{1-8}$ alkyl$)_p$aminocarbonyl, and
(aryl $C_{1-8}$ alkyl$)_p$aminocarbonyl $C_{1-6}$ alkyl;
or two $R^3$ substituents, when on the same carbon atom are taken together with the carbon atom to which they are attached to form a carbonyl group or a cyclopropyl group, wherein any of the alkyl groups of $R^3$ are either unsubstituted or substituted with one to three $R^1$ substituents, and provided that each $R^3$ is selected such that in the resultant compound the carbon atom or atoms to which $R^3$ is attached is itself attached to no more than one heteroatom;

each $R^4$ is independently selected from the group consisting of
hydrogen,
aryl,
aminocarbonyl,
$C_{3-8}$ cycloalkyl,
amino $C_{1-6}$ alkyl,
(aryl$)_p$aminocarbonyl,
(aryl $C_{1-5}$ alkyl$)_p$aminocarbonyl,
hydroxycarbonyl $C_{1-6}$ alkyl,
$C_{1-8}$ alkyl,
aryl $C_{1-6}$ alkyl,
$(C_{1-6}$ alkyl$)_p$amino $C_{2-6}$ alkyl,
(aryl $C_{1-6}$ alkyl$)_p$amino $C_{2-6}$ alkyl,
$C_{1-8}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
$(C_{1-8}$ alkyl$)_p$aminocarbonyl,
aminosulfonyl,
$C_{1-8}$ alkylaminosulfonyl,
(aryl$)_p$aminosulfonyl,
(aryl $C_{1-8}$ alkyl$)_p$aminosulfonyl,
arylsulfonyl,
aryl$C_{1-6}$ alkylsulfonyl,
$C_{1-6}$ alkylthiocarbonyl,
arylthiocarbonyl, and
aryl $C_{1-6}$ alkylthiocarbonyl,
wherein any of the alkyl groups of $R^4$ are either unsubstituted or substituted with one to three $R^1$ substituents;
$R^5$ and $R^6$ are each independently selected from the group consisting of
hydrogen,
$C_{1-10}$ alkyl,
aryl,
aryl-$(CH_2)_r$—O—$(CH_2)_s$—,
aryl-$(CH_2)_r$S(O)$_p$—$(CH_2)_s$—,
aryl-$(CH_2)_r$—C(O)—$(CH_2)_s$—,
aryl-$(CH_2)_r$—C(O)—N(R$^4$)—$(CH_2)_s$—,
aryl-$(CH_2)_r$—N(R$^4$)—C(O)—$(CH_2)_s$—,
aryl-$(CH_2)_r$—N(R$^4$)—$(CH_2)_s$—, halogen,
hydroxyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl-C≡C—$(CH_2)_t$—,
$C_{3-7}$ cycloalkyl-C≡C—$(CH_2)_t$—,
aryl-C≡C—$(CH_2)_t$—,
$C_{1-6}$ alkylaryl-C≡C—$(CH_2)_t$—,
$CH_2$=CH—$(CH_2)_t$—,
$C_{1-6}$ alkyl-CH=CH—$(CH_2)_t$—,
$C_{3-7}$ cycloalkyl-CH=CH—$(CH_2)_t$—,
aryl-CH=CH—$(CH_2)_t$—,
$C_{1-6}$ alkylaryl-CH=CH—$(CH_2)_t$—,
$C_{1-6}$ alkyl-SO$_2$—$(CH_2)_t$—,
$C_{1-6}$ alkylaryl-SO$_2$—$(CH_2)_t$—,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
(aryl$)_p$amino,
(aryl$)_p$amino $C_{1-6}$ alkyl,
(aryl $C_{1-6}$ alkyl$)_p$amino,
(aryl $C_{1-6}$ alkyl$)_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl, $(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl$)_p$aminocarbonyl $C_{1-6}$ alkyl,
(aryl $C_{1-8}$ alkyl$)_p$aminocarbonyl,
and (aryl $C_{1-8}$ alkyl$)_p$aminocarbonyl $C_{1-6}$ alkyl;
or $R^5$ and $R^6$ are taken together with the carbon atom
to which they are attached to for a carbonyl group,
wherein any of the alkyl groups of $R^5$ or $R^6$ are either unsubstituted or substituted with one to three $R^1$ substituents, and provided that each $R^5$ and $R^6$ are selected such that in the resultant compound the carbon atom to which $R^5$ and $R^6$ are attached is itself attached to no more than one heteroatom;
$R^7$ and $R^8$ are each independently selected from the group consisting of
hydrogen,
$C_{1-10}$ alkyl,
aryl,
aryl-$(CH_2)_r$—O—$(CH_2)_s$—,
aryl-$(CH_2)_r$S(O)$_p$—$(CH_2)_s$—,
aryl-$(CH_2)_r$—C(O)—$(CH_2)_s$—,
aryl-$(CH_2)_r$—C(O)—N($R^4$)—$(CH_2)_s$—,
aryl-$(CH_2)_r$—N($R^4$)—C(O)—$(CH_2)_s$—,
aryl-$(CH_2)_r$—N($R^4$)—$(CH_2)_s$—,
halogen,
hydroxyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl-C≡C—$(CH_2)_t$—,
$C_{3-7}$ cycloalkyl-C≡C—$(CH_2)_t$—,
aryl-C≡C—$(CH_2)_t$—,
$C_{1-6}$ alkylaryl-C≡C—$(CH_2)_t$—,
$CH_2$=CH—$(CH_2)_t$—,
$C_{1-6}$ alkyl-CH=CH—$(CH_2)_t$—,
$C_{3-7}$ cycloalkyl-CH=CH—$(CH_2)_t$—,
aryl-CH=CH—$(CH_2)_t$—,
$C_{1-6}$ alkylaryl-CH=CH—$(CH_2)_t$—,
$C_{1-6}$ alkyl-SO$_2$—$(CH_2)_t$—,
$C_{1-6}$ alkylaryl-SO$_2$—$(CH_2)_t$—,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
(aryl$)_p$amino,
(aryl$)_p$amino $C_{1-6}$ alkyl,
(aryl $C_{1-6}$ alkyl$)_p$amino,
(aryl $C_{1-6}$ alkyl$)_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylcarbonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
arylaminocarbonylamino,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl, (aryl)$_p$aminosulfonylamino C$_{1-6}$ alkyl,
(aryl C$_{1-8}$ alkyl)$_p$aminosulfonylamino,
(aryl C$_{1-8}$ alkyl)$_p$aminosulfonylamino C$_{1-6}$ alkyl,
C$_{1-6}$ alkylsulfonyl,
C$_{1-6}$ alkylsulfonyl C$_{1-6}$ alkyl,
arylsulfonyl C$_{1-6}$ alkyl,
aryl C$_{1-6}$ alkylsulfonyl,
aryl C$_{1-6}$ alkylsulfonyl C$_{1-6}$ alkyl,
C$_{1-6}$ alkylcarbonyl,
C$_{1-6}$ alkylcarbonyl C$_{1-6}$ alkyl,
arylcarbonyl C$_{1-6}$ alkyl,
aryl C$_{1-6}$ alkylcarbonyl,
aryl C$_{1-6}$ alkylcarbonyl C$_{1-6}$ alkyl,
C$_{1-6}$ alkylthiocarbonylamino,
C$_{1-6}$ alkylthiocarbonylamino C$_{1-6}$ alkyl,
arylthiocarbonylamino C$_{1-6}$ alkyl,
aryl C$_{1-6}$ alkylthiocarbonylamino,
aryl C$_{1-6}$ alkylthiocarbonylamino C$_{1-6}$ alkyl,
(C$_{1-8}$ alkyl)$_p$aminocarbonyl C$_{1-6}$ alkyl,
(aryl)$_p$aminocarbonyl C$_{1-6}$ alkyl,
(aryl C$_{1-8}$ alkyl)$_p$aminocarbonyl,
(aryl C$_{1-8}$ alkyl)$_p$aminocarbonyl C$_{1-6}$ alkyl, and
C$_{7-20}$ polycycyl C$_{0-8}$ alkylsulfonylamino;
wherein any of the alkyl groups of R$^7$ and R$^8$ are either unsubstituted or substituted with one to three R$^1$ substituents, and provided that each R$^7$and R$^8$ are selected such that in the resultant compound the carbon atom to which R$^7$ and R$^8$ are attached is itself attached to no more than one heteroatom;
R$^9$ is selected from the group consisting of
hydrogen;
C$_{1-8}$ alkyl,
aryl,
aryl C$_{1-8}$ alkyl,
C$_{1-8}$ alkylcarbonyloxy C$_{1-4}$ alkyl,
aryl C$_{1-8}$ alkylcarbonyloxy C$_{1-4}$ alkyl,
C$_{1-8}$ alkylaminocarbonylmethylene, and
C$_{1-8}$ dialkylaminocarbonylmethylene;
R$^{10}$, R$^{11}$, R$^{12}$, and R$^{13}$ are each independently selected from the group consisting of
hydrogen,
C$_{1-8}$ alkyl,
aryl,
halogen,
hydroxyl,
oxo,
aminocarbonyl,
C$_{3-8}$ cycloalkyl,
amino C$_{1-6}$ alkyl,
(aryl)$_p$aminocarbonyl,
hydroxycarbonyl,
(aryl C$_{1-5}$ alkyl)$_p$aminocarbonyl,
hydroxycarbonyl C$_{1-6}$ alkyl,
aryl C$_{1-6}$ alkyl,
(C$_{1-6}$ alkyl)$_p$amino C$_{1-6}$ alkyl,
(aryl C$_{1-6}$ alkyl)$_p$amino C$_{2-6}$ alkyl,
C$_{1-8}$ alkylsulfonyl,
C$_{1-8}$ alkoxycarbonyl,
aryloxycarbonyl,
aryl C$_{1-8}$ alkoxycarbonyl,
C$_{1-8}$ alkylcarbonyl,
arylcarbonyl,
aryl C$_{1-6}$ alkylcarbonyl,
(C$_{1-8}$ alkyl)$_p$aminocarbonyl,
aminosulfonyl,
C$_{1-8}$ alkylaminosulfonyl,
(aryl)$_p$aminosulfonyl,
(aryl C$_{1-8}$ alkyl)$_p$aminosulfonyl,
C$_{1-6}$ alkylsulfonyl,
arylsulfonyl,
aryl C$_{1-6}$ alkylsulfonyl,
aryl C$_{1-6}$ alkylcarbonyl,
C$_{1-6}$ alkylthiocarbonyl,
arylthiocarbonyl,
aryl C$_{1-6}$ alkylthiocarbonyl,
aryl-(CH$_2$)$_r$—O—(CH$_2$)$_s$—,
aryl-(CH$_2$)$_r$S(O)$_p$—(CH$_2$)$_s$—,
aryl-(CH$_2$)$_r$—C(O)—(CH$_2$)$_s$—,
aryl-(CH$_2$)$_r$—C(O)—N(R$^4$)—(CH$_2$)$_s$—,
aryl-(CH$_2$)$_r$—N(R$^4$)—C(O)—(CH$_2$)$_s$—,
aryl-(CH$_2$)$_r$—N(R$^4$)—(CH$_2$)$_s$—,
HC≡C—(CH$_2$)$_t$—,
C$_{1-6}$ alkyl-C≡C—(CH$_2$)$_t$—,
C$_{3-7}$ cycloalkyl-C≡C—(CH$_2$)$_t$—,
aryl-C≡C—(CH$_2$)$_t$—,
C$_{1-6}$ alkylaryl-C≡C—(CH$_2$)$_t$—,
CH$_2$=CH—(CH$_2$)$_t$—,
C$_{1-6}$ alkyl-CH=CH—(CH$_2$)$_t$—,
C$_{3-7}$ cycloalkyl-CH=CH—(CH$_2$)$_t$—,
aryl-CH=CH—(CH$_2$)$_t$—,
C$_{1-6}$ alkylaryl-CH=CH—(CH$_2$)$_t$—,
C$_{1-6}$ alkyl-SO$_2$—(CH$_2$)$_t$—,
C$_{1-6}$ alkylaryl-SO$_2$—(CH$_2$)$_t$—,
C$_{1-8}$ alkylcarbonylamino,
aryl C$_{1-5}$ alkoxy,
C$_{1-5}$ alkoxycarbonyl,
(C$_{1-8}$ alkyl)$_p$aminocarbonyl,
C$_{1-6}$ alkylcarbonyloxy,
(C$_{1-6}$ alkyl)$_p$amino,
aminocarbonyl C$_{1-6}$ alkyl,
C$_{1-6}$ alkoxy,
aryl C$_{1-6}$ alkoxy,
(aryl)$_p$amino,
(aryl)$_p$amino C$_{1-6}$ alkyl,
(aryl C$_{1-6}$ alkyl)$_p$amino,
(aryl C$_{1-6}$ alkyl)$_p$amino C$_{1-6}$ alkyl,
arylcarbonyloxy,
aryl C$_{1-6}$ alkylcarbonyloxy,
(C$_{1-6}$ alkyl)$_p$aminocarbonyloxy,
C$_{1-8}$ alkylsulfonylamino,
arylsulfonylamino,
C$_{1-8}$ alkylsulfonylamino C$_{1-6}$ alkyl,
arylsulfonylamino C$_{1-6}$ alkyl,
aryl C$_{1-6}$ alkylsulfonylamino, aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl$)_p$aminocarbonyl $C_{1-6}$ alkyl,
(aryl $C_{1-8}$ alkyl$)_p$aminocarbonyl, and
(aryl $C_{1-8}$ alkyl$)_p$aminocarbonyl $C_{1-6}$ alkyl;
wherein any of the alkyl groups of $R^{10}$, $R^{11}$, $R^{12}$, and $R^{13}$ are either unsubstituted or substituted with to three $R^1$ substituents;
wherein
each m is independently an integer from 0 to 6;
each n is independently an integer from 0 to 6;
each p is independently an integer from 0 to 2;
each r is independently an integer from 1 to 3;
each s is independently an integer from 0 to 3;
each t is an integer from 0 to 3; and
v is independently an integer from 0 to 6;
and the pharmaceutically acceptable salts thereof.

The present invention also relates to pharmaceutical compositions comprising the compounds of the present invention and a pharmaceutically acceptable carrier.

The present invention also relates to methods for making the pharmaceutical compositions of the present invention.

The present invention also relates to methods for eliciting an integrin receptor antagonizing effect in a mammal in need thereof by administering the compounds and pharmaceutical compositions of the present invention.

The present invention also relates to methods for inhibiting bone resorption, restenosis, atherosclerosis, inflammation, viral disease, diabetic retinopathy, macular degeneration, angiogenesis, wound healing, tumor growth, and metastasis by administering the compounds and pharmaceutical compositions of the present invention.

The present invention also relates to methods for treating osteoporosis by administering the compounds and pharmaceutical compositions of the present invention.

DETAILED DESCRIPTION OF THE INVENTION

The present invention relates to compounds useful as integrin receptor antagonists. Representative compounds of the present invention are described by the following chemical formula:

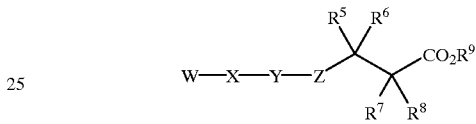

wherein W is selected from the group consisting of

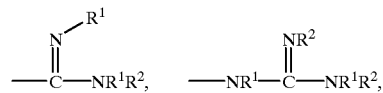

a 5- or 6-membered monocyclic aromatic or nonaromatic ring system having 0, 1, 2, 3 or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents, and a 9- to 14-membered polycyclic ring system, wherein one or more of the rings is aromatic, and wherein the polycyclic ring system has 0, 1, 2, 3 or 4 heteroatoms selected from the group consisting of N, O, and S, and wherein the ring nitrogen atoms are unsubstituted or substituted with one $R^1$ substituent and the ring carbon atoms are unsubstituted or substituted with one or two $R^1$ substituents;

X is selected from the group consisting of
—$(CH_2)_v$—, wherein any methylene $(CH_2)$ carbon atom is either unsubstituted or substituted with one or two $R^1$ substitutents;

and a 5- or 6-membered monocyclic aromatic or nonaromatic ring system having 0, 1, 2, 3 or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents;

Y is selected from the group consisting of
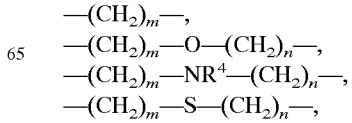

—(CH$_2$)$_m$—SO—(CH$_2$)$_n$—,
—(CH$_2$)$_m$—SO$_2$—(CH$_2$)$_n$—,
—(CH$_2$)$_m$—O—(CH$_2$)$_n$—O—(CH$_2$)$_p$—,
—(CH$_2$)$_m$—O—(CH$_2$)$_n$—NR$^4$—(CH$_2$)$_p$—,
—(CH$_2$)$_m$—NR$^4$—(CH$_2$)$_n$—NR$^4$—(CH$_2$)$_p$—,
—(CH$_2$)$_m$—O—(CH$_2$)$_n$—S—(CH$_2$)$_p$—,
—(CH$_2$)$_m$—S—(CH$_2$)$_n$—S—(CH$_2$)$_p$—,
—(CH$_2$)$_m$—NR$^4$—(CH$_2$)$_n$—S—(CH$_2$)$_p$—,
—(CH$_2$)$_m$—NR$^4$—(CH$_2$)$_n$—O—(CH$_2$)$_p$—,
—(CH$_2$)$_m$—S—(CH$_2$)$_n$—O—(CH$_2$)$_p$—, and
—(CH$_2$)$_m$—S—(CH$_2$)$_n$—NR$^4$—(CH$_2$)$_p$—;
wherein any methylene (CH$_2$) carbon atom in Y, other than in R$^4$, can be substituted by one or two R$^3$ substituents;
Z is a 6–11 membered aromatic or nonaromatic mono- or polycyclic ring system having 0 to 6 heteroatoms selected from the group consisting of N, O, and S, and wherein the ring system is either unsubstituted or substituted with 0, 1, 2, 3 or 4 oxo or thio substituents, and either unsubstituted or substituted with one or more substituents independently selected from the group consisting of R$^{10}$, R$^{11}$, R$^{12}$ and R$^{13}$, provided that Z is not phenyl or pyridyl;
R$^1$ and R$^2$ are each independently selected from the group consisting of
  hydrogen, halogen, C$_{1-10}$ alkyl, C$_{3-8}$ cycloalkyl, C$_{3-8}$ cycloheteroalkyl, C$_{3-8}$ cycloalkyl C$_{1-6}$ alkyl, C$_{3-8}$ cycloheteroalkyl C$_{1-6}$ alkyl, aryl, aryl C$_{1-8}$ alkyl, amino, amino C$_{1-8}$ alkyl, C$_{1-3}$ acylamino, C$_{1-3}$ acylamino C$_{1-8}$ alkyl, (C$_{1-6}$ alkyl)$_p$amino, (C$_{1-6}$ alkyl)$_p$ amino C$_{1-8}$ alkyl, C$_{1-4}$ alkoxy, C$_{1-4}$ alkoxy C$_{1-6}$ alkyl, hydroxycarbonyl, hydroxycarbonyl C$_{1-6}$ alkyl, C$_{1-3}$ alkoxycarbonyl, C$_{1-3}$ alkoxycarbonyl C$_{1-6}$ alkyl, hydroxycarbonyl-C$_{1-6}$ alkyloxy, hydroxy, hydroxy C$_{1-6}$ alkyl, C$_{1-6}$ alkyloxy-C$_{1-6}$ alkyl, nitro, cyano, trifluoromethyl, trifluoromethoxy, trifluoroethoxy, C$_{1-8}$ alkyl-S(O)$_p$, (C$_{1-8}$ alkyl)$_p$aminocarbonyl, C$_{1-8}$ alkyloxycarbonylamino, (C$_{1-8}$ alkyl)$_p$ aminocarbonyloxy, (aryl C$_{1-8}$ alkyl)$_p$amino, (aryl)$_p$ amino, aryl C$_{1-8}$ alkylsulfonylamino, and C$_{1-8}$ alkylsulfonylamino;
  or two R$^1$ substituents, when on the same carbon atom, are taken together with the carbon atom to which they are attached to form a carbonyl group;
each R$^3$ is independently selected from the group consisting of
  hydrogen,
  aryl,
  C$_{1-10}$ alkyl,
  aryl-(CH$_2$)$_r$—O—(CH$_2$)$_s$—,
  aryl-(CH$_2$)$_r$S(O)$_p$—(CH$_2$)$_s$—,
  aryl-(CH$_2$)$_r$—C(O)—(CH$_2$)$_s$—,
  aryl-(CH$_2$)$_r$—C(O)—N(R$^4$)—(CH$_2$)$_s$—,
  aryl-(CH$_2$)$_r$—N(R$^4$)—C(O)—(CH$_2$)$_s$—,
  aryl-(CH$_2$)$_r$—N(R$^4$)—(CH$_2$)$_s$—,
  halogen,
  hydroxyl,
  oxo,
  trifluoromethyl,
  C$_{1-8}$ alkylcarbonylamino,
  aryl C$_{1-5}$ alkoxy,
  C$_{1-5}$ alkoxycarbonyl,
  (C$_{1-8}$ alkyl)$_p$aminocarbonyl,
  C$_{1-6}$ alkylcarbonyloxy,
  C$_{3-8}$ cycloalkyl,
  (C$_{1-6}$ alkyl)$_p$amino,
  amino C$_{1-6}$ alkyl,
  arylaminocarbonyl,
  aryl C$_{1-5}$ alkylaminocarbonyl,
  aminocarbonyl,
  aminocarbonyl C$_{1-6}$ alkyl,
  hydroxycarbonyl,
  hydroxycarbonyl C$_{1-6}$ alkyl,
  HC≡C—(CH$_2$)$_t$—,
  C$_{1-6}$ alkyl-C≡C—(CH$_2$)$_t$—,
  C$_{3-7}$ cycloalkyl-C≡C—(CH$_2$)$_t$—,
  aryl-C≡C—(CH$_2$)$_t$—,
  C$_{1-6}$ alkylaryl-C≡C—(CH$_2$)$_t$—,
  CH$_2$=CH—(CH$_2$)$_t$—,
  C$_{1-6}$ alkyl-CH=CH—(CH$_2$)$_t$—,
  C$_{3-7}$ cycloalkyl-CH=CH—(CH$_2$)$_t$—,
  aryl-CH=CH—(CH$_2$)$_t$—,
  C$_{1-6}$ alkylaryl-CH=CH—(CH$_2$)$_t$—,
  C$_{1-6}$ alkyl-SO$_2$—(CH$_2$)$_t$—,
  C$_{1-6}$ alkylaryl-SO$_2$—(CH$_2$)$_t$—,
  C$_{1-6}$ alkoxy,
  aryl C$_{1-6}$ alkoxy,
  aryl C$_{1-6}$ alkyl,
  (C$_{1-6}$ alkyl)$_p$amino C$_{1-6}$ alkyl,
  (aryl)$_p$amino,
  (aryl)$_p$amino C$_{1-6}$ alkyl,
  (aryl C$_{1-6}$ alkyl)$_p$amino,
  (aryl C$_{1-6}$ alkyl)$_p$amino C$_{1-6}$ alkyl,
  arylcarbonyloxy,
  aryl C$_{1-6}$ alkylcarbonyloxy,
  (C$_{1-6}$ alkyl)$_p$aminocarbonyloxy,
  C$_{1-8}$ alkylsulfonylamino,
  arylsulfonylamino,
  C$_{1-8}$ alkylsulfonylamino C$_{1-6}$ alkyl,
  arylsulfonylamino C$_{1-6}$ alkyl,
  aryl C$_{1-6}$ alkylsulfonylamino,
  aryl C$_{1-6}$ alkylsulfonylamino C$_{1-6}$ alkyl,
  C$_{1-8}$ alkoxycarbonylamino,
  C$_{1-8}$ alkoxycarbonylamino C$_{1-8}$ alkyl,
  aryloxycarbonylamino C$_{1-8}$ alkyl,
  aryl C$_{1-8}$ alkoxycarbonylamino,
  aryl C$_{1-8}$ alkoxycarbonylamino C$_{1-8}$ alkyl,
  C$_{1-8}$ alkylcarbonylamino,
  C$_{1-8}$ alkylcarbonylamino C$_{1-6}$ alkyl,
  arylcarbonylamino C$_{1-6}$ alkyl,
  aryl C$_{1-6}$ alkylcarbonylamino,
  aryl C$_{1-6}$ alkylcarbonylamino C$_{1-6}$ alkyl,
  aminocarbonylamino C$_{1-6}$ alkyl,
  (C$_{1-8}$ alkyl)$_p$aminocarbonylamino,
  (C$_{1-8}$ alkyl)$_p$aminocarbonylamino C$_{1-6}$ alkyl,
  (aryl)$_p$aminocarbonylamino C$_{1-6}$ alkyl,
  (aryl C$_{1-8}$ alkyl)$_p$aminocarbonylamino,
  (aryl C$_{1-8}$ alkyl)$_p$aminocarbonylamino C$_{1-6}$ alkyl,
  aminosulfonylamino C$_{1-6}$ alkyl,
  (C$_{1-8}$ alkyl)$_p$aminosulfonylamino, ($C_{1-8}$ alkyl)$_p$aminosulfonylamino $C_{1-6}$ alkyl,
(aryl)$_p$aminosulfonylamino $C_{1-6}$ alkyl,
(aryl $C_{1-8}$ alkyl)$_p$aminosulfonylamino,
(aryl $C_{1-8}$ alkyl)$_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
($C_{1-8}$ alkyl)$_p$aminocarbonyl $C_{1-6}$ alkyl,
(aryl)$_p$aminocarbonyl $C_{1-6}$ alkyl,
(aryl $C_{1-8}$ alkyl)$_p$aminocarbonyl, and
(aryl $C_{1-8}$ alkyl)$_p$aminocarbonyl $C_{1-6}$ alkyl;
  or two $R^3$ substituents, when on the same carbon atom are taken together with the carbon atom to which they are attached to form a carbonyl group or a cyclopropyl group,
wherein any of the alkyl groups of $R^3$ are either unsubstituted or substituted with one to three $R^1$ substituents, and provided that each $R^3$ is selected such that in the resultant compound the carbon atom or atoms to which $R^3$ is attached is itself attached to no more than one heteroatom;
each $R^4$ is independently selected from the group consisting of
  hydrogen,
  aryl,
  aminocarbonyl,
  $C_{3-8}$ cycloalkyl,
  amino $C_{1-6}$ alkyl,
  (aryl)$_p$aminocarbonyl,
  (aryl $C_{1-5}$ alkyl)$_p$aminocarbonyl,
  hydroxycarbonyl $C_{1-6}$ alkyl,
  $C_{1-8}$ alkyl,
  aryl $C_{1-6}$ alkyl,
  ($C_{1-6}$ alkyl)$_p$amino $C_{2-6}$ alkyl,
  (aryl $C_{1-6}$ alkyl)$_p$amino $C_{2-6}$ alkyl,
  $C_{1-8}$ alkylsulfonyl,
  $C_{1-8}$ alkoxycarbonyl,
  aryloxycarbonyl,
  aryl $C_{1-8}$ alkoxycarbonyl,
  $C_{1-8}$ alkylcarbonyl,
  arylcarbonyl,
  aryl $C_{1-6}$ alkylcarbonyl,
  ($C_{1-8}$ alkyl)$_p$aminocarbonyl,
  aminosulfonyl,
  $C_{1-8}$ alkylaminosulfonyl,
  (aryl)$_p$aminosulfonyl,
  (aryl $C_{1-8}$ alkyl)$_p$aminosulfonyl,
  arylsulfonyl,
  aryl$C_{1-6}$ alkylsulfonyl,
  $C_{1-6}$ alkylthiocarbonyl,
  arylthiocarbonyl, and
  aryl $C_{1-6}$ alkylthiocarbonyl,
wherein any of the alkyl groups of $R^4$ are either unsubstituted or substituted with one to three $R^1$ substituents;
$R^5$ and $R^6$ are each independently selected from the group consisting of
  hydrogen,
  $C_{1-10}$ alkyl,
  aryl,
  aryl-$(CH_2)_r$—O—$(CH_2)_s$—,
  aryl-$(CH_2)_r$S(O)$_p$—$(CH_2)_s$—,
  aryl-$(CH_2)_r$—C(O)—$(CH_2)_s$—,
  aryl-$(CH_2)_r$—C(O)—N($R^4$)—$(CH_2)_s$—,
  aryl-$(CH_2)_r$—N($R^4$)—C(O)—$(CH_2)_s$—,
  aryl-$(CH_2)_r$N($R^4$)—$(CH_2)_s$—,
  halogen,
  hydroxyl,
  $C_{1-8}$ alkylcarbonylamino,
  aryl $C_{1-5}$ alkoxy,
  $C_{1-5}$ alkoxycarbonyl,
  ($C_{1-8}$ alkyl)$_p$aminocarbonyl,
  $C_{1-6}$ alkylcarbonyloxy,
  $C_{3-8}$ cycloalkyl,
  ($C_{1-6}$ alkyl)$_p$amino,
  amino $C_{1-6}$ alkyl,
  arylaminocarbonyl,
  aryl $C_{1-5}$ alkylaminocarbonyl,
  aminocarbonyl,
  aminocarbonyl $C_{1-6}$ alkyl,
  hydroxycarbonyl,
  hydroxycarbonyl $C_{1-6}$ alkyl,
  HC≡C—$(CH_2)_t$—,
  $C_{1-6}$ alkyl-C≡C—$(CH_2)_t$—,
  $C_{3-7}$ cycloalkyl-C≡C—$(CH_2)_t$—,
  aryl-C≡C—$(CH_2)_t$—,
  $C_{1-6}$ alkylaryl-C≡C—$(CH_2)_t$—,
  $CH_2$=CH—$(CH_2)_t$—,
  $C_{1-6}$ alkyl-CH=CH—$(CH_2)_t$—,
  $C_{3-7}$ cycloalkyl-CH=CH—$(CH_2)_t$—,
  aryl-CH=CH—$(CH_2)_t$—,
  $C_{1-6}$ alkylaryl-CH=CH—$(CH_2)_t$—,
  $C_{1-6}$ alkyl-$SO_2$—$(CH_2)_t$—,
  $C_{1-6}$ alkylaryl-$SO_2$—$(CH_2)_t$—,
  $C_{1-6}$ alkoxy,
  aryl $C_{1-6}$ alkoxy,
  aryl $C_{1-6}$ alkyl,
  ($C_{1-6}$ alkyl)$_p$amino $C_{1-6}$ alkyl,
  (aryl)$_p$amino,
  (aryl)$_p$amino $C_{1-6}$ alkyl,
  (aryl $C_{1-6}$ alkyl)$_p$amino,
  (aryl $C_{1-6}$ alkyl)$_p$amino $C_{1-6}$ alkyl,
  arylcarbonyloxy,
  aryl $C_{1-6}$ alkylcarbonyloxy,
  ($C_{1-6}$ alkyl)$_p$aminocarbonyloxy, $C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$-alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl$)_p$aminocarbonyl $C_{1-6}$ alkyl,
(aryl $C_{1-8}$ alkyl$)_p$aminocarbonyl, and
(aryl $C_{1-8}$ alkyl$)_p$aminocarbonyl $C_{1-6}$ alkyl;
or $R^5$ and $R^6$ are taken together with the carbon atom to which they are attached to form a carbonyl group,
wherein any of the alkyl groups of $R^5$ or $R^6$ are either unsubstituted or substituted with one to three $R^1$ substituents, and provided that each $R^5$ and $R^6$ are selected such that in the resultant compound the carbon atom to which $R^5$ and $R^6$ are attached is itself attached to no more than one heteroatom;

$R^7$ and $R^8$ are each independently selected from the group consisting of
hydrogen,
$C_{1-10}$ alkyl,
aryl,
aryl-$(CH_2)_r$—O—$(CH_2)_s$—,
aryl-$(CH_2)_r$S(O)$_p$—$(CH_2)_s$—,
aryl-$(CH_2)_r$—C(O)—$(CH_2)_s$—,
aryl-$(CH_2)_r$—C(O)—N($R^4$)—$(CH_2)_s$—,
aryl-$(CH_2)_r$—N($R^4$)—C(O)—$(CH_2)_s$—,
aryl-$(CH_2)_r$—N($R^4$)—$(CH_2)_s$—,
halogen,
hydroxyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl-C≡C—$(CH_2)_t$—,
$C_{3-7}$ cycloalkyl-C≡C—$(CH_2)_t$—,
aryl-C≡C—$(CH_2)_t$—,
$C_{1-6}$ alkylaryl-C≡C—$(CH_2)_t$—,
$CH_2$=CH—$(CH_2)_t$—,
$C_{1-6}$ alkyl-CH=CH—$(CH_2)_t$—,
$C_{3-7}$ cycloalkyl-CH=CH—$(CH_2)_t$—,
aryl-CH=CH—$(CH_2)_t$—,
$C_{1-6}$ alkylaryl-CH=CH—$(CH_2)_t$—,
$C_{1-6}$ alkyl-$SO_2$—$(CH_2)_t$—,
$C_{1-6}$ alkylaryl-$SO_2$—$(CH_2)_t$—,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
(aryl$)_p$amino,
(aryl$)_p$amino $C_{1-6}$ alkyl,
(aryl $C_{1-6}$ alkyl$)_p$amino,
(aryl $C_{1-6}$ alkyl$)_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylcarbonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl, aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
arylaminocarbonylamino,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl$)_p$aminocarbonyl $C_{1-6}$ alkyl,
(aryl $C_{1-8}$ alkyl$)_p$aminocarbonyl,
(aryl $C_{1-8}$ alkyl$)_p$aminocarbonyl $C_{1-6}$ alkyl, and
$C_{7-20}$ polycyclyl $C_{0-8}$ alkylsulfonylamino,
wherein any of the alkyl groups of $R^7$ and $R^8$ are either unsubstituted or substituted with one to three $R^1$ substituents, and provided that each $R^7$ and $R^8$ are selected such that in the resultant compound the carbon atom to which $R^7$ and $R^8$ are attached is itself attached to no more than one heteroatom;
$R^9$ is selected from the group consisting of
hydrogen,
$C_{1-8}$ alkyl,
aryl,
aryl $C_{1-8}$ alkyl,
$C_{1-8}$ alkylcarbonyloxy $C_{1-4}$ alkyl,
aryl $C_{1-8}$ alkylcarbonyloxy $C_{1-4}$ alkyl,
$C_{1-8}$ alkylaminocarbonylmethylene, and
$C_{1-8}$ dialkylaminocarbonylmethylene; $R^{10}$, $R^{11}$, $R^{12}$, and $R^{13}$ are each independently selected from the group consisting of
hydrogen,
$C_{1-8}$ alkyl,
aryl,
halogen,
hydroxyl,
oxo,
aminocarbonyl,
$C_{3-8}$ cycloalkyl,
amino $C_{1-6}$ alkyl,
(aryl$)_p$aminocarbonyl,
hydroxycarbonyl,
(aryl $C_{1-5}$ alkyl$)_p$aminocarbonyl,
hydroxycarbonyl $C_{1-6}$ alkyl,
aryl $C_{1-6}$ alkyl,
$(C_{1-6}$ alkyl$)_p$amino $C_{1-6}$ alkyl,
(aryl $C_{1-6}$ alkyl$)_p$amino $C_{2-6}$ alkyl,
$C_{1-8}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
$(C_{1-8}$ alkyl$)_p$aminocarbonyl,
aminosulfonyl,
$C_{1-8}$ alkylaminosulfonyl,
(aryl$)_p$aminosulfonyl,
(aryl $C_{1-8}$ alkyl$)_p$aminosulfonyl,
$C_{1-6}$ alkylsulfonyl,
arylsulfonyl,
aryl $C_{1-6}$ alkylsulfonyl,
aryl $C_{1-6}$ alkylcarbonyl,
$C_{1-6}$ alkylthiocarbonyl,
arylthiocarbonyl,
aryl $C_{1-6}$ alkylthiocarbonyl,
aryl-$(CH_2)_r$—O—$(CH_2)_s$—,
aryl-$(CH_2)_r$S(O)$_p$—$(CH_2)_s$—,
aryl-$(CH_2)_r$—C(O)—$(CH_2)_s$—,
aryl-$(CH_2)_r$—C(O)—N($R^4$)—$(CH_2)_s$—,
aryl-$(CH_2)_r$—N($R^4$)—C(O)—$(CH_2)_s$—,
aryl-$(CH_2)_r$—N($R^4$)—$(CH_2)_s$—),
HC≡C—$(CH_2)_t$—,
$C_{1-6}$ alkyl-C≡C—$(CH_2)_t$—,
$C_{3-7}$ cycloalkyl-C≡C—$(CH_2)_t$—,
aryl-C≡C—$(CH_2)_t$—,
$C_{1-6}$ alkylaryl-C≡C—$(CH_2)_t$—,
$CH_2$=CH—$(CH_2)_t$—,
$C_{1-6}$ alkyl-CH=CH—$(CH_2)_t$—,
$C_{3-7}$ cycloalkyl-CH=CH—$(CH_2)_t$—,
aryl-CH=CH—$(CH_2)_t$—,
$C_{1-6}$ alkylaryl-CH=CH—$(CH_2)_t$—,
$C_{1-6}$ alkyl-$SO_2$—$(CH_2)_t$—,
$C_{1-6}$ alkylaryl-$SO_2$—$(CH_2)_t$—,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl, C$_{1-6}$ alkylcarbonyloxy,
(C$_{1-6}$ alkyl)$_p$amino,
aminocarbonyl C$_{1-6}$ alkyl,
C$_{1-6}$ alkoxy,
aryl C$_{1-6}$ alkoxy,
(aryl)$_p$amino,
(aryl)$_p$amino C$_{1-6}$ alkyl,
(aryl C$_{1-6}$ alkyl)$_p$amino,
(aryl C$_{1-6}$ alkyl)$_p$amino C$_{1-6}$ alkyl,
arylcarbonyloxy,
aryl C$_{1-6}$ alkylcarbonyloxy,
(C$_{1-6}$ alkyl)$_p$aminocarbonyloxy,
C$_{1-8}$ alkylsulfonylamino,
arylsulfonylamino,
C$_{1-8}$ alkylsulfonylamino C$_{1-6}$ alkyl,
arylsulfonylamino C$_{1-6}$ alkyl,
aryl C$_{1-6}$ alkylsulfonylamino,
aryl C$_{1-6}$ alkylsulfonylamino C$_{1-6}$ alkyl,
C$_{1-8}$ alkoxycarbonylamino,
C$_{1-8}$ alkoxycarbonylamino C$_{1-8}$ alkyl,
aryloxycarbonylamino C$_{1-8}$ alkyl,
aryl C$_{1-8}$ alkoxycarbonylamino,
aryl C$_{1-8}$ alkoxycarbonylamino C$_{1-8}$ alkyl,
C$_{1-8}$ alkylcarbonylamino,
C$_{1-8}$ alkylcarbonylamino C$_{1-6}$ alkyl,
arylcarbonylamino C$_{1-6}$ alkyl,
aryl C$_{1-6}$ alkylcarbonylamino,
aryl C$_{1-6}$ alkylcarbonylamino C$_{1-6}$ alkyl,
aminocarbonylamino C$_{1-6}$ alkyl,
(C$_{1-8}$ alkyl)$_p$aminocarbonylamino,
(C$_{1-8}$ alkyl)$_p$aminocarbonylamino C$_{1-6}$ alkyl,
(aryl)$_p$aminocarbonylamino C$_{1-6}$ alkyl,
(aryl C$_{1-8}$ alkyl)$_p$aminocarbonylamino,
(aryl C$_{1-8}$ alkyl)$_p$aminocarbonylamino C$_{1-6}$ alkyl,
aminosulfonylamino C$_{1-6}$ alkyl,
(C$_{1-8}$ alkyl)$_p$aminosulfonylamino,
(C$_{1-8}$ alkyl)$_p$aminosulfonylamino C$_{1-6}$ alkyl,
(aryl)$_p$aminosulfonylamino C$_{1-6}$ alkyl,
(aryl C$_{1-8}$ alkyl)$_p$aminosulfonylamino,
(aryl C$_{1-8}$ alkyl)$_p$aminosulfonylamino C$_{1-6}$ alkyl,
C$_{1-6}$ alkylsulfonyl,
C$_{1-6}$ alkylsulfonyl C$_{1-6}$ alkyl,
arylsulfonyl C$_{1-6}$ alkyl,
aryl C$_{1-6}$ alkylsulfonyl,
aryl C$_{1-6}$ alkylsulfonyl C$_{1-6}$ alkyl,
C$_{1-6}$ alkylcarbonyl,
C$_{1-6}$ alkylcarbonyl C$_{1-6}$ alkyl,
arylcarbonyl C$_{1-6}$ alkyl,
aryl C$_{1-6}$ alkylcarbonyl,
aryl C$_{1-6}$ alkylcarbonyl C$_{1-6}$ alkyl,
C$_{1-6}$ alkylthiocarbonylamino,
C$_{1-6}$ alkylthiocarbonylamino C$_{1-6}$ alkyl,
arylthiocarbonylamino C$_{1-6}$ alkyl,
aryl C$_{1-6}$ alkylthiocarbonylamino,
aryl C$_{1-6}$ alkylthiocarbonylamino C$_{1-6}$ alkyl,
(C$_{1-8}$ alkyl)$_p$aminocarbonyl C$_{1-6}$ alkyl,
(aryl)$_p$aminocarbonyl C$_{1-6}$ alkyl,
(aryl C$_{1-8}$ alkyl)$_p$aminocarbonyl, and
(aryl C$_{1-8}$ alkyl)$_p$aminocarbonyl C$_{1-6}$ alkyl, wherein any of the alkyl groups of $R^{10}$, $R^{11}$, $R^{12}$, and $R^{13}$ are either unsubstituted or substituted with one to three $R^1$ substituents;

wherein each m is independently an integer from 0 to 6;
each n is independently an integer from 0 to 6;
each p is independently an integer from 0 to 2;
each r is independently an integer from 1 to 3;
each s is independently an integer from 0 to 3;
each t is an integer from 0 to 3; and
v is independently an integer from 0 to 6;

and the pharmaceutically acceptable salts thereof.

In the compounds of the present invention, W is preferably a 6-membered monocyclic aromatic or nonaromatic ring system having 1 or 2 nitrogen atoms wherein each carbon atom is either unsubstituted or substituted with one $R^1$ substituent, or a 9- to 14-membered polycyclic ring system, wherein one or more of the rings is aromatic, and wherein the polycyclic ring system has 0, 1, 2, 3 or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents.

More preferably, W is selected from the group consisting of

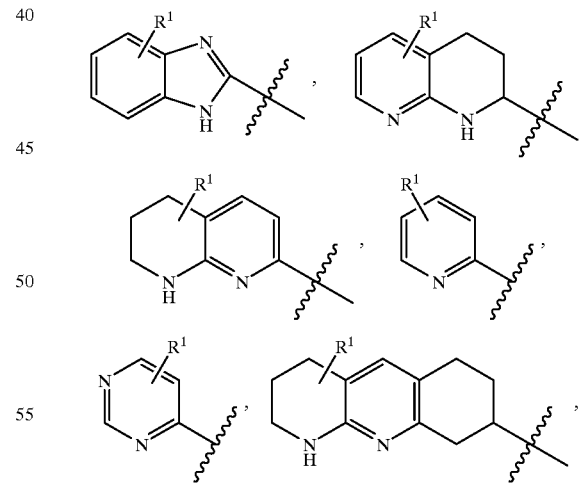

and

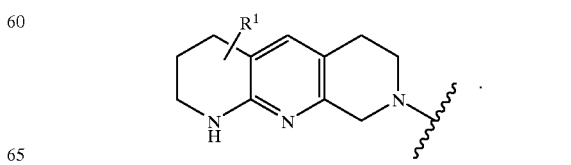

Most preferably W is

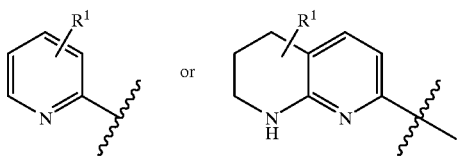

In the compounds of the present invention, X is preferably —$(CH_2)_v$—, wherein any methylene ($CH_2$) carbon atom is either unsubstituted or substituted with one or two $R^1$ substituents.

More preferably X is a direct bond, that is, v is 0.

In the compounds of the present invention, Y is preferably selected from the group consisting of —$(CH_2)_m$—,
—$(CH_2)_m$—O—$(CH_2)_n$—,
—$(CH_2)_m$—$NR^4$—$(CH_2)_n$—,
—$(CH_2)_m$—S—$(CH_2)_n$—,
—$(CH_2)_m$—SO—$(CH_2)_n$—,
—$(CH_2)_m$—$SO_2$—$(CH_2)_n$—,
—(CH2)m—O—(CH2)n—O—(CH2)p—,
—$(CH_2)$m—O—(CH2)n—$NR^4$—(CH2)p—,
—$(CH_2)$m—$NR^4$—(CH2)n—$NR^4$—(CH2)p—, and
—$(CH_2)$m—$NR^4$—(CH2)n—O—(CH2)p—, wherein any methylene ($CH_2$) carbon atom in Y, other than in $R^4$, can be substituted by one or two $R^3$ substituents.

More preferably Y is selected from the group consisting of $(CH_2)_m$, $(CH_2)_m$—S—$(CH_2)_n$, and $(CH_2)_m$—$NR^4$—$(CH_2)_n$, wherein any methylene ($CH_2$) carbon atom in Y, other than in $R^4$, can be substituted by one or two $R^3$ substituents.

In the compounds of the present invention, Z is preferably selected from the group consisting of

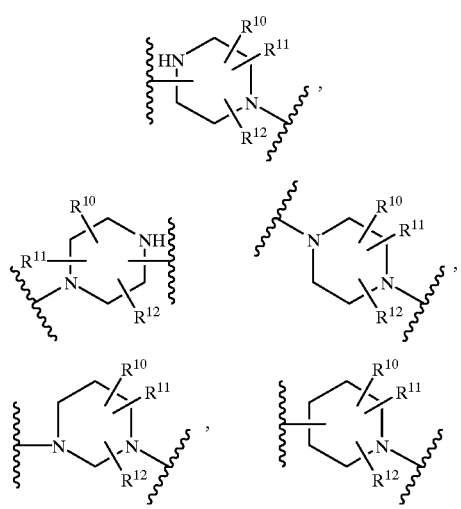

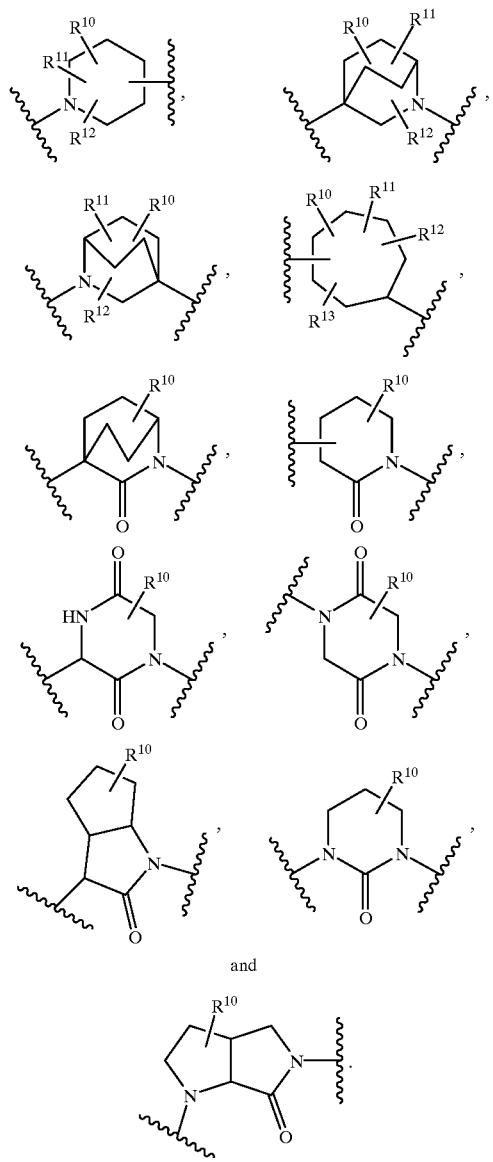

More preferably Z is selected from the group consisting of

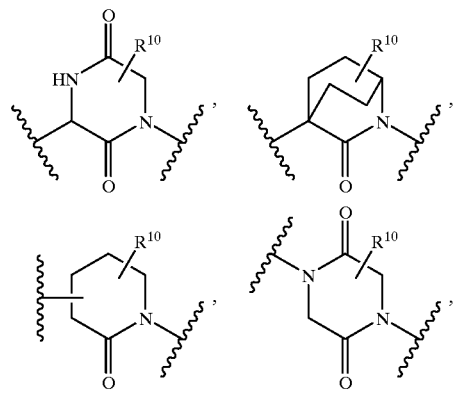

and

-continued

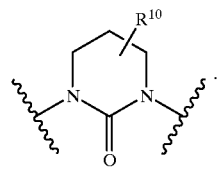

Most preferably Z is

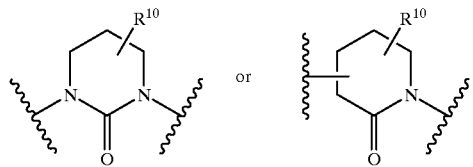

In the compounds of the present invention, $R^1$ and $R^2$ are preferably selected from the group consisting of hydrogen, halogen, $C_{1-10}$ alkyl, $C_{3-8}$ cycloalkyl, $C_{3-8}$ cycloheteroalkyl, hydroxy, nitro, cyano, trifluoromethyl, and trifluoromethoxy.

More preferably, $R^1$ and $R^2$ are selected from the group consisting of hydrogen, halogen, $C_{1-10}$ alkyl, $C_{3-8}$ cycloalkyl, trifluoromethyl, and trifluoromethoxy.

In the compounds of the present invention, $R^3$ is preferably selected from the group consisting of hydrogen,
fluoro,
trifluoromethyl,
aryl,
$C_{1-8}$ alkyl,
aryl$C_{1-6}$ alkyl
hydroxyl,
oxo,
arylaminocarbonyl,
aryl $C_{1-5}$ alkylaminocarbonyl,
aminocarbonyl, and
aminocarbonyl $C_{1-6}$ alkyl.

More preferably, $R^3$ is selected from the group consisting of fluoro,
aryl,
$C_{1-8}$ alkyl,
aryl$C_{1-6}$ alkyl
hydroxyl,
oxo, and
arylaminocarbonyl.

In the compounds of the present invention, $R^4$ is preferably selected from the group consisting of hydrogen,
aryl,
$C_{3-8}$ cycloalkyl,
$C_{1-8}$ alkyl,
$C_{1-8}$ alkylcarbonyl,
arylcarbonyl,
$C_{1-6}$ alkylsulfonyl,
arylsulfonyl,
aryl$C_{1-6}$alkylsulfonyl,
aryl$C_{1-6}$alkylcarbonyl,
$C_{1-8}$-alkylaminocarbonyl,
aryl$C_{1-5}$alkylaminocarbonyl,
aryl$C_{1-8}$alkoxycarbonyl, and
$C_{1-8}$alkoxycarbonyl.

More preferably, $R^4$ is selected from the group consisting of hydrogen,
$C_{1-8}$ alkyl,
$C_{1-8}$ alkylcarbonyl,
arylcarbonyl,
aryl$C_{1-6}$alkylcarbonyl,
$C_{1-6}$ alkylsulfonyl,
arylsulfonyl, and
aryl$C_{1-6}$alkylsulfonyl.

In one embodiment of the present invention, $R^5$ and $R^6$ are each independently selected from the group consisting of hydrogen,
aryl,
$C_{1-8}$ alkyl,
aryl-C≡C—(CH$_2$)$_t$—,
aryl $C_{1-6}$ alkyl,
CH$_2$=CH—(CH$_2$)$_t$—, and
HC≡C—(CH$_2$)$_t$—.

In a class of this embodiment of the present invention, $R^6$ is hydrogen and $R^5$ is selected from the group consisting of hydrogen,
aryl,
$C_{1-8}$ alkyl,
aryl-C≡C—(CH$_2$)$_t$—,
aryl $C_{1-6}$ alkyl,
CH$_2$=CH—(CH$_2$)$_t$—, and
HC≡C—(CH$_2$)$_t$—.

In a subclass of this class of the present invention, $R^6$, $R^7$, and $R^8$ are each hydrogen and $R^5$ is selected from the group consisting of hydrogen,
aryl,
$C_{1-8}$ alkyl,
aryl-C≡C—(CH$_2$)$_t$—,
aryl $C_{1-6}$ alkyl,
CH$_2$=CH—(CH$_2$)$_t$—, and
HC≡C—(CH$_2$)$_t$—.

In another embodiment of the present invention, $R^7$ and $R^8$ are each independently selected from the group consisting of hydrogen,
aryl,
$C_{1-8}$ alkylcarbonylamino,
arylcarbonylamino,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl, aryl $C_{1-8}$ alkoxycarbonylamino,
aryl $C_{1-8}$ alkoxycarbonylamino $C_{1-8}$ alkyl,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino, and
aryl $C_{1-6}$ alkylthiocarbonylamino $C_{1-6}$ alkyl.

In a class of this embodiment of the present invention, $R^8$ is hydrogen and $R^7$ is selected from the group consisting of consisting of
hydrogen,
aryl,
$C_{1-8}$ alkylcarbonylamino,
aryl $C_{1-6}$ alkylcarbonylamino,
arylcarbonylamino,
$C_{1-8}$ alkylsulfonylamino,
aryl $C_{1-6}$ alkylsulfonylamino,
arylsulfonylamino,
$C_{1-8}$ alkoxycarbonylamino,
aryl $C_{1-8}$ alkoxycarbonylamino,
arylaminocarbonylamino,
$(C_{1-8}$ alkyl$)_p$aminocarbonylamino,
(aryl $C_{1-8}$ alkyl$)_p$aminocarbonylamino,
$(C_{1-8}$ alkyl$)_p$aminosulfonylamino, and
(aryl $C_{1-8}$ alkyl$)_p$aminosulfonylamino.

In a subclass of this class of the present invention, $R^5$, $R^6$, and $R^8$ are each hydrogen and $R^7$ is selected from the group consisting of
hydrogen,
aryl,
$C_{1-8}$ alkylcarbonylamino,
aryl $C_{1-6}$ alkylcarbonylamino,
arylcarbonylamino,
$C_{1-8}$ alkylsulfonylamino,
aryl $C_{1-6}$ alkylsulfonylamino,
arylsulfonylamino,
$C_{1-8}$ alkoxycarbonylamino,
aryl $C_{1-8}$ alkoxycarbonylamino,
arylaminocarbonylamino,
$(C_{1-8}$ alkyl$)_p$aminocarbonylamino,
(aryl $C_{1-8}$ alkyl$)_p$aminocarbonylamino,
$(C_{1-8}$ alkyl$)_p$aminosulfonylamino, and
(aryl $C_{1-8}$ alkyl$)_p$aminosulfonylamino.

In the compounds of the present invention, $R^9$ is preferably selected from the group consisting of hydrogen, methyl, and ethyl.

More preferably, $R^9$ is hydrogen.

In the compounds of the present invention, $R^{10}$, $R^{11}$, $R^{12}$, and $R^{13}$ are preferably each independently selected from the group consisting of hydrogen and $C_{1-8}$ alkyl.

More preferably $R^{10}$, $R^{11}$, $R^{12}$, and $R^{13}$ are hydrogen.

In the compounds of the present invention, m is preferably an integer from 0 to 4, more preferably from 0 to 3.

In the compounds of the present invention, n is preferably an integer from 0 to 4, more preferably from 0 to 3.

In the compounds of the present invention, r is preferably an integer from 1 to 2.

In the compounds of the present invention, s is preferably an integer from 0 to 2.

In the compounds of the present invention, t is preferably an integer from 0 to 2, more preferably from 0 to 1.

In the compounds of the present invention, v is preferably 0.

In certain embodiments of the present invention the compounds have the formula with the following designated stereochemistry:

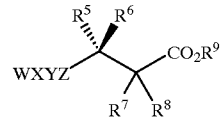

wherein the substituents W, X, Y, Z, $R^1$, $R^2$, $R^3$, $R^4$, $R^5$, $R^6$, $R^7$, $R^8$, $R^9$, $R^{10}$, $R^{11}$, $R^{12}$, and $R^{13}$, and the subscripts m, n, p, r, s, t, and v are as described above.

Illustrative but nonlimiting examples of compounds of the present invention that are useful as integrin receptor antagonists are the following:

ethyl 3(S)-(2,3-dihydro-benzofuran-6-yl)-3-{2-oxo-3-[3-(5,6,7,8-tetrahydro-[1,8]naphthyridin-2-yl)-propyl]-tetrahydro-pyrimidin-1-yl}-propionate;

ethyl 3(S)-(3-fluorophenyl)-3-(2-oxo-3(S or R)-[3-(5,6,7,8-tetrahydro-[1,8]naphthyridin-2-yl)-propyl]-piperidin-1-yl)-propionate;

ethyl 3(S)-(3-fluorophenyl)-3-(2-oxo-3(R or S)-[3-(5,6,7,8-tetrahydro-[1,8]naphthyridin-2-yl)-propyl]-piperidin-1-yl)-propionate;

3(S)-(2,3-dihydro-benzofuran-6-yl)-3-{2-oxo-3-[3-(5,6,7,8-tetrahydro-[1,8]naphthyridin-2-yl)-propyl]-tetrahydro-pyrimidin-1-yl}-propionic acid;

3(S)-(3-fluorophenyl)-3-(2-oxo-3(S or R)-[3-(5,6,7,8-tetrahydro-[1,8]naphthyridin-2-yl)-propyl]-piperidin-1-yl)-propionic acid;

3(S)-(3-fluorophenyl)-3-(2-oxo-3(R or S)-[3-(5,6,7,8-tetrahydro-[1,8]naphthyridin-2-yl)-propyl]-piperidin-1-yl)-propionic acid;

and the pharmaceutically acceptable salts thereof.

Further illustrative of the present invention are the compounds selected from the group consisting of:

3(S)-(2,3-dihydro-benzofuran-6-yl)-3-{2-oxo-3-[3-(5,6,7,8-tetrahydro-[1,8]naphthyridin-2-yl)-propyl]-tetrahydro-pyrimidin-1-yl}-propionic acid;

3(S)-(3-fluorophenyl)-3-(2-oxo-3(S or R)-[3-(5,6,7,8-tetrahydro-[1,8]naphthyridin-2-yl)-propyl]-piperidin-1-yl)-propionic acid;

3(S)-(3-fluorophenyl)-3-(2-oxo-3(R or S)-[3-(5,6,7,8-tetrahydro-[1,8]naphthyridin-2-yl)-propyl]-piperidin-1-yl)-propionic acid;
and the pharmaceutically acceptable salts thereof.

For use in medicine, the salts of the compounds of this invention refer to non-toxic "pharmaceutically acceptable salts." Other salts may, however, be useful in the preparation of the compounds according to the invention or of their pharmaceutically acceptable salts. Salts encompassed within the term "pharmaceutically acceptable salts" refer to non-toxic salts of the compounds of this invention which are generally prepared by reacting the free base with a suitable organic or inorganic acid. Representative salts include the following: acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

The compounds of the present invention can have chiral centers and occur as racemates, racemic mixtures, diastereomeric mixtures, and as individual diastereomers, or enantiomers with all isomeric forms being included in the present invention. Therefore, where a compound is chiral, the separate enantiomers or diastereomers, substantially free of the other, are included within the scope of the invention; further included are all mixtures of the two enantiomers. Also included within the scope of the invention are polymorphs and hydrates of the compounds of the instant invention.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

The term "therapeutically effective amount" shall mean that amount of a drug or pharmaceutical agent that will elicit the biological or medical response of a tissue, system, animal or human that is being sought by a researcher or clinician.

The term "integrin receptor antagonist," as used herein, refers to a compound which binds to and antagonizes either the αvβ3 receptor, the αvβ5 receptor, or the αvβ6 receptor, or a compound which binds to and antagonizes combinations of these receptors (for example, a dual αvβ3/αvβ5 receptor antagonist).

The term "bone resorption," as used herein, refers to the process by which osteoclasts degrade bone.

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.).

The term "alkenyl" shall mean straight or branched chain alkenes of two to ten total carbon atoms, or any number within this range.

The term "alkynyl" shall mean straight or branched chain alkynes of two to ten total carbon atoms, or any number within this range.

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

The term "cycloheteroalkyl," as used herein, shall mean a 3- to 8-membered fully saturated heterocyclic ring containing one or two heteroatoms chosen from N, O or S. Examples of cycloheteroalkyl groups include, but are not limited to piperidinyl, pyrrolidinyl, azetidinyl, morpholinyl, piperazinyl.

The term "alkoxy," as used herein, refers to straight or branched chain alkoxides of the number of carbon atoms specified (e.g., $C_{1-5}$ alkoxy), or any number within this range (i.e., methoxy, ethoxy, etc.).

The term "aryl," as used herein, refers to a monocyclic or polycyclic system comprising at least one aromatic ring, wherein the monocylic or polycyclic system contains 0, 1, 2, 3, or 4 heteroatoms chosen from N, O, or S, and wherein the monocylic or polycylic system is either unsubstituted or substituted with one or more groups independently selected from hydrogen, halogen, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino $C_{1-8}$ alkyl, $C_{1-6}$ dialkylamino, $C_{1-6}$ dialkylamino-$C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, oxo or $C_{1-5}$ alkylcarbonyloxy. Examples of aryl include, but are not limited to, phenyl, naphthyl, pyridyl, pyrazinyl, pyrimidinyl, imidazolyl, benzimidazolyl, benzthiazolyl, benzoxazolyl, indolyl, thienyl, furyl, pyrryl, pyrazolyl, dihydrobenzofuryl, benzo(1,3) dioxolane, oxazolyl, isoxazolyl and thiazolyl, which are either unsubstituted or substituted with one or more groups independently selected from hydrogen, halogen, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino-$C_{1-8}$ alkyl, $C_{1-6}$ dialkylamino, $C_{1-6}$ dialkylamino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, oxo or $C_{1-5}$ alkylcarbonyloxy. Preferably, the aryl group is unsubstituted, mono-, di-, tri- or tetra-substituted with one to four of the above-named substituents; more preferably, the aryl group is unsubstituted, mono-, di- or tri-substituted with one to three of the above-named substituents; most preferably, the aryl group is unsubstituted, mono- or di-substituted with one to two of the above-named substituents.

Whenever the term "alkyl" or "aryl" or either of their prefix roots appear in a name of a substituent (e.g., aryl $C_{0-8}$ alkyl) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The terms "arylalkyl" and "alkylaryl" include an alkyl portion where alkyl is as defined above and to include an aryl portion where aryl is as defined above. Examples of arylalkyl include, but are not limited to, benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include, but are not limited to, toluene, ethylbenzene, propylbenzene, methylpyridine, ethylpyridine, propylpyridine and butylpyridine.

In the compounds of the present invention, two $R^1$ substituents, when on the same carbon atom, can be taken together with the carbon to which they are attached to form a carbonyl group.

In the compounds of the present invention, two $R^3$ substituents, when on the same carbon atom, can be taken together with the carbon atom to which they are attached to form a carbonyl group. In such instances, the limitation, that in the resultant compound the carbon atom or atoms to which $R^3$ is attached is itself attached to no more than one heteroatom, does not apply. Also, in the compounds of the present invention, two $R^3$ substituents, when on the same carbon atom, can be taken together with the carbon atom to which they are attached to form a cyclopropyl group.

In the compounds of the present invention, $R^5$ and $R^6$ can be taken together with the carbon atom to which they are attached to form a carbonyl group. In such instances, the limitation, that in the resultant compound the carbon atom to which $R^5$ and $R^6$ is attached is itself attached to no more than one heteroatom, does not apply.

The term "halogen" shall include iodine, bromine, chlorine, and fluorine.

The term "oxy" means an oxygen (O) atom. The term "thio" means a sulfur (S) atom. The term "oxo" means "=O". The term "carbonyl" means "C=O."

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Under standard nonmenclature used throughout this disclosure, the terminal portion of the designated side chain is described first, followed by the adjacent functionality toward the point of attachment. For example, a $C_{1-5}$ alkyl-carbonylamino $C_{1-6}$ alkyl substituent is equivalent to

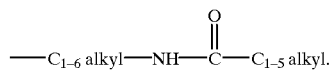

In choosing compounds of the present invention, one of ordinary skill in the art will recognize that the various substituents, i.e. W, X, Y, Z, $R^1$, $R^2$, $R^3$, $R^4$, $R^5$, $R^6$, $R^7$, $R^8$, $R^9$, $R^{10}$, $R^{11}$, $R^{12}$, and $R^{13}$, and the subscripts m, n, p, r, s, t, and v are to be chosen in conformity with well-known principles of chemical structure connectivity.

Representative compounds of the present invention typically display submicromolar affinity for the integrin receptors, particularly the $\alpha v\beta 3$, $\alpha v\beta 5$, and/or $\alpha v\beta 6$ receptors. Compounds of this invention are therefore useful for treating mammals suffering from a bone condition caused or mediated by increased bone resorption, who are in need of such therapy. Pharmacologically effective amounts of the compounds, including pharmaceutically acceptable salts thereof, are administered to the mammal, to inhibit the activity of mammalian osteoclasts.

The compounds of the present invention are administered in dosages effective to antagonize the $\alpha v\beta 3$ receptor where such treatment is needed, as, for example, in the prevention or treatment of osteoporosis.

Further exemplifying the invention is the method wherein the integrin receptor antagonizing effect is an $\alpha v\beta 3$ antagonizing effect. An illustration of the invention is the method wherein the $\alpha v\beta 3$ antagonizing effect is selected from inhibition of bone resorption, restenosis, angiogenesis, diabetic retinopathy, macular degeneration, inflammation, viral disease, tumor growth, or metastasis. Preferably, the $\alpha v\beta 3$ antagonizing effect is the inhibition of bone resorption.

An example of the invention is the method wherein the integrin receptor antagonizing effect is an $\alpha v\beta 5$ antagonizing effect. More specifically, the $\alpha v\beta 5$ antagonizing effect is selected from inhibition of restenosis, angiogenesis, diabetic retinopathy, macular degeneration, inflammation, tumor growth, or metastasis.

Illustrating the invention is the method wherein the integrin receptor antagonizing effect is a dual $\alpha v\beta 3/\alpha v\beta 5$ antagonizing effect. More particularly, the dual $\alpha v\beta 3/\alpha v\beta 5$ antagonizing effect is selected from inhibition of bone resorption, restenosis, angiogenesis, diabetic retinopathy, macular degeneration, inflammation, viral disease, tumor growth, or metastasis.

Illustrating the invention is the method wherein the integrin receptor antagonizing effect is an $\alpha v\beta 6$ antagonizing effect. More particularly, the $\alpha v\beta 6$ antagonizing effect is selected from inhibition of angiogenesis, inflammatory response, or wound healing.

Illustrating the invention is the method wherein the $\alpha v\beta 3$ antagonizing effect is selected from inhibition of bone resorption, inhibition of restenosis, inhibition of angiogenesis, inhibition of diabetic retinopathy, inhibition of macular degeneration, inhibition of atherosclerosis, inflammation, viral disease, or inhibition of tumor growth or metastasis. Preferably, the $\alpha v\beta 3$ antagonizing effect is the inhibition of bone resorption.

More particularly illustrating the invention is a pharmaceutical composition comprising any of the compounds described above and a pharmaceutically acceptable carrier. Another example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Further illustrating the invention is a method of treating and/or preventing a condition mediated by antagonism of an integrin receptor in a mammal in need thereof, comprising administering to the mammal a therapeutically effective amount of any of the compounds described above. Preferably, the condition is selected from bone resorption, osteoporosis, restenosis, diabetic retinopathy, macular degeneration, angiogenesis, atherosclerosis, inflammation, viral disease, cancer, tumor growth, and metastasis. More preferably, the condition is selected from osteoporosis and cancer. Most preferably, the condition is osteoporosis.

More specifically exemplifying the invention is a method of eliciting an integrin antagonizing effect in a mammal in need thereof, comprising administering to the mammal a therapeutically effective amount of any of the compounds or any of the pharmaceutical compositions described above. Preferably, the integrin antagonizing effect is an $\alpha v\beta 3$ antagonizing effect; more specifically, the $\alpha v\beta 3$ antagonizing effect is selected from inhibition of bone resorption, inhibition of restenosis, inhibition of atherosclerosis, inhibition of angiogenesis, inhibition of diabetic retinopathy, inhibition of macular degeneration, inhibition of inflammation, inhibition of viral disease, or inhibition of tumor growth or metastasis. Most preferably, the $\alpha v\beta 3$ antagonizing effect is inhibition of bone resorption. Alternatively, the integrin antagonizing effect is an $\alpha v\beta 5$ antagonizing effect, an $\alpha v\beta 6$ antagonizing effect, or a mixed $\alpha v\beta 3$, $\alpha v\beta 5$, and $\alpha v\beta 6$ antagonizing effect. Examples of $\alpha v\beta 5$ antagonizing effects are inhibition of restenosis, atherosclerosis, angiogenesis, diabetic retinopathy, macular degeneration, inflammation, viral disease, or tumor growth. Examples of dual $\alpha v\beta 6$ antagonizing effects are inhibition of angiogenesis, inflammatory response and wound healing.

Additional examples of the invention are methods of inhibiting bone resorption and of treating and/or preventing osteoporosis in a mammal in need thereof, comprising administering to the mammal a therapeutically effective amount of any of the compounds or any of the pharmaceutical compositions described above.

Additional illustrations of the invention are methods of treating hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid treatment in a mammal in need thereof, comprising administering to the mammal a therapeutically effective amount of any of the compounds or any of the pharmaceutical compositions described above.

More particularly exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of bone resorption, tumor growth, cancer, restenosis, atherosclerosis, diabetic retinopathy, macular degeneration, inflammation, viral disease, and/or angiogenesis.

Also exemplifying the invention are compositions further comprising an active ingredient selected from the group consisting of
  a.) an organic bisphosphonate or a pharmaceutically acceptable salt or ester thereof,
  b.) an estrogen receptor modulator,
  c.) a cytotoxic/antiproliferative agent,
  d.) a matrix metalloproteinase inhibitor,
  e.) an inhibitor of epidermal-derived, fibroblast-derived, or platelet-derived growth factors,
  f.) an inhibitor of VEGF,
  g.) an inhibitor of Flk-1/KDR, Flt-1, Tck/Tie-2, or Tie-1,
  h.) a cathepsin K inhibitor, and
  i.) a prenylation inhibitor, such as a farnesyl transferase inhibitor or a geranylgeranyl transferase inhibitor or a dual farnesyl/geranylgeranyl transferase inhibitor; and mixtures thereof.
(See, B. Millauer et al., "Dominant-Negative Inhibition of Flk-1 Suppresses the Growth of Many Tumor Types in Vivo", *Cancer Research*, 56, 1615–1620 (1996), which is incorporated by reference herein in its entirety).

Preferably, the active ingredient is selected from the group consisting of:
  a.) an organic bisphosphonate or a pharmaceutically acceptable salt or ester thereof,
  b.) an estrogen receptor modulator, and
  c.) a cathepsin K inhibitor, and mixtures thereof.

Nonlimiting examples of such bisphosphonates include alendronate, etidronate, pamidronate, risedronate, ibandronate, and pharmaceutically acceptable salts and esters thereof. A particularly preferred bisphosphonate is alendronate, especially alendronate monosodium trihydrate.

Nonlimiting examples of estrogen receptor modulators include estrogen, progesterin, estradiol, droloxifene, raloxifene, and tamoxifene.

Nonlimiting examples of cytotoxic/antiproliferative agents are taxol, vincristine, vinblastine, and doxorubicin.

Cathepsin K, formerly known as cathepsin O2, is a cysteine protease and is described in PCT International Application Publication No. WO 96/13523, published May 9, 1996; U.S. Pat. No. 5,501,969, issued Mar. 3, 1996; and U.S. Pat. No. 5,736,357, issued Apr. 7, 1998, all of which are incorporated by reference herein in their entirety. Cysteine proteases, specifically cathepsins, are linked to a number of disease conditions, such as tumor metastasis, inflammation, arthritis, and bone remodeling. At acidic pH's, cathepsins can degrade type-I collagen. Cathepsin protease inhibitors can inhibit osteoclastic bone resorption by inhibiting the degradation of collagen fibers and are thus useful in the treatment of bone resorption diseases, such as osteoporosis.

The present invention is also directed to combinations of the compounds of the present invention with one or more agents useful in the prevention or treatment of osteoporosis. For example, the compounds of the instant invention may be effectively administered in combination with effective amounts of other agents such as an organic bisphosphonate; an estrogen receptor modulator, or a cathepsin K inhibitor.

Additional illustrations of the invention are methods of treating tumor growth in a mammal in need thereof, comprising administering to the mammal a therapeutically effective amount of a compound described above and one or more agents known to be cytotoxic/antiproliferative. Also, the compounds of the present invention can be administered in combination with radiation therapy for treating tumor growth and metastasis.

In addition, the integrin $\alpha v\beta 3$ antagonist compounds of the present invention may be effectively administered in combination with a growth hormone secretagogue in the therapeutic or prophylactic treatment of disorders in calcium or phosphate metabolism and associated diseases. These diseases include conditions which can benefit from a reduction in bone resorption. A reduction in bone resorption should improve the balance between resorption and formation, reduce bone loss or result in bone augmentation. A reduction in bone resorption can alleviate the pain associated with osteolytic lesions and reduce the incidence and/or growth of those lesions. These diseases include: osteoporosis (including estrogen deficiency, immobilization, glucocorticoid induced and senile), osteodystrophy, Paget's disease, myositis ossificans, Bechterew's disease, malignant hypercalcemia, metastatic bone disease, periodontal disease, cholelithiasis, nephrolithiasis, urolithiasis, urinary calculus, hardening of the arteries (sclerosis), arthritis, bursitis, neuritis and tetany. Increased bone resorption can be accompanied by pathologically high calcium and phosphate concentrations in the plasma, which would be alleviated by this treatment. Similarly, the present invention would be useful in increasing bone mass in patients with growth hormone deficiency. Thus, preferred combinations are simultaneous or alternating treatments of an αvβ3 receptor antagonist of the present invention and a growth hormone secretagogue, optionally including a third component comprising an organic bisphosphonate, preferably alendronate monosodium trihydrate.

In accordance with the method of the present invention, the individual components of the combination can be administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the compounds of this invention with other agents useful for treating integrin-mediated conditions includes in principle any combination with any pharmaceutical composition useful for treating osteoporosis.

As used herein, the term "composition" is intended to encompass a product comprising the specified ingredients in the specified amounts, as well as any product which results, directly or indirectly, from combination of the specified ingredients in the specified amounts.

The compounds of the present invention can be administered in such oral dosage forms as tablets, capsules (each of which includes sustained release or timed release formulations), pills, powders, granules, elixirs, tinctures, suspensions, syrups and emulsions. Likewise, they may also be administered in intravenous (bolus or infusion), intraperitoneal, topical (e.g., ocular eyedrop), subcutaneous, intramuscular or transdermal (e.g., patch) form, all using forms well known to those of ordinary skill in the pharmaceutical arts. An effective but non-toxic amount of the compound desired can be employed as an αvβ3 antagonist.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

In the schemes and examples below, various reagent symbols and abbreviations have the following meanings:
AcOH: Acetic acid.
BH$_3$DMS: Borane.dimethylsulfide.
BOC(Boc): t-Butyloxycarbonyl.
BOP: Benzotriazol-1-yloxytris(dimethylamino)-phosphonium hexafluorophosphate.
CBZ(Cbz): Carbobenzyloxy or benzyloxycarbonyl.
CDI: Carbonyldiimidazole.
CH$_2$Cl$_2$: Methylene chloride.
CH$_3$CN: Acetonitrile CHCl₃: Chloroform.
DEAD: Diethyl azodicarboxylate.
DIAD: Diisopropyl azodicarboxylate.
DIBAH or
DIBAL-H: Diisobutylaluminum hydride.
DIPEA: Diisopropylethylamine.
DMAP: 4-Dimethylaminopyridine.
DME: 1,2-Dimethoxyethane.
DMF: Dimethylformamide.
DMSO: Dimethylsulfoxide.
DPFN: 3,5-Dimethyl-1-pyrazolylformamidine nitrate.
EDC: 1-(3-Dimethylaminopropyl)-3-ethylcarbodiimide.HCl
EtOAc: Ethyl acetate.
EtOH: Ethanol.
HOAc: Acetic acid.
HOAT: 1-Hydroxy-7-azabenzotriazole
HOBT: 1-Hydroxybenzotriazole.
IBCF: Isobutylchloroformate
LDA: Lithium diisopropylamide.
MeOH: Methanol.
MMNG 1,1-methyl-3-nitro-1-nitrosoguanidine
NEt₃: Triethylamine.
NMM: N-methylmorpholine.
PCA.HCl: Pyrazole carboxamidine hydrochloride.
Pd/C: Palladium on activated carbon catalyst.
Ph: Phenyl.
pTSA p-Toluenesulfonic acid.
TEA: Triethylamine.
TFA: Trifluoroacetic acid.
THF: Tetrahydrofuran.
TLC: Thin Layer Chromatography.
TMEDA: N,N,N',N'-Tetramethylethylenediamine.
TMS: Trimethylsilyl.

The novel compounds of the present invention can be prepared according to the procedure of the following schemes and examples, using appropriate materials and are further exemplified by the following specific examples. The compounds illustrated in the examples are not, however, to be construed as forming the only genus that is considered as the invention. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

The following Schemes and Examples describe procedures for making representative compounds of the present invention. Moreover, by utilizing the procedures described in detail in PCT International Application Publication Nos. WO95/32710, published Dec. 7, 1995, and WO95/17397, published Jun. 29, 1995, both of which are incorporated by reference herein in their entirety, in conjunction with the disclosure contained herein, one of ordinary skill in the art can readily prepare additional compounds of the present invention claimed herein. Additionally, for a general review describing the synthesis of β-alanines which can be utilized as the C-terminus of the compounds of the present invention, see Cole, D. C., *Recent Stereoselective Synthetic Approaces to β-Amino Acids, Tetrahedron*, 1994, 50, 9517–9582; Juaristi, E, et al., *Enantioselective Synthesis of β-Amino Acids, Aldrichimica Acta*, 1994, 27, 3. In particular, synthesis of the 3-methyl-β-alanine is taught in Duggan, M. F. et al., *J. Med. Chem.*, 1995, 38, 3332–3341; the 3-ethynyl-β-alanine is taught in Zablocki, J. A., et al., *J. Med. Chem.*, 1995, 38, 2378–2394; the 3-(pyridin-3-yl)-β-alanine is taught in Rico, J. G. et al., *J. Org. Chem.*, 1993, 58, 7948–7951; and the 2-amino- and 2-tosylamino-β-alanines are taught in Xue, C-B, et al., *Biorg. Med. Chem. Letts.*, 1996, 6, 339–344. The references described in this paragraph are all also incorporated by reference herein in their entirety.

SCHEME 1

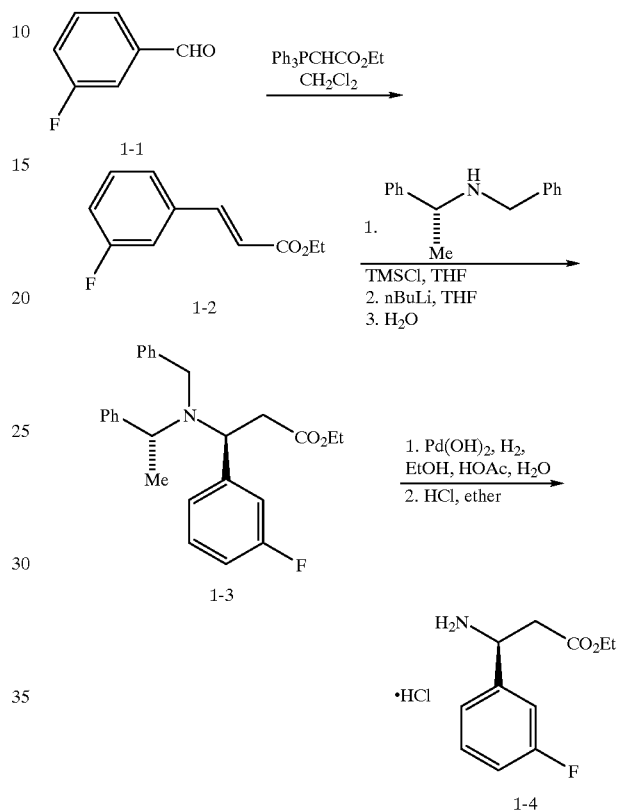

Ethyl 3-fluorocinnamate (1-2)

To a solution of 3-fluorobenzaldehyde 1-1 (18.16 g, 146 mmol) in dichloromethane (500 mL) was added ethyl (triphenylphosphoranylidene)acetate (61.2 g; 176 mmol) and the resulting solution was stirred at room temperature for 18 hr. After evaporation of the solvent, the residue was swirled with ether/hexane and filtered. The filtrate was concentrated and then purified on a plug of silica gel eluting with hexane/EtOAc 9:1. Removal of the solvent afforded the title compound 1-2 as an oil (~95% trans) which was used without further purification in the next step.

$^1$H NMR (CDCl₃): δ 1.36 (3H, t), 4.28 (2H, q), 6.43 (1H, d), 7.08 (1H, m), 7.2–7.4 (3H, m), 7.64 (1H, d).

N-Benzyl-(R)-α-methylbenzyl-3(S)-fluorophenyl-β-alanine ethyl ester (1-3)

To a solution of N-benzyl-(R)-α-methylbenzylamine (33.4 g, 158 mmol) in THF (450 mL) at 0° C. was added n-butyllithium (1.6M in hexanes; 99 mL, 158 mmol). The dark violet solution was stirred at 0° C. for 30 minutes, cooled to −78° C. and the ester 1-2 (29.2 g, 150 mmol) in THF (100 mL) was added over 5 minutes. The resulting solution was stirred at −78° C. for 1 hr, then warmed to room temperature. After 2 hrs, the mixture was poured into water and extracted with EtOAc, washed with water, then brine, dried and concentrated in vacuo to give an oil. Column chromatography (silica gel; hexane/EtOAc 1:1 then pure EtOAc) gave the title compound 1-3.

¹H NMR (CDCl₃): δ 1.06 (3H, t), 1.28 (3H, d), 2.52 (1H, dd), 2.62 (1H, dd), 3.66 (1H, d), 3.72 (1H, d), 3.95 (2H, q), 4.44 (1H, dd), 6.95 (1H, m), 7.1–7.5 (13H, m).

3(S)-Fluorophenyl-β-alanine ethyl ester hydrochloride (1-4)

A solution of the N-benzyl-(R)-α-methylbenzylamine derivative 1-3 (28.2 g, 69.6 mmol) in ethanol (300 mL), acetic acid (30 mL) and water (3 mL) was degassed with argon for 30 minutes. Pd(OH)₂ on carbon (20% dry weight; 2.6 g) was added and the mixture then stirred under a hydrogen atmosphere (balloon) for 2 hours. The mixture was filtered through celite and the solvent removed in vacuo to give an oil. This oil was dissolved in 200 mL ether and to this solution was added 60 mL 1N HCl in ether to yield a precipitate. Filtration and washing the solid with ether/hexane then gave the title compound 1-4 as a white solid.

¹H NMR (CD₃OD): δ 1.21 (3H, t), 3.0–3.2 (2H, m), 4.16 (2H, q), 4.76 (1H, t), 7.2–7.35 (3H, m), 7.5 (1H, m).

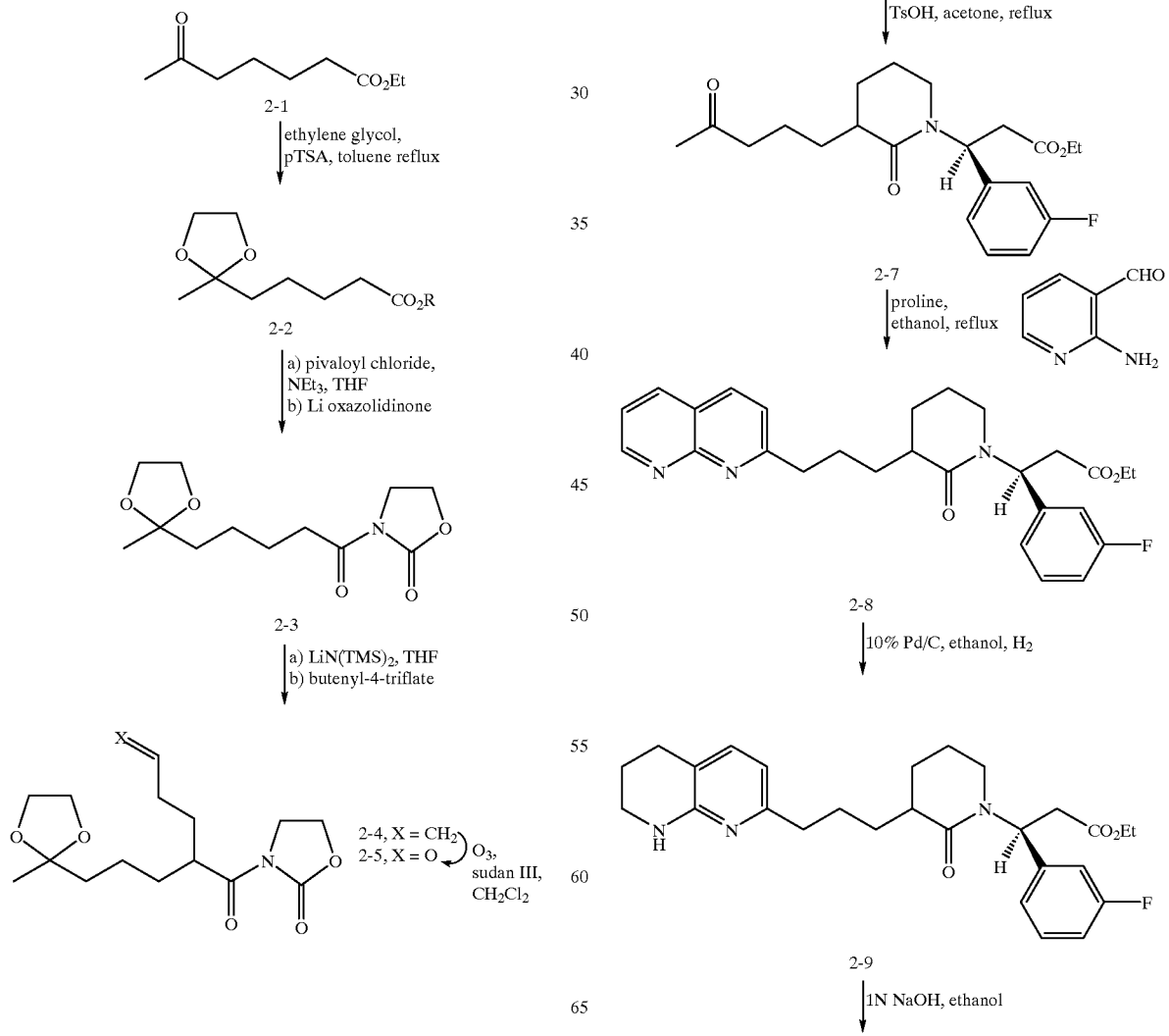

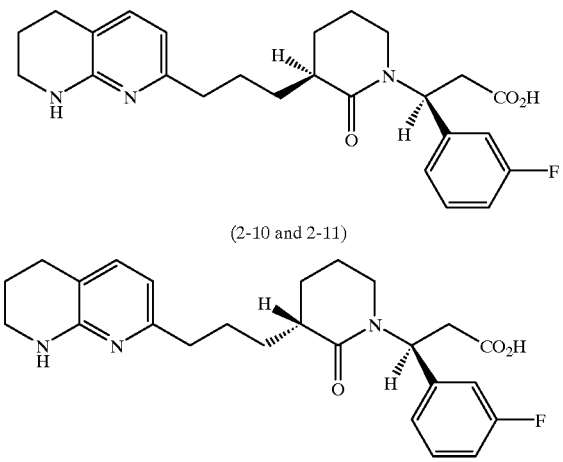

(2-10 and 2-11)

5-(2-Methyl-[1,3]dioxolan-2-yl)-pentanoic acid (2—2)

A mixture of ketone 2-1 (18 g, 105 mmol), ethylene glycol (3.2 ml, 110 mmol), p-TSA (50 mg, 0.2713 mmol) and toluene (300 mL) was heated to reflux with azeotropic removal of water for 24 hours. The reaction mixture was diluted with EtOAc and then washed with sat. NaHCO$_3$, brine, dried (MgSO$_4$), and concentrated. The residue was dissolved in EtOH (200 ml) and then treated with 1N NaOH (120 ml, 120 mmol). After 2 h, the reaction was poured into 600 mL 2:1 Et$_2$O/10% KHSO$_4$. The organic portion was separated, washed with brine, dried (MgSO$_4$) and concentrated to give acid 2—2 as a colorless oil.

$^1$H NMR (300 MHz, CDCl$_3$) δ 3.93 (m, 4H), 2.36 (m, 2H), 1.63 (m, 4H), 1.46 (m, 2H), 1.31 (s, 3H).

3-[5-(2-Methyl-[1,3]dioxolan-2-yl)-pentanoyl]-oxazolidin-2-one (2-3)

To a stirred solution of 2-2 (16.0 g, 85.5 mmol), NEt$_3$ (13.1 ml, 94.1 mmol) and THF (400 mL) at −78° C. was added pivaloyl chloride (11.6 ml, 94.1 mmol). The mixture was warmed to 0° C. for 1.0 h and then recooled to −78° C. To a stirred solution of 2-oxazolidinone (9.3 g, 106.9 mmol) and THF (200 ml) at −78° C. was added nBuLi (43.0 ml, 106.9 mmol, 2.5M in hexanes) dropwise over 10 minutes. After 20 minutes, the lithium reagent was transferred to the mixed anhydride via cannula. After 10 minutes, the reaction was warmed to 0° C. for 1.0 h. The mixture was diluted with ethyl acetate, washed with sat. NaHCO$_3$, brine, and dried over MgSO$_4$. Following evaporative removal of the solvent, the residue was chromatographed (silica gel, 40%–50% EtOAc/hexanes) to give 2-3 as a colorless foam.

TLC R$_f$=0.19 (silica, 40% EtOAc/hexanes); $^1$H NMR (300 MHz, CDCl$_3$) δ 4.41 (t, J=8.1 Hz, 2H), 4.02 (t, J=8.1 Hz, 2H), 3.93 (m, 4H), 3.93 (t, J=7.3 Hz, 2H), 1.66 (m, 4H), 1.48 (m, 2H), 1.31 (s, 3H).

3-(2-[3-(2-Methyl-[1,3]dioxolan-2-yl)-propyl]-hex-5-enoyl)-oxazolidin-2-one (2-4)

To a stirred solution of 2-3 (3.0 g, 11.7 mmol) and THF (125 mL) at −78° C. was added NaN(TMS)$_2$ (15.2 mL, 15.2 mmol, 1.0 M in THF) dropwise over 20 minutes. Butenyl-4-triflate (5.0 mL, 29.2 mmol) was added dropwise; after 1 h, the reaction was warmed to 0° C. After 1 h, the reaction was diluted with EtOAc, washed with sat. NaHCO$_3$, brine, dried (MgSO$_4$) and concentrated. Flash chromatography (silica, 40% EtOAc/hexanes) gave 2-4 as an yellow oil.

TLC R$_f$=0.28 (silica, 50% EtOAc/hexanes); $^1$H NMR (300 MHz, CDCl$_3$) δ 5.80 (m, 1H), 5.00 (m, 2H), 4.40 (m, 2H), 4.02 (m, 2H), 3.92 (m, 4H), 2.40–1.35 (m, 11H), 1.30 (s, 3H).

7-(2-Methyl-[1,3]dioxolan-2-yl)-4-(2-oxo-oxazolidine-3-carbonyl)-heptanal (2-5)

To a stirred solution of 2-4 (1.8 g, 5.8 mmol), sudan III (10 mg) and CH$_2$Cl$_2$ (150 mL) at −78° C. under argon was bubbled ozone until the red solution changed to yellow-orange. The solution was purged with argon for 30 minutes. PPh$_3$ (2.26 g, 8.7 mmol) was added followed by the removal of the cooling bath. After 1.5 h, the reaction was concentrated. Flash chromatography (silica, 20%–50% EtOAc/hexanes) gave 2-5 as a yellow solid.

TLC R$_f$=0.17 (silica, 50% EtOAc/hexanes); $^1$H NMR (300 MHz, CDCl$_3$) δ 9.74 (s, 1H), 4.43 (m, 2H), 4.03 (m, 2H), 3.91 (m, 4H), 3.80 (1H), 3.04 (m, 1H), 2.48 (m, 2H), 2.10–1.40 (m, 8H), 1.29 (s, 3H).

3(S)-(3-Fluoro-phenyl)-3-{2-oxo-[3-(2-methyl-[1,3]dioxolan-2-yl)-propyl]-piperidin-1-yl}-propionic acid ethyl ester (2-6)

A mixture of 2-5 (600 mg, 1.0 mmol), 1-4 (240 mg, 1.0 mmol), Na(OAc)$_3$BH (313 mg, 1.5 mol) and NEt$_3$ (0.28 mL, 2.0 mmol) in DCE (10 mL) was stirred for 24 h. The mixture was diluted with ethyl acetate, washed with 10% K$_2$CO$_3$, brine, and dried over MgSO$_4$. Following evaporative removal of the solvent, the residue was chromatographed (silica gel, 50:35:14:1 hexanes/chloroform/ethyl acetate/MeOH) to give 2-6 as a yellow solid.

TLC R$_f$=0.53 (silica, 70:25:5 chloroform/ethyl acetate/MeOH); $^1$H NMR (300 MHz, CDCl$_3$) δ 7.30 (m, 1H), 7.07 (m, 1H), 6.98 (m 3H), 6.35 (m, 0.5H), 6.23 (m, 0.5H), 4.12 (q, J=7 Hz, 2H), 3.92 (m, 4H), 3.20 (m, 1H), 2.95 (m, 3H), 2.38 (m, 1H), 2.00–1.40 (m, 8H), 1.30 (s, 3H), 1.22 (t, J=7 Hz, 3H).

3(S)-(3-Fluorophenyl)-3-[2-oxo-3-(4-oxo-pentyl)-piperidin-1-yl]-propionic acid ethyl ester (2-7)

A solution of 2-6 (500 mg, 1.10 mmol), p-TSA (10 mg) and acetone (50 mL) was heated at reflux for 4 h. The cooled reaction mixture was diluted with EtOAc and then washed with sat. NaHCO$_3$ and brine, dried (MgSO$_4$), and concentrated to afford 2-7 as a yellow oil.

$^1$H NMR (300 MHz, CDCl$_3$) δ 7.30 (m, 1H), 7.06 (m, 1H), 6.98 (m, 2H), 6.32 (m, 0.5H), 6.20 (m, 0.5H), 4.12 (q, J=7 Hz, 2H), 3.20 (m, 1H), 2.95 (m, 3H), 2.45 (m, 2H), 2.33 (m, 1H), 2.14 (s, 3H), 2.00–1.40 (m, 8H), 1.22 (t, J=7 Hz, 3H).

3(S)-(3-Fluorophenyl)-3-[3-(3-[1,8]naphthyridin-2-yl-propyl)-2-oxo-piperidin-1-yl]-propionic acid ethyl ester (2-8)

A mixture of 2-7 (450 mg, 1.2 mmol), 2-amino-3-formylpyridine (145 mg, 1.2 mmol; for prep., see JOC 1983,48, 3401) and proline (137 mg, 1.2 mmol) in absolute ethanol (20 mL) was heated at reflux for 12 h. Following evaporative removal of the solvent, the residue was chromatographed (silica gel, 50% ethyl acetate/chloroform to 70:25:5 chloroform/ethyl acetate/MeOH) to give 2-8 as a yellow oil.

TLC Rf=0.34 (70:25:5 chloroform/ethyl acetate/MeOH). $^1$H NMR (300 MHz, CDCl$_3$) δ 9.08 (m, 1H), 8.16 (dd, J=2.0 Hz, 8.0 Hz 1H), 8.11 (d, J=8.3 Hz, 1H), 7.42 (m, 2H), 7.06 (m, 1H), 6.97 (m, 2H), 6.35 (m, 0.5H), 6.20 (m, 0.5H), 4.11 (m, 2H), 3.20–2.80 (m, 5H), 2.40 (m, 1H), 2.10–1.40 (m, 8H), 1.19 (m, 3H).

3(S)-(3-Fluorophenyl)-3-(2-oxo-3-[3-(5,6,7,8-tetrahydro-[1,8]naphthyridin-2-yl)-propyl]-piperidin-1-yl)-propionic acid ethyl ester (2-9)

A mixture of 2-8 (400 mg, 0.86 mmol) and 10% Pd/carbon (1300 mg) in EtOH (10 mL) was stirred under a balloon of hydrogen for 6 h. Following filtration and evaporative removal of the solvent, the residue was chromatographed (silica gel, 70:25:5 chloroform/ethyl acetate/MeOH) to give 2-9 as a yellow oil.

TLC Rf=0.21 (70:25:5 chloroform/ethyl acetate/MeOH). $^1$H NMR (300 MHz, CDCl$_3$) δ 7.29 (m, 1H,), 7.05 (m, 2H), 6.98 (m, 2H), 6.33 (m, 1H), 6.30 (m, 0.5H), 6.20 (m, 0.5H), 4.76 (bs, 1H), 4.10 (m, 2H), 3.40 (m, 2H), 3.20 (m, 1H), 3.00–2.90 (m, 3H), 2.70 (t, J=6.3 Hz, 2H), 2.55 (m, 2H), 2.35 (m, 1H), 2.00–1.40 (m, 8H), 1.23 (t, J=7 Hz, 3H).

3(S)-(3-Fluorophenyl)-3-(2-oxo-3(R or S)-[3-(5,6,7,8-tetrahydro-[1,8]naphthyridin-2-yl)-propyl]-piperidin-1-yl)-propionic acid and 3(S)-(3-fluorophenyl)-3-(2-oxo-3(S or R)-[3-(5,6,7,8-tetrahydro-[1,8]naphthyridin-2-yl)-propyl]-piperidin-1-yl)-propionic acid (2-10 and 2-11)

To a solution of 2-9 (300 mg, 0.6614 mmol) in ETOH (3 mL) was added 1N NaOH (0.725 ml, 0.725 mmol). After stirring for 1 h, the solvents were evaporated and the residue was chromatographed (silica gel, 25:10:1:1–15:10:1:1 ethyl acetate/EtOH/water/NH$_4$OH) to give 2-10 and 2-11 as pure diastereomeric white solids.

TLC Rf=0.62 (isomer A) (10:10:1:1 ethyl acetate/EtOH/water/NH$_4$OH). TLC Rf=0.51 (isomer B) (10:10:1:1 ethyl acetate/EtOH/water/NH$_4$OH). $^1$H NMR (300 MHz, CD$_3$OD, Isomer A) δ 7.46 (d, J=7 Hz, 1H), 7.37 (m, 1H), 7.15 (m, 1H), 7.10 (m, 1H,), 7.03 (m, 1H), 6.50 (d, J=7 Hz, 1H,), 6.43 (m, 1H), 3.48 (m, 2H), 3.36 (m, 2H), 3.00 (m, 1H), 2.90 (m, 2H), 2.70 (m, 2H), 2.80–2.55 (m, 3H), 2.12–1.40 (m, 10H). $^1$H NMR (300 MHz, CD$_3$OD, Isomer B) δ 7.40 (d, J=7 Hz, 1H), 7.34 (m, 1H), 7.15 (m, 1H), 7.10 (m, 1H,), 7.00 (m, 1H), 6.50 (d, J=7 Hz, 1H,), 5.63 (m, 1H), 3.45 (m, 2H), 3.36 (m, 2H), 3.15 (m, 2H), 2.82 (m, 1H), 2.78 (m, 2H), 2.63 (m, 2H), 2.47 (m, 1H), 2.00–1.50 (m, 10H).

SCHEME 3

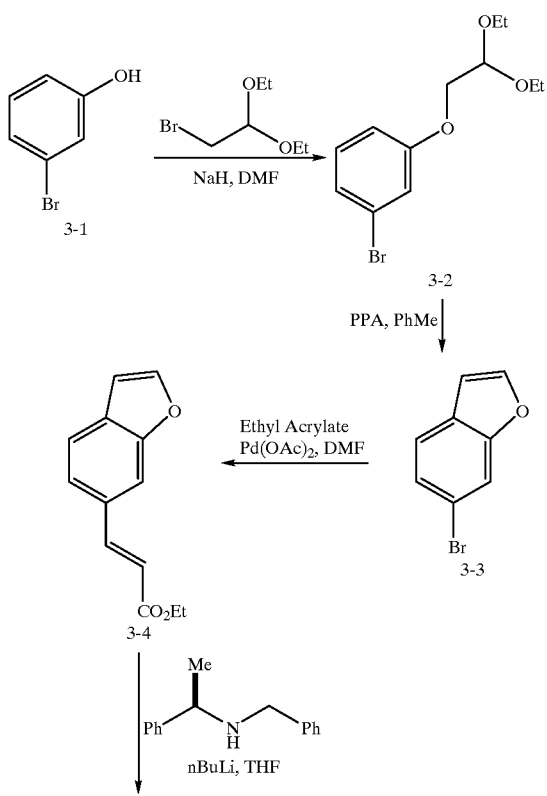

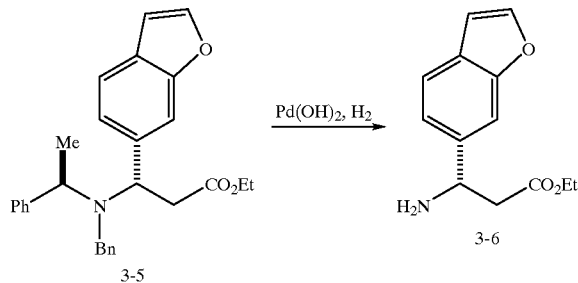

1-Bromo-3-(2,2-diethoxy-ethoxy)-benzene (3-2)

To a suspension of NaH (2.77 g, 115.6 mmol) in DMF (100 mL) at 0° C. was added a solution of 3-bromophenol 3-1 in DMF (40 mL) over 40 min. After the addition was complete, the solution was stirred for an additional 30 min. The solution was then treated with neat bromoacetaldehyde diethyl acetal (17.36 g, 115.6 mmol). The solution was heated at 100° C. for 8 h, cooled to room temperature, and extracted with Et$_2$O (3×200 mL). The combined organic extracts were washed with 10% aq. NaOH (100 mL) and brine (100 mL), dried over MgSO$_4$, filtered and concentrated to give 3-2 as a yellow oil.

TLC Rf=0.4 (10% ethyl acetate/hexanes). $^1$H NMR (300 MHz, CDCl$_3$) δ 7.19–7.05 (m, 3H), 6.85 (d, 1H), 4.81 (t, 1H, J=6.8 Hz), 3.99 (d, 2H, J=6.8 Hz), 3.71 (m, 4H), 1.22 (t, 6H, J=7.1 Hz) ppm.

6-Bromo-benzofuran (3—3)

To a solution of the acetal 3-2 in toluene (200 mL) was added polyphosphoric acid (20 g). The biphasic mixture was heated to 100° C. and stirred at this temperature for 4 h. The mixture was cooled to room temperature, poured onto ice, and extracted with Et$_2$O (2×200 mL). The combined organic extracts were washed with saturated aq. NaHCO$_3$ and brine. The solution was dried over MgSO$_4$, filtered, and concentrated. The residue was purified by flash chromatography (100% hexanes) to give the product 3-3 as a yellow oil.

TLC Rf=0.3 (100% hexanes). $^1$H NMR (300 MHz, CDCl$_3$) δ 7.68 (s, 1H), 7.60 (d, 1H, J=2.1 Hz), 7.46 (d, 1H, J=8.4 Hz), 7.36 (dd, 1H, J=8.1, 1.5 Hz), 6.75 (dd, 1H, J=7.1, 0.9 Hz) ppm.

3-(Benzofuran-6-yl)-acrylic acid ethyl ester (3-4)

A mixture of the 6-bromo-benzofuran 3-3 (1.74 g, 8.79 mmol), ethyl acrylate (1.09 g, 10.98 mmol), Pd(OAc)$_2$ (0.099 g, 0.44 mmol), tri-o-tolylphosphine (0.268 g, 0.880 mmol), and sodium acetate (3.60 g, 43.9 mmol) in DMF (10 mL) was heated to 100° C. in a sealed tube for 4 h. The mixture was cooled to room temperature, diluted with water, and extracted with Et$_2$O (2×40 mL). The combined organic extracts were washed with brine (30 mL), dried over MgSO$_4$, filtered, and concentrated. The residue was purified by flash chromatography (10% ethyl acetate/hexanes) to give the ester 3-4 as an off-white solid.

TLC Rf=0.3 (10% ethyl acetate/hexanes). $^1$H NMR (300 MHz, CDCl$_3$) δ 7.78 (d, 1H, J=15.9 Hz), 7.68 (d, 1H, J=2.4 Hz), 7.66 (s, 1H), 7.59 (d, 1H, J=8.4 Hz), 7.43 (dd, 1H, J=9.0, 1.5 Hz), 6.78 (m, 1H), 6.47 (d, 1H, J=15.9 Hz), 4.27 (q, 2H, J=7.2 Hz), 1.34 (t, 3H, J=7.2 Hz) ppm.

3(S)-Benzofuran-6-yl-3-[benzyl-(1(R)-phenyl-ethyl)-amino]-propionic acid ethyl ester (3-5)

A solution of N-benzyl-α-(R)-methylbenzylamine (1.32 g, 6.30 mmol) in THF (25 mL) at 0° C. was treated with n-BuLi (2.52 mL of a 2.5 M soln in hexanes). The resulting solution was stirred at 0° C. for 30 min and then cooled to −78° C. A solution of acrylate 3-4 (0.681 g, 3.15 mmol) in THF (5 mL) was added. After stirring for 15 min at −78° C., satd. aq. NH$_4$Cl soln (5 mL) was added and the cold bath removed. The mixture was warmed to room temperature and extracted with Et$_2$O (2×40 mL). The combined organic extracts were washed with brine (30 mL), dried over MgSO$_4$, filtered, and concentrated. The residue was purified by flash chromatography (10% ethyl acetate/hexanes) to give the β-aminoester 3-5 as a yellow oil.

TLC R$_f$=0.8 (10% ethanol/dichloromethane). $^1$H NMR (300 MHz, CDCl$_3$) δ 7.58 (m, 3H), 7.41 (m, 2H), 7.22 (m, 9H), 7.59 (s, 1H), 4.58 (m, 1H), 4.05 (m, 1H), 3.91 (q, 2H, J=7.1 Hz), 3.72 (m, 2H), 2.62 (m, 2H), 1.21 (d, 3H, J=7.2 Hz), 1.03 (t, 3H, J=7.1 Hz) ppm.

3(S)-Amino-3-(2,3-dihydro-benzofuran-6-yl)-propionic acid ethyl ester (3-6)

A mixture of the dibenzylamine 3-5 (1.19 g, 2.78 mmol) in EtOH/H$_2$O/AcOH (26 mL/3 mL/1.0 mL) was degassed with argon and treated with Pd(OH)$_2$ (1.19 g). The mixture was placed under 1 atm of H$_2$. After stirring for 18 h, the mixture was diluted with EtOAc, and filtered through celite. The filtrate was concentrated and the residue purified by flash chromatography (10% ethyl acetate/dichloromethane) to give the ester 3-6 as a white solid.

TLC Rf=0.25 (10% ethanol/dichloromethane). $^1$H NMR (300 MHz, CD$_3$OD) as the trifluoroacetate salt: δ 7.25 (d, 1H, J=8.1 Hz), 6.88 (m, 1H), 7.66 (s, 1H), 6.82 (s, 1H), 4.58 (m, 3H), 4.12 (m, 2H), 3.30 (m, 1H), 3.19 (m, 2H), 2.98 (m, 2H), 1.11 (t, 3H, J=7.2 Hz) ppm.

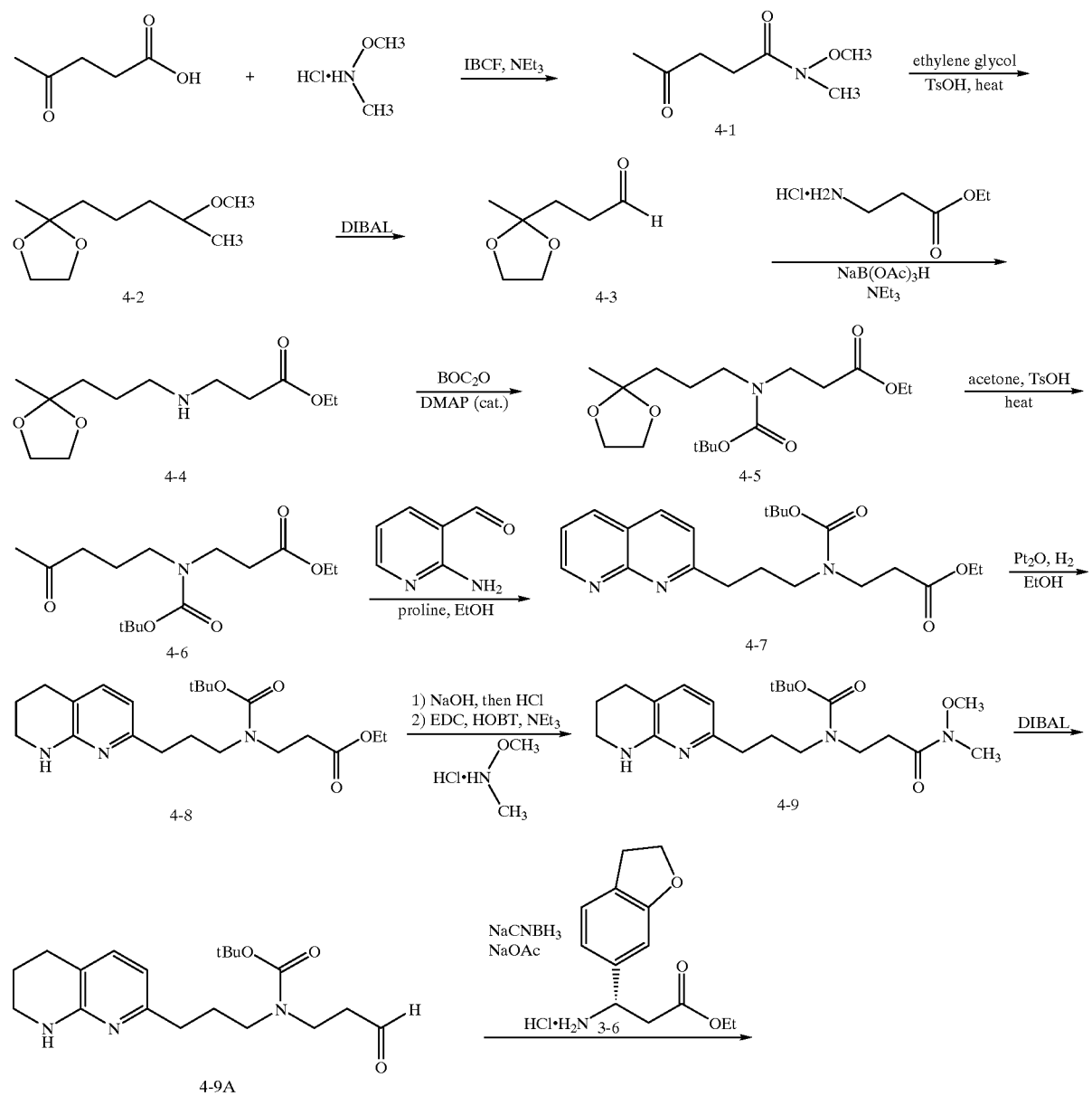

SCHEME 4

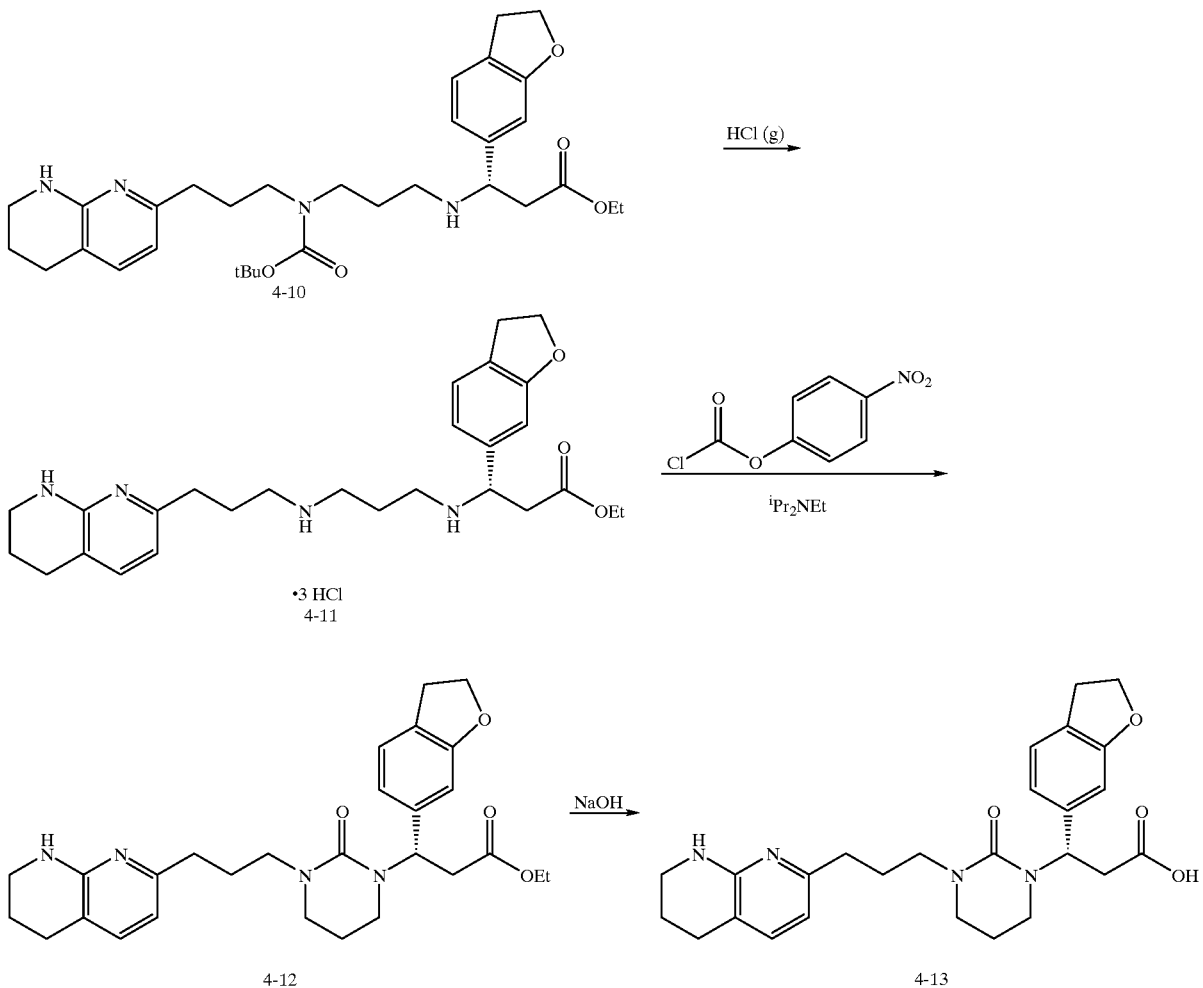

4-Oxo-pentanoic acid methoxy-methyl-amide (4-1)

To a stirred solution of levulinic acid (30 g, 0.258 mol) in 850 mL CHCl$_3$ at 0° C. was added triethylamine (43.2 mL, 0.310 mol), followed by isobutyl chloroformate (37 mL, 0.284 mol) over 15 minutes. After 30 minutes, triethylamine (57.6 mL, 0.413 mol) was added, followed by N,O-dimethylhydroxylamine hydrochloride (37.8 g, 0.387 mol) in 5 portions over 5 minutes. Vigorous bubbling ensued, and the mixture was allowed to warm to RT and stir for 1 h. The mixture was reduced to a moist solid by rotary evaporation under reduced pressure, slurried in 500 mL EtOAc, washed with 10% K$_2$CO$_3$, brine, and dried over Na$_2$SO$_4$. Evaporative removal of the solvent gave 4-1 as a yellow oil.

TLC R$_f$=0.42 (silica, 1:1 chloroform/ethyl acetate). $^1$H NMR (300 MHz, CDCl$_3$) δ 3.74 (s, 3H), 3.18 (s, 3H), 2.65–2.95 (m, 4H), 2.21 (s, 3H).

N-methoxy-N-methyl-3-(2-methyl-[1,3]dioxolan-2-yl)-propionamide (4-2)

To a solution of 4-1 (38 g, 0.239 mol) in 500 mL benzene was added ethylene glycol (17.3 mL, 0.310 mol) and p-toluenesulfonic acid (1 g). The mixture was heated at reflux for 2 h with azeotropic removal of water. After cooling, the solution was washed with 200 mL sat. NaHCO$_3$, brine, and dried over Na$_2$SO$_4$. Evaporative removal of the solvent gave 4-2 as a yellow oil.

TLC R$_f$=0.62 (silica, ethyl acetate). $^1$H NMR (300 MHz, CDCl$_3$) δ 3.95 (m, 4H), 3.68 (s, 3H), 3.17 (s, 3H), 2.51 (t, 2H, J=8 Hz), 2.00 (t, 3H, J=6 Hz) 1.33 (S, 3H).

3-(2-Methyl-[1,3]dioxolan-2-yl)-propionaldehyde (4-3)

To a solution of 5-2 (44.74 g, 0.22 mol) in 400 mL THF at −78° C. was added DIBAL (264 mL 1 M in hexanes, 0.264 mol) over 10 minutes. After stirring for 1 h, 350 ml of 1.0 M Rochelle's salt and 300 ml ether was added followed by the removal of the cooling bath. After stirring for 1 h, the organic portion was separated and dried over Na$_2$SO$_4$. Evaporative removal of the solvent gave 4-3 as a colorless oil.

TLC R$_f$=0.80 (silica, e1lhyl acetate). $^1$H NMR (300 MHz, CDCl$_3$) δ 9.73 (s, 3H), 3.50 (d, 3H, J=16 Hz), 2.61 (d, 1H, J=21 Hz), 2.48 (m, 1H), 2.07 (t, 1H, J=7H), 1.33 (2, 3H).

[3-(2-Methyl-[1,3]dioxolan-2-yl)-propylamino]propionic acid ethyl ester (4—4)

To a solution of 4-3 (10 g, 0.69 mmol) in 200 mL 1,2-dichloroethane at 0° C. was added beta-alanine ethyl ester hydrochloride (21 g, 0.138 mol), triethylamine (34 mL), and NaB(OAc)$_3$H (20.5 g, 0.097 mol). The mixture was allowed to warm to RT and stir for 15 h. The mixture was evaporated to one-third its initial volume, diluted with EtOAc and then washed with 10% K$_2$CO$_3$, brine, and dried over Na$_2$SO$_4$. Following evaporative removal of the solvent, the residue was chromatographed (silica gel, 70:25:5 chloroform/ethyl acetate/methanol) to give 4-4 as a yellow oil.

TLC R$_f$=0.19 (silica, 70:25:5 chloroform/ethyl acetate/methanol).

{Tert-butoxycarbonyl-[3-(2-methyl-[1,3]dioxolan-2-yl)-propyl]-amino}-propionic acid ethyl ester (4-5)

To a solution of 4-4 (10 g, 0.041 mol) in 200 mL THF was added a trace of DMAP, 20 drops of triethylamine, and $BOC_2O$ (9.5 g, 0.045 mol). After 1 h, evaporative removal of the solvent gave 4-5 as a colorless oil.

TLC $R_f$=0.91 (silica, 70:25:10 chloroform/ethyl acetate/methanol). $^1$H NMR (300 MHz, $CDCl_3$) δ 4.15 (q, 2H, J=4 Hz), 3.93 (m, 4H), 3.46 (m, 2H), 3.22 (m, 2H), 2.58 (m, 2H), 1.61 (m, 4H), 1.48 (m, 9H), 1.28 (m, 6H).

[Tert-butoxycarbonyl-(4-oxo-pentyl)-amino]-propionic acid ethyl ester (4-6)

To a solution of 4-5 (13.9 g, 0.040 mol) in 100 mL acetone was added p-toluenesulfonic acid (0.05 g). The mixture was heated at reflux for 2 h. After cooling, the mixture was evaporated to one-fifth its initial volume, diluted with EtOAc and then washed with sat. $NaHCO_3$, brine, and dried over $Na_2SO_4$. Evaporative removal of the solvent gave 4-6 as a yellow oil.

TLC $R_f$=0.36 (silica, 30% ethyl acetate/hexane).

[Tert-butoxycarbonyl-(3-[1,8]naphthyridin-2-yl-propyl)-amino]-propionic acid ethyl ester (4-7)

To a solution of 4-6 (12 g, 40 mmol), 2-amino-3-formylpyridine (6.3 g, 52 mmol), proline (4.6 g, 40 mmol) and ethanol (300 mL) was heated at reflux for 15 h. After cooling and evaporation, the residue was chromatographed (silica gel, 1:1 chloroform/ethyl acetate) to give 4-7 as a yellow oil.

TLC $R_f$=0.47 (silica, 70:25:5 chloroform/ethyl acetate/methanol); $^1$H NMR (300 MHz, $CDCl_3$) δ 9.09 (m, 1H), 8.13 (m, 2H), 7.43 (m, 2H), 4.12 (q, 2H, 7 Hz), 3.42 (m, 4H), 3.03 (m, 2H), 2.48 (m, 2H), 2.16 (m, 2H), 1.42 (m, 9H), 1.22 (m, 3H).

{Tert-butoxycarbonyl-[3-(5,6,7,8-tetrahydro-[1,8]naphthyridin-2-yl)-propyl]-amino}-propionic acid ethyl ester (4-8)

A solution of 5-7 (7.0 g, 18.1 mmol), 10% Pd/C (5 g) and ethanol (100 mL) was stirred under a balloon of hydrogen gas for 15 h. Following filtration and evaporation, the residue was chromatographed (silica gel, 70:28:2 chloroform/ethyl acetate/methanol) to give 4-8 as a yellow oil.

TLC $R_f$=0.32 (silica, 70:28:2 chloroform/ethyl acetate/methanol).

[(Methoxy-methyl-carbamoyl)-ethyl]-[3-(5,6,7,8-tetrahydro-[1,8]naphthyridin-2-yl)-propyl]-carbamic acid tert-butyl ester (4-9)

To a solution of 4-8 (5.6 g, 12.8 mmol) in ethanol (50 mL) was added NaOH (15 mL 1M solution in water, 15 mmol). After stirring for 1 h, HCl (15 mL 1M solution in water, 15 mmol) was added, and the mixture evaporated to give an oily residue. The residue was evaporated from ethanol three times, and then from acetonitrile three times, producing a yellow crusty solid which was dried under a vacuum of <2 mm Hg for 2 h. This residue was then slurried in chloroform (5 mL) and acetonitrile (50 mL), and NMM (8.5 mL), N,O-dimethylhydroxylamine hydrochloride (2.5 g, 26 mmol), HOBT (1.7 g, 13 mmol) and EDC (2.4 g, 13 mmol) were added. After stirring for 15 h, the mixture was evaporated to dryness, the residue slurried in EtOAc, washed with sat. $NaHCO_3$, brine, and dried over $Na_2SO_4$. Evaporative removal of the solvent gave 4-9 as a yellow oil.

TLC $R_f$=0.20 (silica, 70:20:10 chloroform/ethyl acetate/methanol); $^1$H NMR (300 MHz, $CDCl_3$) δ 7.05 (d, 1H, J=8 Hz), 6.28 (d, 1H, J=8 Hz), 4.83 (m, 1H), 3.69 (m, 3H), 3.51 (m, 2H), 3.39 (m, 2H), 3.14 (m, 2H), 3.18 (s, 3H), 2.63 (m, 4H), 2.48 (m, 2H), 1.83 (m, 9H).

{Tert-butoxycarbonyl-[3-(5,6 7,8-tetrahydro-[1,8]naphthyridin-2-yl)-proply]-amino}-propionaldehyde (4-9A)

To a stirred solution of 4-9 (12.8 mmol) and THF (50 ml) at −78° C. was added DIBAL (1.0 M/hexanes, 15 ml, 15 mmol) dropwise over 20 minutes. After 1.0 hour, 20 ml of 1.0 M Rochelle's salt was added followed by the removal of the cooling bath. The mixture was stirred for 1.0 hour and then diluted with $Et_2O$. After 30 minutes of stirring, the organic portion was separated and dried over $MgSO_4$. Evaporative removal of the solvent gave crude aldehyde 4-9A as a colorless oil.

TLC $R_f$=0.13 (silica, 75:20:10 chloroform/EtOAc/MeOH).

3(S)-(2-{Tert-butoxycarbonyl-[3-(5,6,7,8-tetrahydro-[1,8]naphthyridin-2-yl)-propyl]-amino}-propylamino)-3-(2,3-dihydro-benzofuran-6-yl)-propionic acid ethyl ester (4-10)

A mixture of the crude aldehyde 4-9A (0.4 g, 1.15 mmol), 3-6 (0.5 g, 1.5 mmol), powdered molecular sieves (1 g), sodium acetate (1 g) and 2-propanol (20 mL) was stirred for 30 minutes at 0° C. Then $NaCNBH_3$ (0.215 g, 3.5 mmol) was added. After 15 hours, to the reaction was added 10% $KHSO_4$ until pH~2, stirred 5 minutes, diluted with EtOAc and then adjusted to pH~12 with $K_2CO_3$. The mixture was extracted with EtOAc and dried over $MgSO_4$. Following evaporative removal of the solvent, the residue was chromatographed (silica gel, 1% [10:1:1 $EtOH/NH_4OH/H_2O$]/99% 75:25:5 chloroform/EtOAc/MeOH) to give 4-10 as a yellow oil.

TLC $R_f$=0.19 (silica, 1% [10:1:1 $EtOH/NH_4OH/H_2O$]/99% 75:25:5 chloroform/EtOAc/MeOH); $^1$H NMR (300 MHz, $CDCl_3$) δ 7.10 (m, 2H),6.78 (m, 2H), 6.37 (d, 1H, J=7 Hz), 4.69 (br s, 1H), 4.47 (t, 2H, J=7 Hz), 4.11 (m, 2H), 3.95 (t, 1H, J=7 Hz), 3.38 (m, 2H), 3.17 (m, 6H), 2.7–2.4 (m, 8H), 1.82 (m, 5H), 1.61 (m, 2H), 1.40 (m, 9H), 1.21 (t, 3H, J=Hz).

3(S)-(2,3-dihydro-benzofuran-6-yl)-3-{2-oxo-3-[3-(5,6,7,8-tetrahydro-[1,8]naphthyridin-2-yl)-propyl]-tetrahydro-pyrimidin-1-yl}-propionic acid ethyl ester (4-12)

HCl gas was rapidly bubbled through a solution of 4-10 (0.3 g, 0.53 mmol) in dichloromethane (10 ml) at 0° C. for 10 minutes. After 30 minutes, the solution was purged with argon for 30 minutes. The solution was concentrated to give the amine 4-11 as a yellow solid. To a stirred mixture of 4-11 (0.53 mmol) in $CH_2Cl_2$ (10 mL) and $iPr_2NEt$ (0.56 mL, 3.3 mmol) was added para-nitrophenyl chloroformate (0.112 g, 0.55 mmol). After 30 minutes, dioxane (10 mL) was added, and the mixture heated to 100° C., allowing the dichloromethane to evaporate. After 12 h, the mixture was cooled, diluted with EtOAc, washed with 1 N NaOH, brine, and dried over $MgSO_4$. Evaporative removal of the solvent gave 4-12 as a yellow oil.

TLC $R_f$=0.37 (silica, 70:20:10 chloroform/ethyl acetate/methanol).

3(S)-(2,3-dihydro-benzofuran-6-yl)-3-{2-oxo-3-[3-(5,6,7,8-tetrahydro-[1,8]naphthyridin-2-yl)-propyl]-tetrahydro-pyrimidin-1-yl}-propionic acid (4-13)

To a solution of 4-12 (0.20 g, 0.41 mmol) in EtOH (5 mL) was added 1N NaOH (0.5 ml, 0.5 mmol). After stirring for 2 h, the solvents were evaporated and the residue was chromatographed (silica gel, 25:10:1:1 followed by 15:10:1:1 ethyl acetate/EtOH/water/$NH_4OH$) to give 4-13 as a white solid.

TLC Rf=0.13 (10:10:1:1 ethyl acetate/EtOH/water/$NH_4OH$). $^1$H NMR (300 MHz, $CD_3OD$) δ 7.44 (d, 1H, J=7 Hz), 7.16 (d, 1H, J=7 Hz), 6.76 (d, 1H, J=7 Hz), 6.65 (s, 1H), 5.97 (d, 1H, J=7 Hz), 6.06 (m, 1H), 4.52 (t, 2H, J=9 Hz), 3.95 (m, 1H), 3.46 (m, 2H), 3.38 (m, 1H), 3.18 (m, 3H), 2.75 (m, 8H), 1.91 (m, 6H), 1.76 (m, 2H).

SCHEME A
Synthesis of Radioligand for SPA Assay
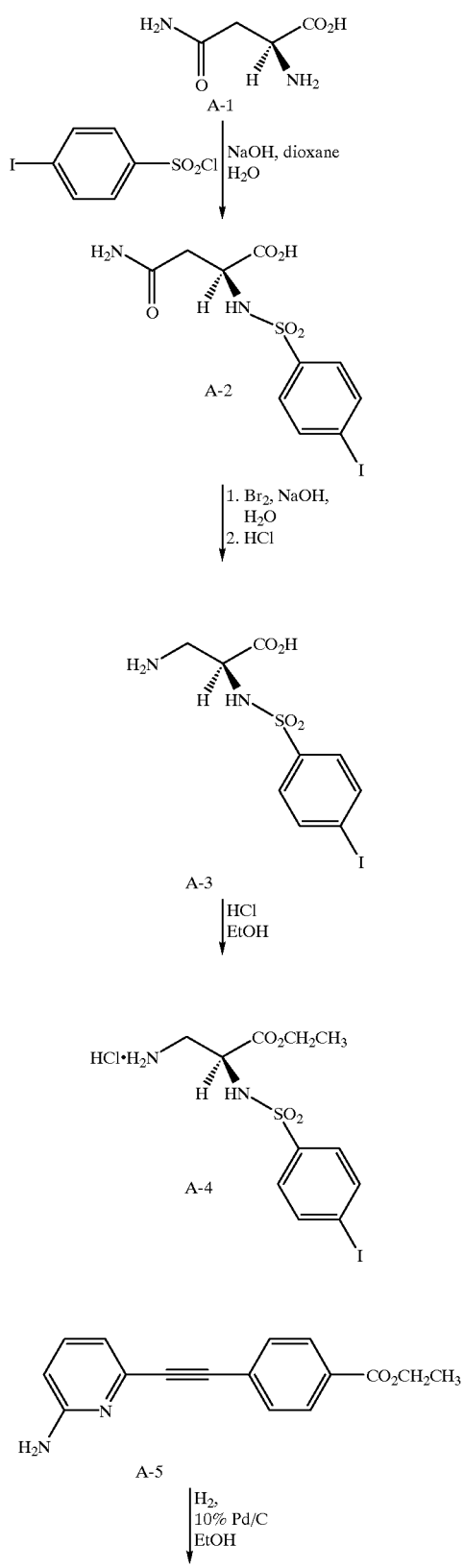
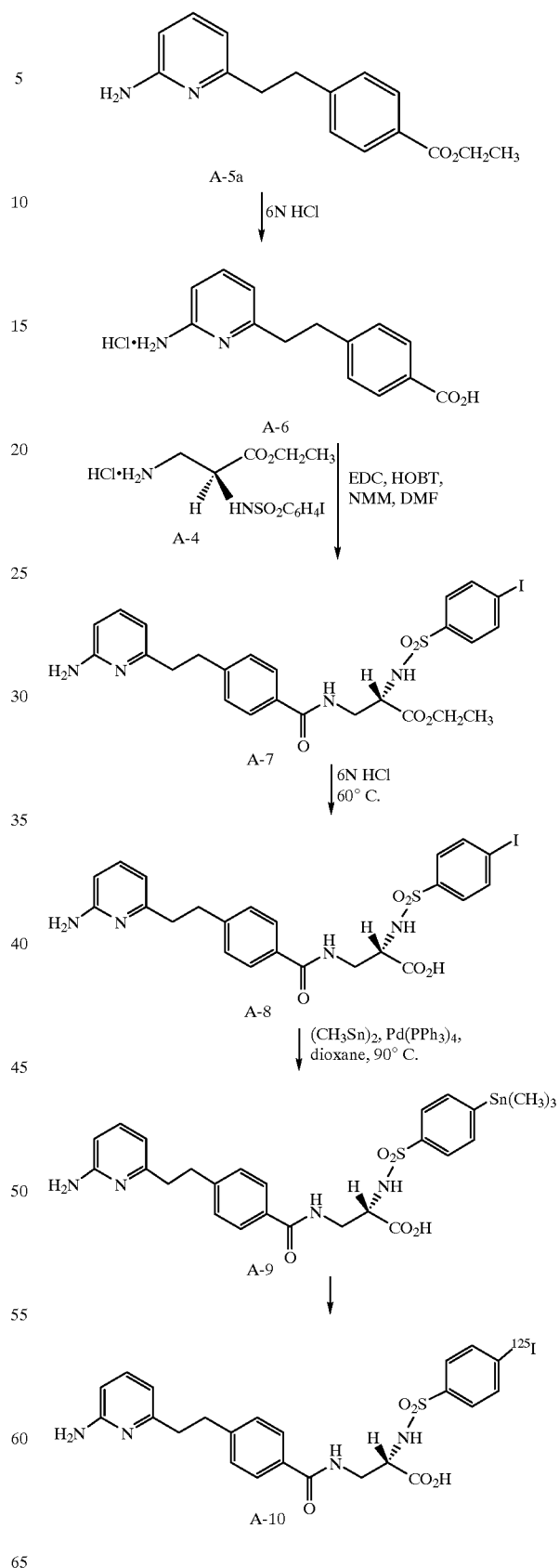

N-(4-Iodo-phenylsulfonylamino)-L-asparagine (A-2)

To a stirred solution of acid A-1 (4.39 g, 33.2 mmol), NaOH (1.49 g, 37.2 mmol), dioxane (30 ml) and $H_2O$ (30 ml) at 0° C. was added pipsyl chloride (10.34 g, 34.2 mmol). After ~5 minutes, NaOH (1.49, 37.2 mmol), dissolved in 15 ml $H_2O$, was added followed by the removal of the cooling bath. After 2.0 h, the reaction mixture was concentrated. The residue was dissolved in $H_2O$ (300 ml) and then washed with EtOAc. The aqueous portion was cooled to 0° C. and then acidified with concentrated HCl. The solid was collected and then washed with $Et_2O$ to provide acid A-2 as a white solid.

$^1$H NMR (300 MHz, $D_2O$) δ 7.86 (d, 2H, J=8 Hz ), 7.48 (d, 2H, J=8 Hz) 3.70 (m, 1H), 2.39 (m, 2H).

2(S)-(4-Iodo-phenylsulfonylamino)-β-alanine (A-3)

To a stirred solution of NaOH (7.14 g, 181.8 mmol) and $H_2O$ (40 ml) at 0° C. was added $Br_2$ (1.30 ml, 24.9 mmol) dropwise over a ten minute period. After ~5 minutes, acid A-2 (9.9 g, 24.9 mmol), NaOH (2.00 g, 49.8 mmol) and $H_2O$ (35 ml) were combined, cooled to 0° C. and then added in a single portion to the reaction. After stirring for 20 minutes at 0° C., the reaction was heated to 90° C. for 30 minutes and then recooled to 0° C. The pH was adjusted to ~7 by dropwise addition of concentrated HC. The solid was collected, washed with EtOAc, and then dried in vacuo to provide acid A-3 as a white solid.

$^1$H NMR (300 MHz, $D_2O$) δ 8.02 (d, 2H, J=8 Hz), 7.63 (d, 2H, J=8 Hz), 4.36 (m, 1H), 3.51 (dd, 1H, J=5 Hz, 13 Hz) 3.21 (m, 1H).

Ethyl 2(S)-(4-iodo-phenylsulfonylamino)-β-alanine-hydrochloride (A-4)

HCl gas was rapidly bubbled through a suspension of acid A-3 (4.0 g, 10.81 mmol) in EtOH (50 ml) at 0° C. for 10 minutes. The cooling bath was removed and the reaction was heated to 60° C. After 18 h, the reaction was concentrated to provide ester A-4 as a white solid.

$^1$H NMR (300 MHz, $CD_3OD$) δ 7.98 (d, 2H, J=8 Hz), 7.63 (d, 2H, J=8 Hz), 4.25 (q, 1H, J=5 Hz), 3.92 (m, 2H), 3.33 (m, 1H), 3.06 (m, 1H), 1.01 (t, 3H, J=7 Hz).

Ethyl 4-[2-(2-Aminopyridin-6-yl)ethyl]benzoate (A-5a)

A mixture of ester A-5 (700 mg, 2.63 mmol), (for preparation, see: Scheme 29 of PCT International Application Publication No. WO 95/32710, published Dec. 7, 1995) 10% Pd/C (350 mg) and EtOH were stirred under 1 atm $H_2$. After 20 h, the reaction was filtered through a celite pad and then concentrated to provide ester A-5a as a brown oil.

TLC $R_f$=0.23 (silica, 40% EtOAc/hexanes); $^1$H NMR (300 MHz, $CDCl_3$) δ 7.95 (d, 2H, J=8 Hz), 7.26 (m, 3H), 6.43 (d, 1H, J=7 Hz), 6.35 (d, 1H, J=8 Hz), 4.37 (m, 4H), 3.05 (m, 2H), 2.91 (m, 2H), 1.39 (t, 3H, J=7 Hz).

4-[2-(2-Aminopyridin-6-yl)ethyl]benzoic acid hydrochloride (A-6)

A suspension of ester A-5a (625 mg, 2.31 mmol) in 6N HCl (12 ml) was heated to 60° C. After ~20 h, the reaction was concentrated to give acid A-6 as a tan solid.

$^1$H NMR (300 MHz, $CD_3OD$) δ 7.96 (d, 2H, J=8 Hz), 7.80 (m, 1H), 7.33 (d, 2H, J=8 Hz), 6.84 (d, 1H, J=9 Hz), 6.69 (d, 1H, J=7 Hz), 3.09 (m, 4H).

Ethyl 4-[2-(2-Aminopyridin-6-yl)ethyl]benzoyl-2(S)-(4-iodophenylsulfonylamino)-β-alanine (A-7)

A solution of acid 15-6 (400 mg, 1.43 mmol), amine A-4 (686 mg, 1.57 mmol), EDC (358 mg, 1.86 mmol), HOBT (252 mg, 1.86 mmol), NMM (632 μl, 5.72 mmol) in DMF (10 ml) was stirred for ~20 h. The reaction was diluted with EtOAc and then washed with sat. $NaHCO_3$, brine, dried ($MgSO_4$) and concentrated. Flash chromatography (silica, EtOAc then 5% isopropanol/EtOAc) provided amide A-7 as a white solid.

TLC $R_f$=0.4 (silica, 10% isopropanol/EtOAc); $^1$H NMR (300 MHz, $CD_3OD$) δ 7.79 (d, 2H, J=9 Hz) 7.61 (d, 2H, J=8 Hz), 7.52 (d, 2H, J=9 Hz), 7.29 (m, 1H), 7.27 (d, 2H, J=8 Hz), 4.20 (m, 1H), 3.95 (q, 2H, J=7 Hz), 3.66 (dd, 1H, J=6 Hz, 14 Hz), 3.49 (dd, 1H, J=8 Hz, 13 Hz), 3.01 (m, 2H), 2.86 (m, 2H), 1.08 (t, 3H, J=7 Hz).

4-[2-(2-Aminopyridin-6-yl)ethyl]benzoyl-2(S)-(4-iodophenylsulfonylamino)-β-alanine (A-8)

A solution of ester A-7 (200 mg, 0.3213 mmol) and 6N HCl (30 ml) was heated to 60° C. After ~20 h, the reaction mixture was concentrated. Flash chromatography (silica, 20:20:1:1 EtOAc/EtOH/$NH_4OH$/$H_2O$) provided acid A-8 as a white solid.

TLC $R_f$=0.45 (silica, 20:20:1:1 EtOAc/EtOH/$NH_4OH$/$H_2O$); $^1$H NMR (400 MHz, DMSO) δ 8.40 (m, 1H), 8.14 (Bs, 1H), 7.81 (d, 2H, J=8 Hz), 7.62 (d, 2H, J=8 Hz), 7.48 (d, 2H, J=8 Hz), 7.27 (m, 3H), 6.34 (d, 1H, J=7 Hz), 6.25 (d, 1H, J=8 Hz), 5.85 (bs, 2H), 3.89 (bs, 1H), 3.35 (m, 2H), 2.97 (m, 2H), 2.79 (m, 2H).

4-[2-(2-Aminopyridin-6-yl)ethyl]benzoyl-2(S)-(4-trimethylstannyl-phenylsulfonylamino)-β-alanine (A-9)

A solution of iodide A-8 (70 mg, 0.1178 mmol), [$(CH_3)_3Sn$]$_2$ (49 μl, 0.2356 mmol), Pd(PPh$_3$)$_4$ (5 mg) and dioxane (7 ml) was heated to 90° C. After 2 h, the reaction was concentrated and then purified by preparative HPLC (Delta-Pak $C_{18}$ 15 μM 100A°, 40×100 mm; 95:5 then 5:95 $H_2O$/$CH_3CN$) to provide the trifluoroacetate salt. The salt was suspended in $H_2O$ (10 ml), treated with $NH_4OH$ (5 drops) and then lyophilized to provide amide A-9 as a white solid.

$^1$H NMR (400 MHz, DMSO) δ 8.40 (m, 1H), 8.18 (d, 1H, J=8 Hz), 7.67 (m, 5H), 7.56 (d, 2H, J=8 Hz), 7.29 (d, 2H, J=8 Hz), 6.95–7.52 (m, 2H), 6.45 (bs, 2H), 4.00 (m, 1H), 3.50 (m, 1H), 3.33 (m, 1H), 2.97 (m, 2H), 2.86 (m, 2H).

4-[2-(2-Aminopyridin-6-yl)ethyl]benzoyl-2(S)-4-$^{125}$iodo-phenylsulfonylamino-β-alanine (A-10)

An iodobead (Pierce) was added to a shipping vial of 5 mCi of $Na^{125}I$ (Amersham, IMS30) and stirred for five minutes at room temperature. A solution of 0.1 mg of A-9 in 0.05 mL of 10% $H_2SO_4$/MeOH was made and immediately added to the $Na^{125}I$/iodobead vial. After stirring for three minutes at room temperature, approximately 0.04–0.05 mL of $NH_4OH$ was added so the reaction mixture was at pH 6–7. The entire reaction mixture was injected onto the HPLC for purification [Vydac peptide-protein C-18 column, 4.6×250 mm, linear gradient of 10% acetonitrile (0.1% (TFA):$H_2O$ (0.1% TFA) to 90% acetonitrile (0.1% TFA):$H_2O$ (0.1% TFA) over 30 minutes, 1 mL/min]. The retention time of A-10 is 17 minutes under these conditions. Fractions containing the majority of the radioactivity were pooled, lyophilized and diluted with ethanol to give approximately 1 mCi of A-10, which coeluted on HPLC analysis with an authentic sample of A-8.

Instrumentation:

Analytical and preparative HPLC was carried out using a Waters 600E Powerline Multi Solvent Delivery System with 0.1 mL heads with a Rheodyne 7125 injector and a Waters 990 Photodiode Array Detector with a Gilson FC203 Microfraction collector. For analytical and preparative HPLC, a Vydac peptide-protein C-18 column, 4.6×250 mm was used with a C-18 Brownlee modular guard column. The acetonitrile used for the HPLC analyses was Fisher Optima grade. The HPLC radiodetector used was a Beckman 170 Radioisotope detector. A Vydac C-18 protein and peptide column, 3.9×250 mm was used for analytical and preparative HPLC. Solutions of radioactivity were concentrated using a Speedvac vacuum centrifuge. Calibration curves and chemical concentrations were determined using a Hewlett Packard Model 8452A UV/Vis Diode Array Spectrophotometer. Sample radioactivities were determined in a Packard A5530 gamma counter.

The test procedures employed to measure αvβ3 and αvβ5 binding and the bone resorption inhibiting activity of the compounds of the present invention are described below.

BONE RESORPTION-PIT ASSAY

When osteoclasts engage in bone resorption, they can cause the formation of pits in the surface of bone that they are acting upon. Therefore, when testing compounds for their ability to inhibit osteoclasts, it is useful to measure the ability of osteoclasts to excavate these resorption pits when the inhibiting compound is present.

Consecutive 200 micron thick cross sections from a 6 mm cylinder of bovine femur diaphysis are cut with a low speed diamond saw (Isomet, Beuler, Ltd., Lake Bluff, Ill.). Bone slices are pooled, placed in a 10% ethanol solution and refrigerated until further use.

Prior to experimentation, bovine bone slices are ultrasonicated twice, 20 minutes each in $H_2O$. Cleaned slices are placed in 96 well plates such that two control lanes and one lane for each drug dosage are available. Each lane represents either triplicate or quadruplicate cultures. The bone slices in 96 well plates are sterilized by UV irradiation. Prior to incubation with osteoclasts, the bone slices are hydrated by the addition of 0.1 ml αMEM, pH 6.9 containing 5% fetal bovine serum and 1% penicillin/streptomycin.

Long bones from 7–14 day old rabbits (New Zealand White Hare) are dissected, cleaned of soft tissue and placed in αMEM containing 20 mM HEPES. The bones are minced using scissors until the pieces are <1 mm and transferred to a 50 ml tube in a volume of 25 ml. The tube is rocked gently by hand for 60 cycles, the tissue is sedimented for 1 min., and the supernatant is removed. Another 25 ml of medium is added to the tissue and rocked again. The second supernatant is combined with the first. The number of cells is counted excluding erythrocytes (typically ~$2\times10^7$ cells/ml). A cell suspension consisting of $5\times10^6$/ml in αMEM containing 5% fetal bovine serum, 10 nM $1,25(OH)_2D_3$, and pencillin-streptomycin is prepared. 200 ml aliquots are added to bovine bone slices (200 mm×6 mm) and incubated for 2 hrs. at 37° C. in a humidified 5% $CO_2$ atmosphere. The medium is removed gently with a micropipettor and fresh medium containing test compounds is added. The cultures are incubated for 48 hrs., and assayed for c-telopeptide (fragments of the al chain of type I collagen) by Crosslaps for culture media (Herlev, Denmark).

Bovine bone slices are exposed to osteoclasts for 20–24 hrs and are processed for staining. Tissue culture media is removed from each bone slice. Each well is washed with 200 ml of $H_2O$, and the bone slices are then fixed for 20 minutes in 2.5% glutaraldehyde, 0.1 M cacodylate, pH 7.4. After fixation, any remaining cellular debris is removed by 2 min. ultrasonication in the presence of 0.25 M $NH_4OH$ followed by 2×15 min ultrasonication in $H_2O$. The bone slices are immediately stained for 6–8 min with filtered 1% toluidine blue and 1% borax.

After the bone slices have dried, resorption pits are counted in test and control slices. Resorption pits are viewed in a Microphot Fx (Nikon) fluorescence microscope using a polarizing Nikon IGS filter cube. Test dosage results are compared with controls and resulting $IC_{50}$ values are determined for each compound tested.

The appropriateness of extrapolating data from this assay to mammalian (including human) disease states is supported by the teaching found in Sato, M., et al., *Journal of Bone and Mineral Research*, Vol. 5, No. 1, pp. 31–40, 1990, which is incorporated by reference herein in its entirety. This article teaches that certain bisphosphonates have been used clinically and appear to be effective in the treatment of Paget's disease, hypercalcemia of malignancy, osteolytic lesions produced by bone metastases, and bone loss due to immobilization or sex hormone deficiency. These same bisphosphonates are then tested in the resorption pit assay described above to confirm a correlation between their known utility and positive performance in the assay.

EIB ASSAY

Duong et al., *J. Bone Miner. Res.*, 8: S378 (1993) describes a system for expressing the human integrin αvβ3. It has been suggested that the integrin stimulates attachment of osteoclasts to bone matrix, since antibodies against the integrin, or RGD-containing molecules, such as echistatin (European Publication 382 451), can effectively block bone resorption.

Reaction Mixture:
1. 175 μl TBS buffer (50 mM Tris.HCl pH 7.2, 150 mM NaCl, 1% BSA, 1 mM $CaCl_2$, 1 mM $MgCl_2$).
2. 25 μl cell extract (dilute with 100 mM octylglucoside buffer to give 2000 cpm/25 μl).
3. $^{125}$I-echistatin (25 μl/50,000 cpm) (see EP 382 451).
4. 25 μl buffer (total binding) or unlabeled echistatin (non-specific binding).

The reaction mixture was then incubated for 1 h at room temp. The unbound and the bound αvβ3 were separated by filtration using a Skatron Cell Harvester. The filters (prewet in 1.5% polyethyleneimine for 10 mins) were then washed with the wash buffer (50 mM Tris HCl, 1 mM $CaCl_2$/$MgCl_2$, pH 7.2). The filter was then counted in a gamma counter.

SPA ASSAY

MATERIALS

1. Wheat germ agglutinin Scintillation Proximity Beads (SPA): Amersham
2. Octylglucopyranoside: Calbiochem
3. HEPES: Calbiochem
4. NaCl: Fisher
5. $CaCl_2$: Fisher
6. $MgCl_2$: SIGMA
7. Phenylmethylsulfonylfluoride (PMSF): SIGMA
8. Optiplate: PACKARD
9. Compound A-10 (specific activity 500–1000 Ci/mmole)
10. test compound
11. Purified integrin receptor: $α_vβ_3$ was purified from 293 cells overexpressing $α_vβ_3$ (Duong et al., *J. Bone Min. Res.*, 8:S378, 1993) according to Pytela (*Methods in Enzymology*, 144:475, 1987)
12. Binding buffer: 50 mM HEPES, pH 7.8, 100 mM NaCl, 1 mM $Ca^{2+}$/$Mg^{2+}$, 0.5 mM PMSF
13. 50 mM octylglucoside in binding buffer: 50-OG buffer

PROCEDURE

1. Pretreatment of SPA beads:
   500 mg of lyophilized SPA beads were first washed four times with 200 ml of 50-OG buffer and once with 100 ml of binding buffer, and then resuspended in 12.5 ml of binding buffer.
2. Preparation of SPA beads and receptor mixture
   In each assay tube, 2.5 μl (40 mg/ml) of pretreated beads were suspended in 97.5 μl of binding buffer and 20 μl of 50-OG buffer. 5 μl (~30 ng/μl) of purified receptor was added to the beads in suspension with stirring at room temperature for 30 minutes. The mixture was then centrifuged at 2,500 rpm in a Beckman GPR Benchtop centrifuge for 10 minutes at 4° C. The pellets were then resuspended in 50 μl of binding buffer and 25 μl of 50-OG buffer.

3. Reaction

The following were sequentially added into Optiplate in corresponding wells:
   (i) Receptor/beads mixture (75 ml)
   (ii) 25 μl of each of the following: compound to be tested, binding buffer for total binding or A-8 for non-specific binding (final concentration 1 μM)
   (iii) A-10 in binding buffer (25 μl, final concentration 40 pM)
   (iv) Binding buffer (125 μl)
   (v) Each plate was sealed with plate sealer from PACKARD and incubated overnight with rocking at 4° C.

4. Plates were counted using PACKARD TOPCOUNT

5. % inhibition was calculated as follows:
   A=total counts
   B=nonspecific counts
   C=sample counts
   % inhibition=$[\{(A-B)-(C-B)\}/(A-B)]/(A-B) \times 100$

OCFORM ASSAY

Osteoblast-like cells (1.8 cells), originally derived from mouse calvaria, were plated in CORNING 24 well tissue culture plates in αMEM medium containing ribo- and deoxyribonucleosides, 10% fetal bovine serum and penicillin-streptomycin. Cells were seeded at 40,000/well in the morning. In the afternoon, bone marrow cells were prepared from six week old male Balb/C mice as follows:

Mice were sacrificed, tibiae removed and placed in the above medium. The ends were cut off and the marrow was flushed out of the cavity into a tube with a 1 mL syringe with a 27.5 gauge needle. The marrow was suspended by pipetting up and down. The suspension was passed through >100 μm nylon cell strainer. The resulting suspension was centrifuged at 350×g for seven minutes. The pellet was resuspended, and a sample was diluted in 2% acetic acid to lyse the red cells. The remaining cells were counted in a hemacytometer. The cells were pelleted and resuspended at $1 \times 10^6$ cells/mL. 50 μL was added to each well of 1.8 cells to yield 50,000 cells/well and 1,25-dihydroxy-vitamin $D_3$ ($D_3$) was added to each well to a final concentration of 10 nM. The cultures were incubated at 37° C. in a humidified, 5% $CO_2$ atmosphere. After 48 h, the medium was changed. 72 h after the addition of bone marrow, test compounds were added with fresh medium containing $D_3$ to quadruplicate wells. Compounds were added again after 48 h with fresh medium containing $D_3$. After an additional 48 h., the medium was removed, cells were fixed with 10% formaldehyde in phosphate-buffered saline for 10 minutes at room temperature, followed by a 1–2 minute treatment with ethanol:acetone (1:1) and air dried. The cells were then stained for tartrate resistant acid phosphatase as follows:

The cells were stained for 10–15 minutes at room temperature with 50 mM acetate buffer, pH 5.0 containing 30 mM sodium tartrate, 0.3 mg/mL Fast Red Violet LB Salt and 0.1 mg/mL Naphthol AS-MX phosphate. After staining, the plates were washed extensively with deionized water and air dried. The number of multinucleated, positive staining cells was counted in each well.

αvβ5 ATTACHMENT ASSAY

Duong et al., *J. Bone Miner. Res.*, 11: S290 (1996), describes a system for expressing the human αvβ5 integrin receptor.

Materials:
1. Media and solutions used in this assay are purchased from BRL/Gibco, except BSA and the chemicals are from Sigma.
2. Attachment medium: HBSS with 1 mg/ml heat-inactivated fatty acid free BSA and 2 mM $CaCl_2$.
3. Glucosaminidase substrate solution: 3.75 mM p-nitrophenyl N-acetyl-beta-D-glucosaminide, 0.1 M sodium citrate, 0.25% Triton, pH 5.0.
4. Glycine-EDTA developing solution: 50 mM glycine, 5 mM EDTA, pH 10.5.

Methods:
1. Plates (96 well, Nunc Maxi Sorp) were coated overnight at 4° C. with human vitronectin (3 ug/ml) in 50 mM carbonate buffer (pH 9/0.6), using 100 μl/well. Plates were then washed 2× with DPBS and blocked with 2% BSA in DPBS for 2 h at room temperature. After additional washes (2×) with DPBS, plates were used for cell attachment assay.
2. 293 (αvβ5) cells were grown in MEM media in presence of 10% fetal calf serum to 90% confluence. Cells were then lifted from dishes with 1× Trypsin/EDTA and washed 3× with serum free MEM. Cells were resuspended in attachment medium ($3 \times 10^5$ cells/ml).
3. Test compounds were prepared as a series of dilutions at 2× concentrations and added as 50 μl/well. Cell suspension was then added as 50 μl/well. Plates were incubated at 37° C. with 55 $CO_2$ for 1 hour to allow attachment.
4. Non-adherent cells were removed by gently washing the plates (3×) with DPBS and then incubated with glucosaminidase substrate solution (100 μl/well), overnight at room temperature in the dark. To quantitate cell numbers, standard curve of glucosaminidase activity was determined for each experiment by adding samples of cell suspension directly to wells containing the enzyme substrate solution.
5. The next day, the reaction was developed by addition of 185 μl/well of glycine/EDTA solution and reading absorbance at 405 nm using a Molecular Devices V-Max plate reader. Average test absorbance values (4 wells per test samples) were calculated. Then, the number of attached cells at each drug concentration was quantitated versus the standard curve of cells using the Softmax program.

EXAMPLE OF A PHARMACEUTICAL FORMULATION

As a specific embodiment of an oral composition, 100 mg of a compound of the present invention are formulated with sufficient finely divided lactose to provide a total amount of 580 to 590 mg to fill a size O hard gel capsule.

Representative compounds of the present invention were tested and found to bind to human αvβ3 integrin. These compounds are generally found to have $IC_{50}$ values less than about 100 nM in the SPA assay.

Representative compounds of the present invention were tested and generally found to inhibit ≧50% the attachment of αvβ5 expressing cells to plates coated with vitronectin at concentrations of about 1 μM.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of the formula

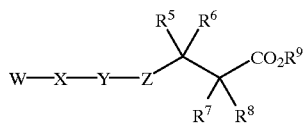

wherein W is selected from the group consisting of

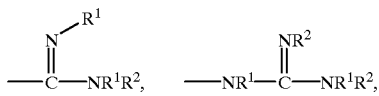

a 5- or 6-membered monocyclic aromatic or nonaromatic ring system having 1, 2, 3 or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents, and a 9- to 14-membered polycyclic ring system, wherein one or more of the rings is aromatic, and wherein the polycyclic ring system has 0, 1, 2, 3 or 4 heteroatoms selected from the group consisting of N, O, and S, and wherein the ring nitrogen atoms are unsubstituted or substituted with one $R^1$ substituent and the ring carbon atoms are unsubstituted or substituted with one or two $R^1$ substituents;

X is selected from the group consisting of

—$(CH_2)_v$—, wherein any methylene ($CH_2$) carbon atom is either unsubstituted or substituted with one or two $R^1$ substitutents;

and a 5- or 6-membered monocyclic aromatic or nonaromatic ring system having 0, 1, 2, 3 or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents;

Y is selected from the group consisting of

—$(CH_2)_m$—,
—$(CH_2)_m$—O—$(CH_2)_n$—,
—$(CH_2)_m$—$NR^4$—$(CH_2)_n$—,
—$(CH_2)_m$—S—$(CH_2)_n$—,
—$(CH_2)_m$—SO—$(CH_2)_n$—,
—$(CH_2)_m$—$SO_2$—$(CH_2)_n$—,
—$(CH_2)_m$—O—$(CH_2)_n$—O—$(CH_2)_p$—,
—$(CH_2)_m$—O—$(CH_2)_n$—$NR^4$—$(CH_2)_p$—,
—$(CH_2)_m$—$NR^4$—$(CH_2)_n$—$NR^4$—$(CH_2)_p$—,
—$(CH_2)_m$—O—$(CH_2)_n$—S—$(CH_2)_p$—,
—$(CH_2)_m$—S—$(CH_2)_n$—S—$(CH_2)_p$—,
—$(CH_2)_m$—$NR^4$—$(CH_2)_n$—S—$(CH_2)_p$—,
—$(CH_2)_m$—$NR^4$—$(CH_2)_n$—O—$(CH_2)_p$—,
—$(CH_2)_m$—S—$(CH_2)_n$—O—$(CH_2)_p$—, and
—$(CH_2)_m$—S—$(CH_2)_n$—$NR^4$—$(CH_2)_p$—, wherein any methylene ($CH_2$) carbon atom in Y, other than in $R^4$, can be substituted by one or two $R^3$ substituents;

Z is

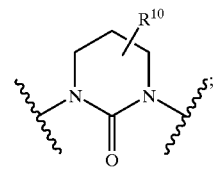

$R^1$ and $R^2$ are each independently selected from the group consisting of hydrogen, halogen, $C_{1-10}$ alkyl, $C_{3-8}$ cycloalkyl, $C_{3-8}$ cycloheteroalkyl, $C_{3-8}$ cycloalkyl $C_{1-6}$ alkyl, $C_{3-8}$ cycloheteroalkyl $C_{1-6}$ alkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $(C_{1-6}$ alkyl$)_p$amino, $(C_{1-6}$ alkyl$)_p$ amino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-3}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, $C_{1-6}$ alkyloxy-$C_{1-6}$ alkyl, nitro, cyano, trifluoromethyl, trifluoromethoxy, trifluoroethoxy, $C_{1-8}$ alkyl-$S(O)_p$, $(C_{1-8}$ alkyl$)_p$aminocarbonyl, $C_{1-8}$ alkyloxycarbonylamino, $(C_{1-8}$ alkyl$)_p$ aminocarbonyloxy, (aryl $C_{1-8}$ alkyl$)_p$amino, (aryl$)_p$ amino, aryl $C_{1-8}$ alkylsulfonylamino, and $C_{1-8}$ alkylsulfonylamino;

or two $R^1$ substituents, when on the same carbon atom, are taken together with the carbon atom to which they are attached to form a carbonyl group;

each $R^3$ is independently selected from the group consisting of hydrogen,
aryl,
$C_{1-10}$ alkyl,
aryl-$(CH_2)_r$—O—$(CH_2)_s$—,
aryl-$(CH_2)_r$$S(O)_p$—$(CH_2)_s$—,
aryl-$(CH_2)_r$—C(O)—$(CH_2)_s$—,
aryl-$(CH_2)_r$—C(O)—N($R^4$)—$(CH_2)_s$—,
aryl-$(CH_2)_r$—N($R^4$)—C(O)—$(CH_2)_s$—,
aryl-$(CH_2)_r$—N($R^4$)—$(CH_2)_s$—,
halogen,
hydroxyl,
oxo,
trifluoromethyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl, $C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
$HC{\equiv}C{-}(CH_2)_t{-}$,
$C_{1-6}$ alkyl-$C{\equiv}C{-}(CH_2)_t{-}$,
$C_{3-7}$ cycloalkyl-$C{\equiv}C{-}(CH_2)_t{-}$,
aryl-$C{\equiv}C{-}(CH_2)_t{-}$,
$C_{1-6}$ alkylaryl-$C{\equiv}C{-}(CH_2)_t{-}$,
$CH_2{=}CH{-}(CH_2)_t{-}$,
$C_{1-6}$ alkyl-$CH{=}CH{-}(CH_2)_t{-}$,
$C_{3-7}$ cycloalkyl-$CH{=}CH{-}(CH_2)_t{-}$,
aryl-$CH{=}CH{-}(CH_2)_t{-}$,
$C_{1-6}$ alkylaryl-$CH{=}CH{-}(CH_2)_t{-}$,
$C_{1-6}$ alkyl-$SO_2{-}(CH_2)_t{-}$,
$C_{1-6}$ alkylaryl-$SO_2{-}(CH_2)_t{-}$,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
(aryl$)_p$amino,
(aryl$)_p$amino $C_{1-6}$ alkyl,
(aryl $C_{1-6}$ alkyl$)_p$amino,
(aryl $C_{1-6}$ alkyl$)_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl$)_p$aminocarbonyl $C_{1-6}$ alkyl,
(aryl $C_{1-8}$ alkyl$)_p$aminocarbonyl, and
(aryl $C_{1-8}$ alkyl$)_p$aminocarbonyl $C_{1-6}$ alkyl;
or two $R^3$ substituents, when on the same carbon atom are taken together with the carbon atom to which they are attached to form a carbonyl group or a cyclopropyl group, wherein any of the alkyl groups of $R^3$ are either unsubstituted or substituted with one to three $R^1$ substituents, and provided that each $R^3$ is selected such that in the resultant compound the carbon atom or atoms to which $R^3$ is attached is itself attached to no more than one heteroatom;

each $R^4$ is independently selected from the group consisting of
hydrogen,
aryl,
aminocarbonyl,
$C_{3-8}$ cycloalkyl,
amino $C_{1-6}$ alkyl,
(aryl$)_p$aminocarbonyl,
(aryl $C_{1-5}$ alkyl$)_p$aminocarbonyl,
hydroxycarbonyl $C_{1-6}$ alkyl,
$C_{1-8}$ alkyl,
aryl $C_{1-6}$ alkyl,
$(C_{1-6}$ alkyl$)_p$amino $C_{2-6}$ alkyl,
(aryl $C_{1-6}$ alkyl$)_p$amino $C_{2-6}$ alkyl,
$C_{1-8}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
$(C_{1-8}$ alkyl$)_p$aminocarbonyl,
aminosulfonyl,
$C_{1-8}$ alkylaminosulfonyl,
(aryl$)_p$aminosulfonyl,
(aryl $C_{1-8}$ alkyl$)_p$aminosulfonyl, arylsulfonyl,
aryl $C_{1-6}$ alkylsulfonyl,
$C_{1-6}$ alkylthiocarbonyl,
arylthiocarbonyl, and
aryl $C_{1-6}$ alkylthiocarbonyl,
wherein any of the alkyl groups of $R^4$ are either unsubstituted or substituted with one to three $R^1$ substituents;
$R^5$ and $R^6$ are each independently selected from the group consisting of
hydrogen,
$C_{1-10}$ alkyl,
aryl,
aryl-$(CH_2)_r$—O—$(CH_2)_s$—,
aryl-$(CH_2)_r$S$(O)_p$—$(CH_2)_s$—,
aryl-$(CH_2)_r$—C(O)—$(CH_2)_s$—,
aryl-$(CH_2)_r$—C(O)—N($R^4$)—$(CH_2)_s$—,
aryl-$(CH_2)_r$—N($R^4$)—C(O)—$(CH_2)_s$—,
aryl-$(CH_2)_r$—N($R^4$)—$(CH_2)_s$—,
halogen,
hydroxyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl-C≡C—$(CH_2)_t$—,
$C_{3-7}$ cycloalkyl-C≡C—$(CH_2)_t$—,
aryl-C≡C—$(CH_2)_t$—,
$C_{1-6}$ alkylaryl-C≡C—$(CH_2)_t$—,
$CH_2$=CH—$(CH_2)_t$—,
$C_{1-6}$ alkyl-CH=CH—$(CH_2)_t$—,
$C_{3-7}$ cycloalkyl-CH=CH—$(CH_2)_t$—,
aryl-CH=CH—$(CH_2)_t$—,
$C_{1-6}$ alkylaryl-CH=CH—$(CH_2)_t$—,
$C_{1-6}$ alkyl-$SO_2$—$(CH_2)_t$—,
$C_{1-6}$ alkylaryl-$SO_2$—$(CH_2)_t$—,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
(aryl$)_p$amino,
(aryl$)_p$amino $C_{1-6}$ alkyl,
(aryl $C_{1-6}$ alkyl$)_p$amino,
(aryl $C_{1-6}$ alkyl$)_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl$)_p$aminocarbonyl $C_{1-6}$ alkyl,
(aryl $C_{1-8}$ alkyl$)_p$aminocarbonyl,
and (aryl $C_{1-8}$ alkyl$)_p$aminocarbonyl $C_{1-6}$ alkyl;
or $R^5$ and $R^6$ are taken together with the carbon atom to which they are attached to form a carbonyl group,
wherein any of the alkyl groups of $R^5$ or $R^6$ are either unsubstituted or substituted with one to three $R^1$ substituents, and provided that each $R^5$ and $R^6$ are selected such that in the resultant compound the carbon atom to which $R^5$ and $R^6$ are attached is itself attached to no more than one heteroatom;
$R^7$ and $R^8$ are each independently selected from the group consisting of
hydrogen, $C_{1-10}$ alkyl,
aryl,
aryl-$(CH_2)_r$—O—$(CH_2)_s$—,
aryl-$(CH_2)_r$S(O)$_p$—$(CH_2)_s$—,
aryl-$(CH_2)_r$—C(O)—$(CH_2)_s$—,
aryl-$(CH_2)_r$—C(O)—N($R^4$)—$(CH_2)_s$—,
aryl-$(CH_2)_r$—N($R^4$)—C(O)—$(CH_2)_s$—,
aryl-$(CH_2)_r$—N($R^4$)—$(CH_2)_s$—,
halogen,
hydroxyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl-C≡C—$(CH_2)_t$—,
$C_{3-7}$ cycloalkyl-C≡C—$(CH_2)_t$—,
aryl-C≡C—$(CH_2)_t$—,
$C_{1-6}$ alkylaryl-C≡C—$(CH_2)_t$—,
$CH_2$=CH—$(CH_2)_t$—,
$C_{1-6}$ alkyl-CH=CH—$(CH_2)_t$—,
$C_{3-7}$ cycloalkyl-CH=CH—$(CH_2)_t$—,
aryl-CH=CH—$(CH_2)_t$—,
$C_{1-6}$ alkylaryl-CH=CH—$(CH_2)_t$—,
$C_{1-6}$ alkyl-$SO_2$—$(CH_2)_t$—,
$C_{1-6}$ alkylaryl-$SO_2$—$(CH_2)_t$—,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
(aryl$)_p$amino,
(aryl$)_p$amino $C_{1-6}$ alkyl,
(aryl $C_{1-6}$ alkyl$)_p$amino,
(aryl $C_{1-6}$ alkyl$)_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylcarbonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
arylaminocarbonylamino,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl$)_p$aminocarbonyl $C_{1-6}$ alkyl,
(aryl $C_{1-8}$ alkyl$)_p$aminocarbonyl,
(aryl $C_{1-8}$ alkyl$)_p$aminocarbonyl $C_{1-6}$ alkyl, and
$C_{7-20}$ polycyclyl $C_{0-8}$ alkylsulfonylamino;
wherein any of the alkyl groups of $R^7$ and $R^8$ are either unsubstituted or substituted with one to three $R^1$ substituents, and provided that each $R^7$ and $R^8$ are selected such that in the resultant compound the carbon atom to which $R^7$ and $R^8$ are attached is itself attached to no more than one heteroatom;
$R^9$ is selected from the group consisting of
hydrogen,
$C_{1-8}$ alkyl,
aryl,
aryl $C_{1-8}$ alkyl,
$C_{1-8}$ alkylcarbonyloxy $C_{1-4}$ alkyl,
aryl $C_{1-8}$ alkylcarbonyloxy $C_{1-4}$ alkyl,
$C_{1-8}$ alkylaminocarbonylmethylene, and
$C_{1-8}$ dialkylaminocarbonylmethylene;
$R^{10}$, $R^{11}$, $R^{12}$, and $R^{13}$ are each independently selected from the group consisting of
hydrogen, $C_{1-8}$ alkyl,
aryl,
halogen,
hydroxyl,
oxo,
aminocarbonyl,
$C_{3-8}$ cycloalkyl,
amino $C_{1-6}$ alkyl,
(aryl)$_p$aminocarbonyl,
hydroxycarbonyl,
(aryl $C_{1-5}$ alkyl)$_p$aminocarbonyl,
hydroxycarbonyl $C_{1-6}$ alkyl,
aryl $C_{1-6}$ alkyl,
($C_{1-6}$ alkyl)$_p$amino $C_{1-6}$ alkyl,
(aryl $C_{1-6}$ alkyl)$_p$amino $C_{2-6}$ alkyl,
$C_{1-8}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
($C_{1-8}$ alkyl)$_p$aminocarbonyl,
aminosulfonyl,
$C_{1-8}$ alkylaminosulfonyl,
(aryl)$_p$aminosulfonyl,
(aryl $C_{1-8}$ alkyl)$_p$aminosulfonyl,
$C_{1-6}$ alkylsulfonyl,
arylsulfonyl,
aryl $C_{1-6}$ alkylsulfonyl,
aryl $C_{1-6}$ alkylcarbonyl,
$C_{1-6}$ alkylthiocarbonyl,
arylthiocarbonyl,
aryl $C_{1-6}$ alkylthiocarbonyl,
aryl-(CH$_2$)$_r$—O—(CH$_2$)$_s$—,
aryl-(CH$_2$)$_r$S(O)$_p$—(CH$_2$)$_s$—,
aryl-(CH$_2$)$_r$—C(O)—(CH$_2$)$_s$—,
aryl-(CH$_2$)$_r$—C(O)—N(R$^4$)—(CH$_2$)$_s$—,
aryl-(CH$_2$)$_r$—N(R$^4$)—C(O)—(CH$_2$)$_s$—,
aryl-(CH$_2$)$_r$—N(R$^4$)—(CH$_2$)$_s$—,
HC≡C—(CH$_2$)$_t$—,
$C_{1-6}$ alkyl-C≡C—(CH$_2$)$_t$—,
$C_{3-7}$ cycloalkyl-C≡C—(CH$_2$)$_t$—,
aryl-C≡C—(CH$_2$)$_t$—,
$C_{1-6}$ alkylaryl-C≡C—(CH$_2$)$_t$—,
CH$_2$=CH—(CH$_2$)$_t$—,
$C_{1-6}$ alkyl-CH=CH—(CH$_2$)$_t$—,
$C_{3-7}$ cycloalkyl-CH=CH—(CH$_2$)$_t$—,
aryl-CH=CH—(CH$_2$)$_t$—,
$C_{1-6}$ alkylaryl-CH=CH—(CH$_2$)$_t$—,
$C_{1-6}$ alkyl-SO$_2$—(CH$_2$)$_t$—,
$C_{1-6}$ alkylaryl-SO$_2$—(CH$_2$)$_t$—,
$C_{1-8}$ alkylcarbonylamino,
aryl $C_{1-5}$ alkoxy,
$C_{1-5}$ alkoxycarbonyl,
($C_{1-8}$ alkyl)$_p$aminocarbonyl,
$C_{1-6}$ alkylcarbonyloxy,
($C_{1-6}$ alkyl)$_p$amino,
aminocarbonyl $C_{1-6}$ alkyl,
$C_{1-6}$ alkoxy,
aryl $C_{1-6}$ alkoxy,
(aryl)$_p$amino,
(aryl)$_p$amino $C_{1-6}$ alkyl,
(aryl $C_{1-6}$ alkyl)$_p$amino,
(aryl $C_{1-6}$ alkyl)$_p$amino $C_{1-6}$ alkyl,
arylcarbonyloxy,
aryl $C_{1-6}$ alkylcarbonyloxy,
($C_{1-6}$ alkyl)$_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
($C_{1-8}$ alkyl)$_p$aminocarbonylamino,
($C_{1-8}$ alkyl)$_p$aminocarbonylamino $C_{1-6}$ alkyl,
(aryl)$_p$aminocarbonylamino $C_{1-6}$ alkyl,
(aryl $C_{1-8}$ alkyl)$_p$aminocarbonylamino,
(aryl $C_{1-8}$ alkyl)$_p$aminocarbonylamino $C_{1-6}$ alkyl,
aminosulfonylamino $C_{1-6}$ alkyl,
($C_{1-8}$ alkyl)$_p$aminosulfonylamino,
($C_{1-8}$ alkyl)$_p$aminosulfonylamino $C_{1-6}$ alkyl,
(aryl)$_p$aminosulfonylamino $C_{1-6}$ alkyl,
(aryl $C_{1-8}$ alkyl)$_p$aminosulfonylamino,
(aryl $C_{1-8}$ alkyl)$_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
($C_{1-8}$ alkyl)$_p$aminocarbonyl $C_{1-6}$ alkyl, (aryl)$_p$aminocarbonyl C$_{1-6}$ alkyl,
(aryl C$_{1-8}$ alkyl)$_p$aminocarbonyl, and
(aryl C$_{1-8}$ alkyl)$_p$aminocarbonyl C$_{1-6}$ alkyl;
wherein any of the alkyl groups of R$^{10}$, R$^{11}$, R$^{12}$, and R$^{13}$ are either unsubstituted or substituted with one to three R$^1$ substituents;
wherein
  each m is independently an integer from 0 to 6;
  each n is independently an integer from 0 to 6;
  each p is independently an integer from 0 to 2;
  each r is independently an integer from 1 to 3;
  each s is independently an integer from 0 to 3;
  each t is an integer from 0 to 3; and
  v is independently an integer from 0 to 6;
and the pharmaceutically acceptable salts thereof.

2. The compound of claim 1 wherein W is
  a 6-membered monocyclic aromatic ring system having 1 or 2 nitrogen atoms wherein each ring carbon atom is unsubstituted or substituted with one R$^1$ substituent, or
  a 9- to 14-membered polycyclic ring system, wherein one or more of the rings is aromatic, and wherein the polycyclic ring system has 0, 1, 2, 3 or 4 heteroatoms selected from the group consisting of N, O, and S, and wherein the ring nitrogen atoms are unsubstituted or substituted with one R$^1$ substituent and the ring carbon atoms are unsubstituted or substituted with one or two R$^1$ substituents;
X is
  —(CH$_2$)$_v$—, wherein any methylene (CH$_2$) carbon atom is either unsubstituted or substituted with one or two R$^1$ substitutents; and
Z is

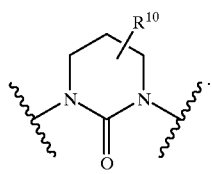

3. The compound of claim 2 wherein W is selected from the group consisting of

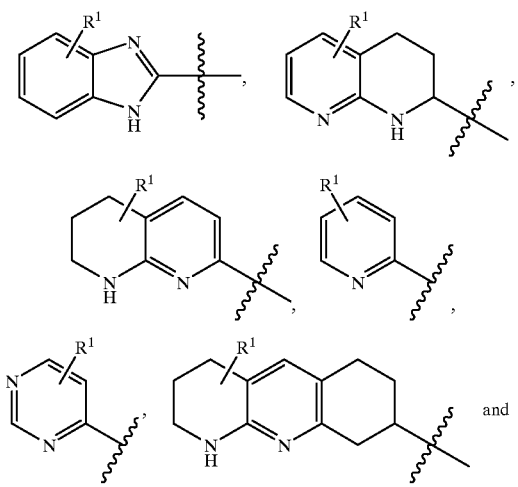

and Z is

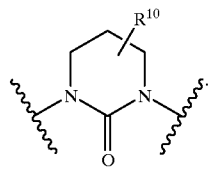

4. The compound of claim 3 wherein W is

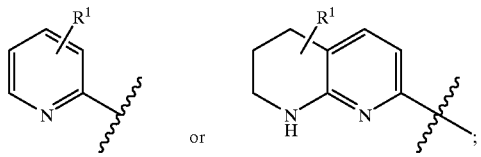

X is —(CH$_2$)$_v$—, wherein any methylene (CH$_2$) carbon atom is either unsubstituted or substituted with one or two R$^1$ substitutents;
Y is selected from the group consisting of
  —(CH$_2$)$_m$—,
  —(CH$_2$)$_m$—O—(CH$_2$)$_n$—,
  —(CH$_2$)$_m$—NR$^4$—(CH$_2$)$_n$—,
  —(CH$_2$)$_m$—S—(CH$_2$)$_n$—,
  —(CH$_2$)$_m$—SO—(CH$_2$)$_n$—,
  —(CH$_2$)$_m$—SO$_2$—(CH$_2$)$_n$—,
  —(CH2)m—O—(CH2)n—O—(CH2)p—,
  —(CH2)m—O—(CH2)n—NR$^4$—(CH2)p—,
  —(CH2)m—NR$^4$—(CH2)n—NR$^4$—(CH2)p—, and
  —(CH2)m—NR$^4$—(CH2)n—O—(CH2)p—;
wherein any methylene (CH$_2$) carbon atom in Y, other than in R$^4$, can be substituted by one or two R$^3$ substituents; and
Z is

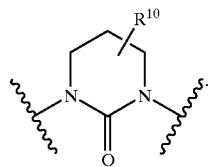

5. The compound of claim 4 wherein Y is selected from the group consisting of
  (CH$_2$)$_m$, (CH$_2$)$_m$—S—(CH$_2$)$_n$, and (CH$_2$)$_m$—NR$^4$—(CH$_2$)$_n$,
wherein any methylene (CH$_2$) carbon atom in Y, other than in R$^4$, can be substituted by one or two R$^3$ substituents;
m and n are integers from 0–3;
and v is 0.

6. The compound of claim 5 wherein each R$^3$ is independently selected from the group consisting of
  hydrogen, fluoro,
trifluoromethyl,
aryl,
$C_{1-8}$ alkyl,
aryl$C_{1-6}$ alkyl
hydroxyl,
oxo,
arylaminocarbonyl,
aryl $C_{1-5}$ alkylaminocarbonyl,
aminocarbonyl, and
aminocarbonyl $C_{1-6}$ alkyl;
and each $R^4$ is independently selected from the group consisting of
hydrogen,
aryl,
$C_{3-8}$ cycloalkyl,
$C_{1-8}$ alkyl,
$C_{1-8}$ alkylcarbonyl,
arylcarbonyl,
$C_{1-6}$ alkylsulfonyl,
arylsulfonyl,
aryl$C_{1-6}$alkylsulfonyl,
aryl$C_{1-6}$alkylcarbonyl,
$C_{1-8}$alkylaminocarbonyl,
aryl$C_{1-5}$alkylaminocarbonyl,
arylC-8alkoxycarbonyl, and
$C_{1-8}$alkoxycarbonyl.

7. The compound of claim 6 wherein $R^6$, $R^7$, and $R^8$ are each hydrogen and $R^5$ is selected from the group consisting of
hydrogen,
aryl,
$C_{1-8}$ alkyl,
aryl-C≡C—(CH$_2$)$_t$—,
aryl $C_{1-6}$ alkyl,
CH$_2$=CH—(CH$_2$)$_t$—, and
HC≡C—(CH$_2$)$_t$—.

8. The compound of claim 7 wherein $R^9$ is selected from the group consisting of hydrogen, methyl, and ethyl.

9. The compound of claim 8 wherein $R^9$ is hydrogen.

10. The compound of claim 6 wherein $R^5$, $R^6$, and $R^8$ are each hydrogen and $R^7$ is selected from the group consisting of
hydrogen,
aryl,
$C_{1-8}$ alkylcarbonylamino,
$C_{1-8}$ alkylsulfonylamino,
arylcarbonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
arylaminocarbonylamino,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino, and
aryl $C_{1-6}$ alkylthiocarbonylamino $C_{1-6}$ alkyl.

11. The compound of claim 10 wherein $R^7$ is selected from the group consisting of
hydrogen,
aryl,
$C_{1-8}$ alkylcarbonylamino,
aryl $C_{1-6}$ alkylcarbonylamino,
arylcarbonylamino,
$C_{1-8}$ alkylsulfonylamino,
aryl $C_{1-6}$ alkylsulfonylamino,
arylsulfonylamino,
$C_{1-8}$ alkoxycarbonylamino,
aryl $C_{1-8}$ alkoxycarbonylamino,
arylaminocarbonylamino,
$(C_{1-8}$ alkyl$)_p$aminocarbonylamino,
(aryl $C_{1-8}$ alkyl$)_p$aminocarbonylamino,
$(C_{1-8}$ alkyl$)_p$aminosulfonylamino, and
(aryl $C_{1-8}$ alkyl$)_p$aminosulfonylamino.

12. The compound of claim 11 wherein $R^9$ is selected from the group consisting of hydrogen, methyl, and ethyl.

13. The compound of claim 12 wherein $R^9$ is hydrogen.

14. The compound of claim 6 selected from the group consisting of:
ethyl 3(S)-(2,3-dihydro-benzofuran-6-yl)-3-{2-oxo-3-[3-(5,6,7,8-tetrahydro-[1,8]naphthyridin-2-yl)-propyl]-tetrahydro-pyrimidin-1-yl}-propionate;
ethyl 3(S)-(3-fluorophenyl)-3-(2-oxo-3(S or R)-[3-(5,6,7,8-tetrahydro-[1,8]naphthyridin-2-yl)-propyl]-piperidin-1-yl)-propionate;
ethyl 3(S)-(3-fluorophenyl)-3-(2-oxo-3(R or S)-[3-(5,6,7,8-tetrahydro-[1,8]naphthyridin-2-yl)-propyl]-piperidin-1-yl)-propionate;
3(S)-(2,3-dihydro-benzofuran-6-yl)-3-{2-oxo-3-[3-(5,6,7,8-tetrahydro-[1,8]naphthyridin-2-yl)-propyl]-tetrahydro-pyrimidin-1-yl}-propionic acid;
3(S)-(3-fluorophenyl)-3-(2-oxo-3(S or R)-[3-(5,6,7,8-tetrahydro-[1,8]naphthyridin-2-yl)-propyl]-piperidin-1-yl)-propionic acid;

3(S)-(3-fluorophenyl)-3-(2-oxo-3(R or S)-[3-(5,6,7,8-tetrahydro-[1,8]naphthyridin-2-yl)-propyl]-piperidin-1-yl)-propionic acid;

and the pharmaceutically acceptable salts thereof.

15. A pharmaceutical composition comprising a compound according to claim 1 and a pharmaceutically acceptable carrier.

16. A pharmaceutical composition made by combining a compound according to claim 1 and a pharmaceutically acceptable carrier.

17. A process for making a pharmaceutical composition comprising/combining a compound according to claim 1 and a pharmaceutically acceptable carrier.

18. A method of inhibiting a condition selected from the group consisting of bone resorption, restenosis, angiogenesis, diabetic retinopathy, macular degeneration, inflammatory arthritis, and tumor growth comprising administering to a mammal in need thereof a therapeutically effective amount of a compound according to claim 1.

19. The method of claim 18 wherein the condition to be inhibited is bone resorption.

20. A method of treating breast cancer, human melanoma or carcinomas of the lung, pancreas, or larynx a mammal in need thereof, comprising administering to the mammal a therapeutically effective amount of a compound according to claim 1 in combination with radiation therapy.

21. A method of treating or preventing osteoporosis which comprises administering to a mammal in need of such treatment or prevention a therapeutically or prophylactically effective amount of a compound of claim 1.

22. A method of treating or preventing osteoporosis which comprises administering to a mammal in need of such treatment or prevention a therapeutically or prophylactically effective amount of a compound of claim 1 in combination with an effective amount of an organic bisphosphonate selected from alendronate, etidronate, pamidronate, resedronate, or ibandronate or a pharmaceutically acceptable salt or ester thereof.

23. The method of claim 22 wherein said organic bisphosphonate or pharmaceutically acceptable salt or ester thereof is alendronate monosodium trihydrate.

* * * * *